United States Patent
Sahin et al.

(10) Patent No.: US 11,395,852 B2
(45) Date of Patent: *Jul. 26, 2022

(54) THERAPY INVOLVING ANTIBODIES AGAINST CLAUDIN 18.2 FOR TREATMENT OF CANCER

(71) Applicants: Ganymed Pharmaceuticals GmbH, Mainz (DE); TRON—Translationale Onkologie an der Universitatsmedizin der Johannes Gutenberg-Universitat Mainz, Mainz (DE)

(72) Inventors: Ugur Sahin, Mainz (DE); Özlem Türeci, Mainz (DE)

(73) Assignees: Astellas Pharma Inc., Tokyo (JP); TRON—Translationale Onkologie an der Universitätmedizin der Johannes Gutenberg-Universität Mainz Gemeinnützige GmbH, Mainz (DE)

(*) Notice: Subject to any disclaimer, the term of this patent is extended or adjusted under 35 U.S.C. 154(b) by 371 days.

This patent is subject to a terminal disclaimer.

(21) Appl. No.: 16/158,187

(22) Filed: Oct. 11, 2018

(65) Prior Publication Data

US 2019/0076525 A1 Mar. 14, 2019

Related U.S. Application Data

(63) Continuation of application No. 14/777,231, filed as application No. PCT/EP2014/000719 on Mar. 17, 2014, now Pat. No. 10,137,195.

(30) Foreign Application Priority Data

Mar. 18, 2013 (WO) .................. PCT/EP2013/000817

(51) Int. Cl.
| | |
|---|---|
| A61K 39/39 | (2006.01) |
| A61K 39/395 | (2006.01) |
| C07K 16/28 | (2006.01) |
| C07K 16/30 | (2006.01) |
| A61K 45/06 | (2006.01) |
| G01N 33/574 | (2006.01) |
| A61K 39/00 | (2006.01) |

(52) U.S. Cl.
CPC ........ A61K 39/39558 (2013.01); A61K 45/06 (2013.01); C07K 16/28 (2013.01); C07K 16/30 (2013.01); G01N 33/57446 (2013.01); G01N 33/57488 (2013.01); G01N 33/57492 (2013.01); A61K 2039/505 (2013.01); A61K 2039/545 (2013.01); C07K 2317/732 (2013.01); C07K 2317/734 (2013.01); C07K 2317/90 (2013.01); G01N 2800/52 (2013.01)

(58) Field of Classification Search
None
See application file for complete search history.

(56) References Cited

U.S. PATENT DOCUMENTS

| | | |
|---|---|---|
| 2006/0035852 A1 | 2/2006 | Sahin et al. |
| 2008/0166350 A1 | 7/2008 | Tureci et al. |
| 2009/0155817 A1 | 6/2009 | Sahin et al. |
| 2009/0169547 A1 | 7/2009 | Sahin et al. |
| 2009/0208498 A1 | 8/2009 | Sahin et al. |
| 2010/0111975 A1 | 5/2010 | Sahin et al. |
| 2010/0166779 A1 | 7/2010 | Sahin et al. |
| 2012/0164160 A1 | 6/2012 | Sahin et al. |
| 2012/0195830 A1 | 8/2012 | Sahin et al. |
| 2012/0258091 A1 | 10/2012 | Sahin et al. |
| 2014/0186338 A1 | 7/2014 | Sahin et al. |
| 2015/0132253 A1 | 5/2015 | Sahin et al. |
| 2015/0147763 A1 | 5/2015 | Sahin et al. |
| 2015/0157711 A1 | 6/2015 | Sahin et al. |
| 2015/0252103 A1 | 9/2015 | Sahin et al. |
| 2015/0252104 A1 | 9/2015 | Sahin et al. |
| 2015/0315287 A1 | 11/2015 | Tureci et al. |
| 2015/0337052 A1 | 11/2015 | Sahin et al. |
| 2015/0374789 A1 | 12/2015 | Sahin et al. |
| 2016/0185860 A1 | 6/2016 | Sahin et al. |
| 2018/0000900 A1 | 1/2018 | Sahin et al. |

FOREIGN PATENT DOCUMENTS

| | | |
|---|---|---|
| BR | 112014028948-4 A8 | 12/2018 |
| EP | 1112364 A2 | 7/2001 |
| EP | 1119620 A2 | 8/2001 |
| EP | 1144629 A2 | 10/2001 |

(Continued)

OTHER PUBLICATIONS

De Vita et al. (British Journal of Cancer, 92: 1644-1649, 2005).*
Baselga et al. (J. Clin. Oncol., 18: 904-914, 2000).*
Tobinai et al. (Annals of Oncology, 9: 527-534, 1998).*
Fioretti et al., Gynecologic Oncology, 44: 155-160 (1992).
Imai et al., "New clinical tests: current status of tumor markers," Nihon Naika Gakkai Zasshi, 82(4):554-557 (Apr. 10, 1993).
Hisanao, "Clinical Significance of Tumor Markers," Jpn. J. Gastroenterol. Surg., 27(3): 743-752 (1994).
Avastin® (bevacizumab) Prescribing Information (last revised Dec. 2015).

(Continued)

Primary Examiner — Nelson B Moseley, II
(74) Attorney, Agent, or Firm — Neal, Gerber & Eisenberg LLP; Kevin A. O'Connor

(57) ABSTRACT

The present invention generally provides a therapy for effectively treating and/or preventing diseases associated with cells expressing CLDN18.2, in particular cancer diseases such as gastroesophageal cancer. Data are presented demonstrating that administration of an anti-CLDN18.2 antibody to human patients with gastroesophageal cancer is safe and well-tolerated up to a dose of at least 1000 mg/m². Furthermore, data are presented demonstrating that the antibody is fully functional in these patients to execute antitumor cell effects and evidence for antitumoral activity was obtained.

19 Claims, 16 Drawing Sheets

Specification includes a Sequence Listing.

(56) References Cited

FOREIGN PATENT DOCUMENTS

| | | | |
|---|---|---|---|
| EP | 1165784 | A2 | 1/2002 |
| EP | 1208202 | A2 | 5/2002 |
| EP | 1251863 | A1 | 10/2002 |
| EP | 1255766 | A2 | 11/2002 |
| EP | 1259526 | A2 | 11/2002 |
| EP | 1259614 | A2 | 11/2002 |
| EP | 1261703 | A1 | 12/2002 |
| EP | 1328635 | A2 | 7/2003 |
| EP | 1929003 | A2 | 6/2008 |
| EP | 1934378 | A2 | 6/2008 |
| EP | 1934615 | A2 | 6/2008 |
| EP | 1983002 | A2 | 10/2008 |
| EP | 2125034 | A2 | 12/2009 |
| EP | 1315743 | B1 | 11/2012 |
| JP | 2009-517354 | A | 4/2009 |
| JP | 2010-528075 | A | 8/2010 |
| JP | 2010528075 | | 8/2010 |
| WO | WO2000012708 | A2 | 3/2000 |
| WO | WO2000015659 | A2 | 3/2000 |
| WO | WO2000020447 | A2 | 4/2000 |
| WO | WO2000058473 | A2 | 10/2000 |
| WO | WO2000078961 | A1 | 12/2000 |
| WO | WO2001016318 | A2 | 3/2001 |
| WO | WO2001116318 | A2 | 3/2001 |
| WO | WO2001048192 | A1 | 7/2001 |
| WO | WO2001054708 | A1 | 8/2001 |
| WO | WO2001055314 | A2 | 8/2001 |
| WO | WO2001055318 | A2 | 8/2001 |
| WO | WO2001055326 | A2 | 8/2001 |
| WO | WO2001055367 | A1 | 8/2001 |
| WO | WO2001068848 | A2 | 9/2001 |
| WO | WO2001075067 | A2 | 10/2001 |
| WO | WO2001090357 | A1 | 11/2001 |
| WO | WO2002014499 | A2 | 2/2002 |
| WO | WO2002018576 | A2 | 3/2002 |
| WO | WO2002020569 | A2 | 3/2002 |
| WO | WO2004063355 | A2 | 7/2004 |
| WO | WO2006024283 | A2 | 3/2006 |
| WO | WO2007027867 | A2 | 3/2007 |
| WO | WO2007035676 | A2 | 3/2007 |
| WO | WO2007035690 | A2 | 3/2007 |
| WO | WO 2007/059997 | * 5/2007 | ............ C07K 16/30 |
| WO | WO 2007/059997 | A1 | 5/2007 |
| WO | WO2007059997 | A1 | 5/2007 |
| WO | WO2007090670 | A1 | 8/2007 |
| WO | WO2008013948 | A2 | 1/2008 |
| WO | WO2008013954 | A2 | 1/2008 |
| WO | WO2008095152 | A2 | 8/2008 |
| WO | WO 2008/145338 | A2 | 12/2008 |
| WO | WO2008145338 | A2 | 12/2008 |
| WO | WO2008152822 | A1 | 12/2008 |
| WO | WO2009037090 | A1 | 3/2009 |
| WO | WO2010141093 | A2 | 12/2010 |
| WO | WO 2013/174403 | A1 | 11/2013 |
| WO | WO 2013/174510 | A1 | 11/2013 |
| WO | WO 2014/127906 | A1 | 8/2014 |

OTHER PUBLICATIONS

Baselga, Pfister, et al., "Phase I studies of anti-epidermal growth factor receptor chimeric antibody C225 alone and in combination with cisplatin", J. Clin. Oncol., 18:904-914 (2000).
Erbitux® (cetuximab) Prescribing Information (last revised Oct. 2015).
Heiskala, et al., "The Roles of Claudin Superfamily Proteins in Paracellular Transport," Traffic, vol. 2, No. 2, pp. 92-98 (2001).
Herceptin (trastuzumab) Prescribing Information (last revised Mar. 2016).
Klamp, Thorsten, et al., "Highly Specific Auto-Antibodies against Claudin-18 Isoform 2 Induced by a Chimeric HBcAg Virus-Like Particle Vaccine Kill Tumor Cells and Inhibit the Growth of Lung Metastases", Cancer Research 2011; 71(2) (Jan. 15, 2011).
Magdelaine-Beuzelin et al., "IgG1 heavy chain-coding gene polymorphism (G1m allotypes) and development of antibodies-to-infliximab", Pharmacogenetics and Genomics, 19(5):383-387 (May 2009).
Meza-Junco et al., "Metastatic gastric cancer—focus on targeted therapies", Biologies: Targets and Therapy, 6:137-146 (2012).
Nacht, et al., "Combining Serial Analysis of Gene Expression and Array Technologies to Identify Genes Differentially Expressed in Breast Cancer," Cancer Research, vol. 59, No. 21, pp. 5464-5470 (1999).
National Cancer Institute, Equivalent Surface Area Dosage Conversion Factors, available at https://ncifrederick.cancer.gov/lasp/acuc/frederick/Media/Documents/ACUC42.pdf (retrieved Aug. 18, 2016).
Ross, et al., "Systematic Variation in Gene Expression Patterns in Human Cancer Cell Lines," Nature Genetics, vol. 24, No. 3, pp. 227-235 (2000).
Sahin, Ugur, et al., "Claudin-18 Splice Variant 2 Is a Pan-Cancer Target Suitable for Therapeutic Antibody Development", Clinical Cancer Research 2008; 14(23) (Dec. 1, 2008).
Spratlin et al., "Phase I pharmacologic and biologic study of ramucirumab (IMC-1121B), a fully human immunoglobulin G1 monoclonal antibody targeting the vascular endothelial growth factor receptor-2", J. Clin. Oncol., 28(5):780-787 (2010).
Tanaka, "Pathologic Studies on the Lesion of Gastric Cancer and the Distribution of its Metastases The Comparative Study Between Gastrectomied and Non-Gastrectomied Cases," Journal of the Showa Medical Association, vol. 23, No. 8, pp. 40-65 (1963).
Tobiani et al., "Feasibility and pharmacokinetic study of a chimeric anti-CD20 monoclonal antibody (IDEC-C2B8, rituximab) in relapsed B-cell lymphoma. The IDEC-C2B8 Study Group", Annals of Oncology, 9(5):527-534 (1998).
Yagi, et al., "A Case of Krukenberg's Tumor," Advances in Obstetrics and Gynecology, vol. 11, No. 4, pp. 324-326 (1959).
U.S. Appl. No. 10/537,002, 2006/0035852, U.S. Pat. No. 7,527,933.
U.S. Appl. No. 12/326,997, 2009/0155817, U.S. Pat. No. 8,088,588.
U.S. Appl. No. 12/423,153, 2009/0208498, U.S. Pat. No. 8,586,047.
U.S. Appl. No. 13/296,620, 2012/0258091, U.S. Pat. No. 8,637,012.
U.S. Appl. No. 14/043,109, 2014/0186338, abandoned.
U.S. Appl. No. 14/821,411, 2015/0337052, abandoned.
U.S. Appl. No. 15/650,092, 2017/0320963, U.S. Pat. No. 10,414,824.
U.S. Appl. No. 11/596,649, 2008/0166350, U.S. Pat. No. 9,044,382.
U.S. Appl. No. 14/676,254, 2015/0315287, U.S. Pat. No. 9,775,785.
U.S. Appl. No. 15/448,831, 2017/0215536, pending.
U.S. Appl. No. 12/094,530, 2009/0169547, U.S. Pat. No. 8,168,427.
U.S. Appl. No. 13/306,545, 2012/0164160, U.S. Pat. No. 9,499,609.
U.S. Appl. No. 13/425,538, 2012/0195830, U.S. Pat. No. 9,212,228.
U.S. Appl. No. 14/661,882, 2015/0252104, U.S. Pat. No. 9,751,934.
U.S. Appl. No. 14/661,846, 2015/0252103, U.S. Pat. No. 10,174,104.
U.S. Appl. No. 15/069,511, 2016/0185860, U.S. Pat. No. 10,017,564.
U.S. Appl. No. 15/710,252, 2018/0127489, pending.
U.S. Appl. No. 12/601,488, 2010/0166779, U.S. Pat. No. 8,425,902.
U.S. Appl. No. 14/397,244, 2015/0147763, U.S. Pat. No. 9,512,232.
U.S. Appl. No. 15/227,565, 2016/0333109, U.S. Pat. No. 10,053,512.
U.S. Appl. No. 14/401,899, 2015/0132253, abandoned.
U.S. Appl. No. 14/401,557, 2015/0157711, U.S. Pat. No. 9,433,675.
U.S. Appl. No. 15/231,185, 2016/0339101, U.S. Pat. No. 10,022,444.
U.S. Appl. No. 14/442,445, 2016/0272711, U.S. Pat. No. 10,093,736.
U.S. Appl. No. 14/769,046, 2015/0374789, U.S. Pat. No. 9,770,487.
U.S. Appl. No. 15/684,168, 2018/0000900, U.S. Pat. No. 10,314,890.
U.S. Appl. No. 14/777,231, 2016/0008465, U.S. Pat. No. 10,137,195.
U.S. Appl. No. 15/565,848, 2018/0117174, pending.
U.S. Appl. No. 16/158,187, 2019/0076525, Pending.
U.S. Appl. No. 15/973,116, 2018/0326059, Pending.
U.S. Appl. No. 15/909,577, 2018/0258180, pending.

* cited by examiner

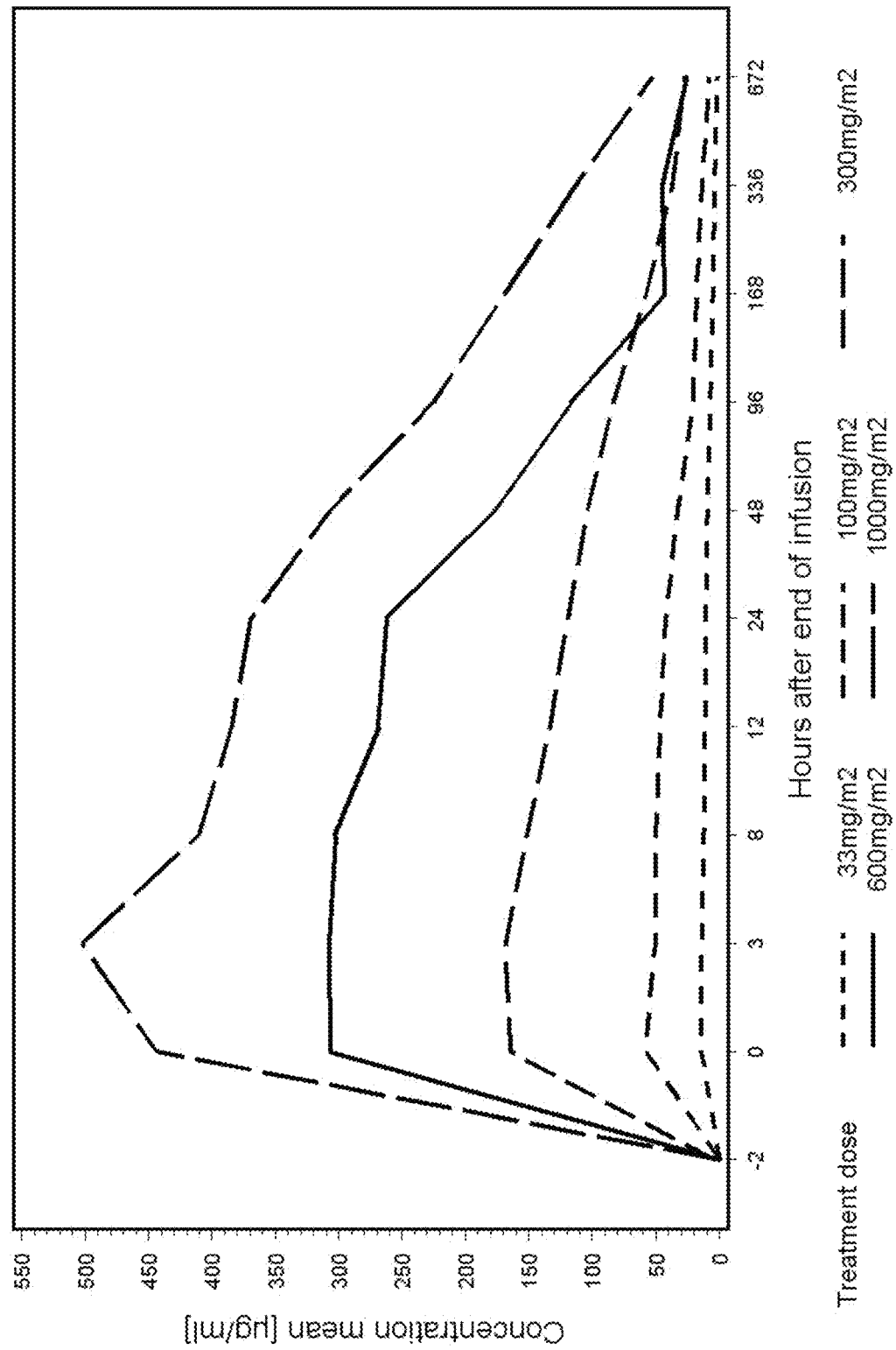

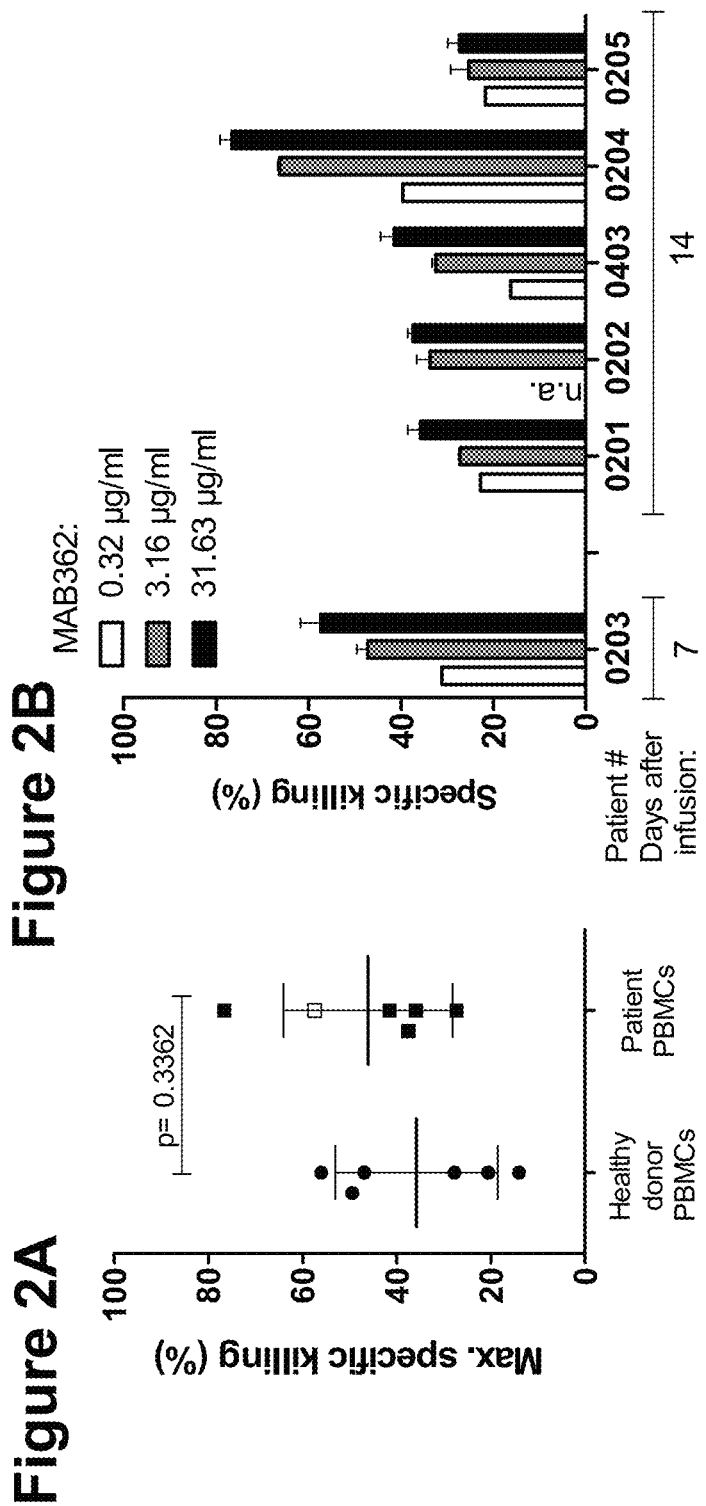

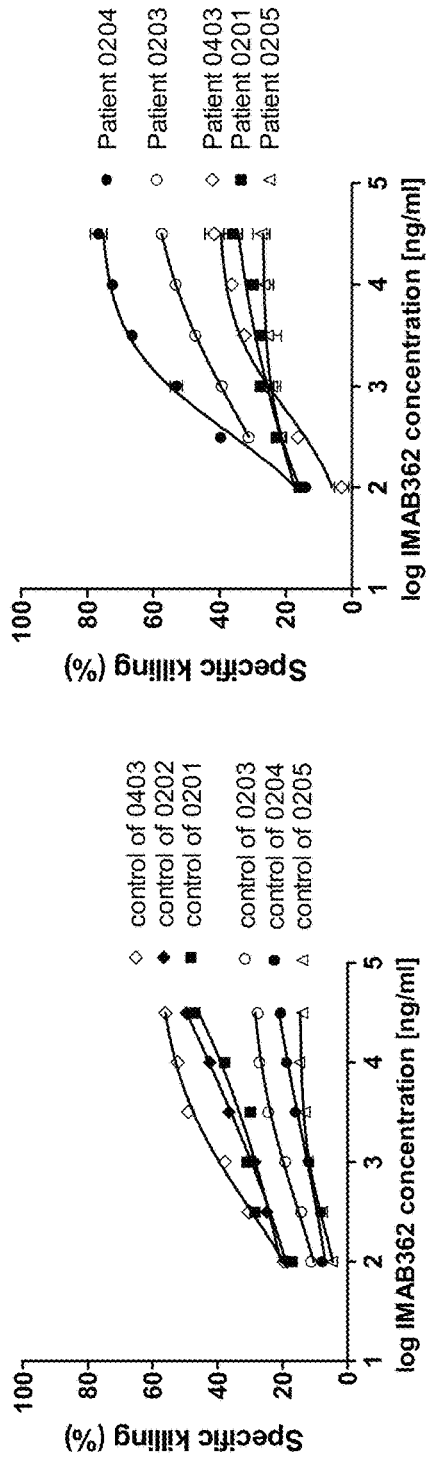
Figure 2D
Figure 2C
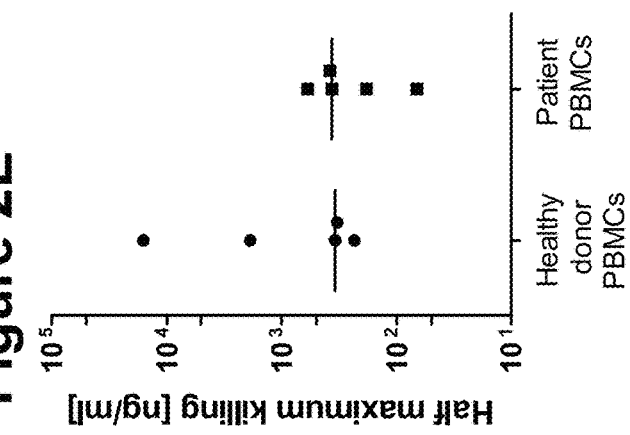
Figure 2E

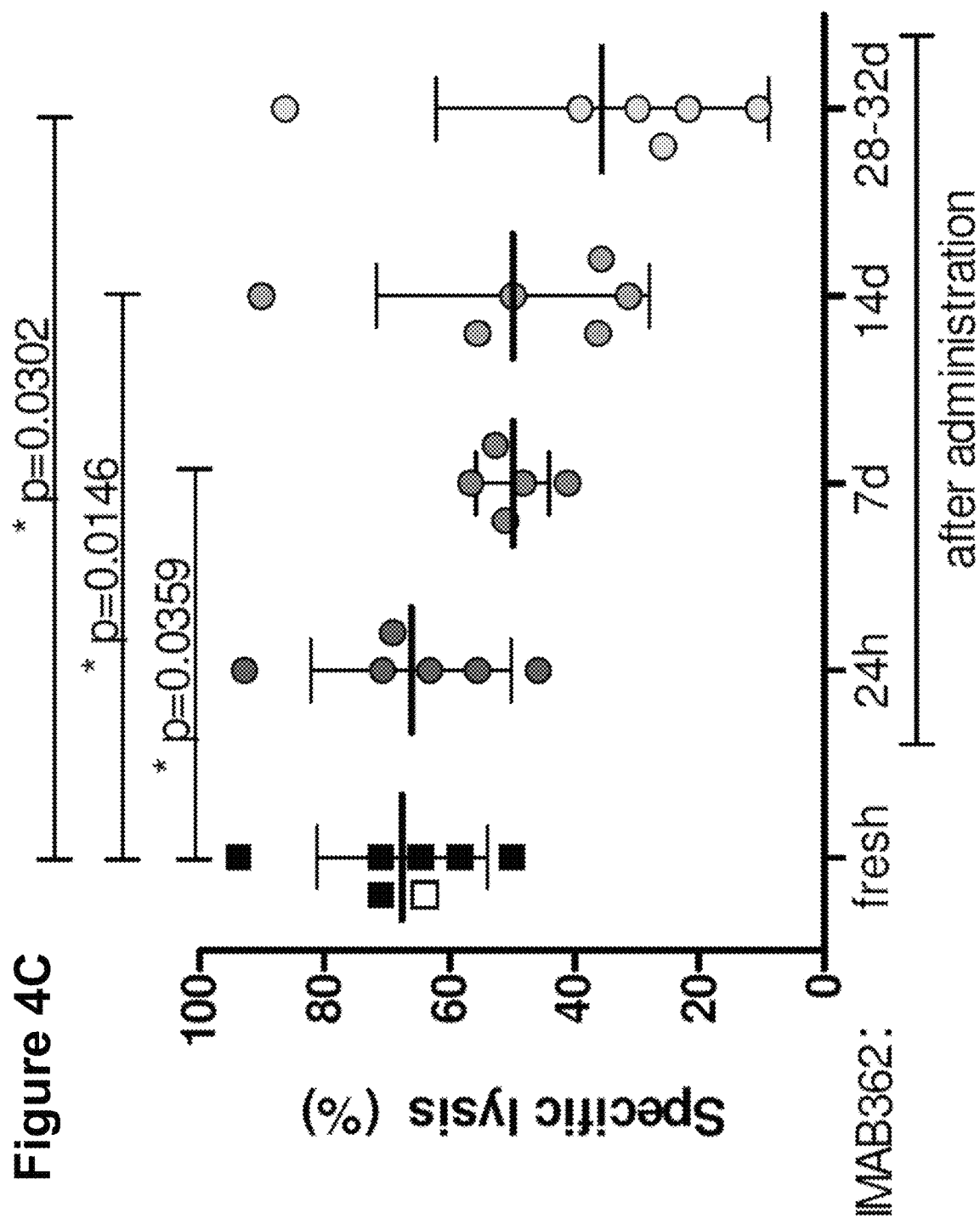

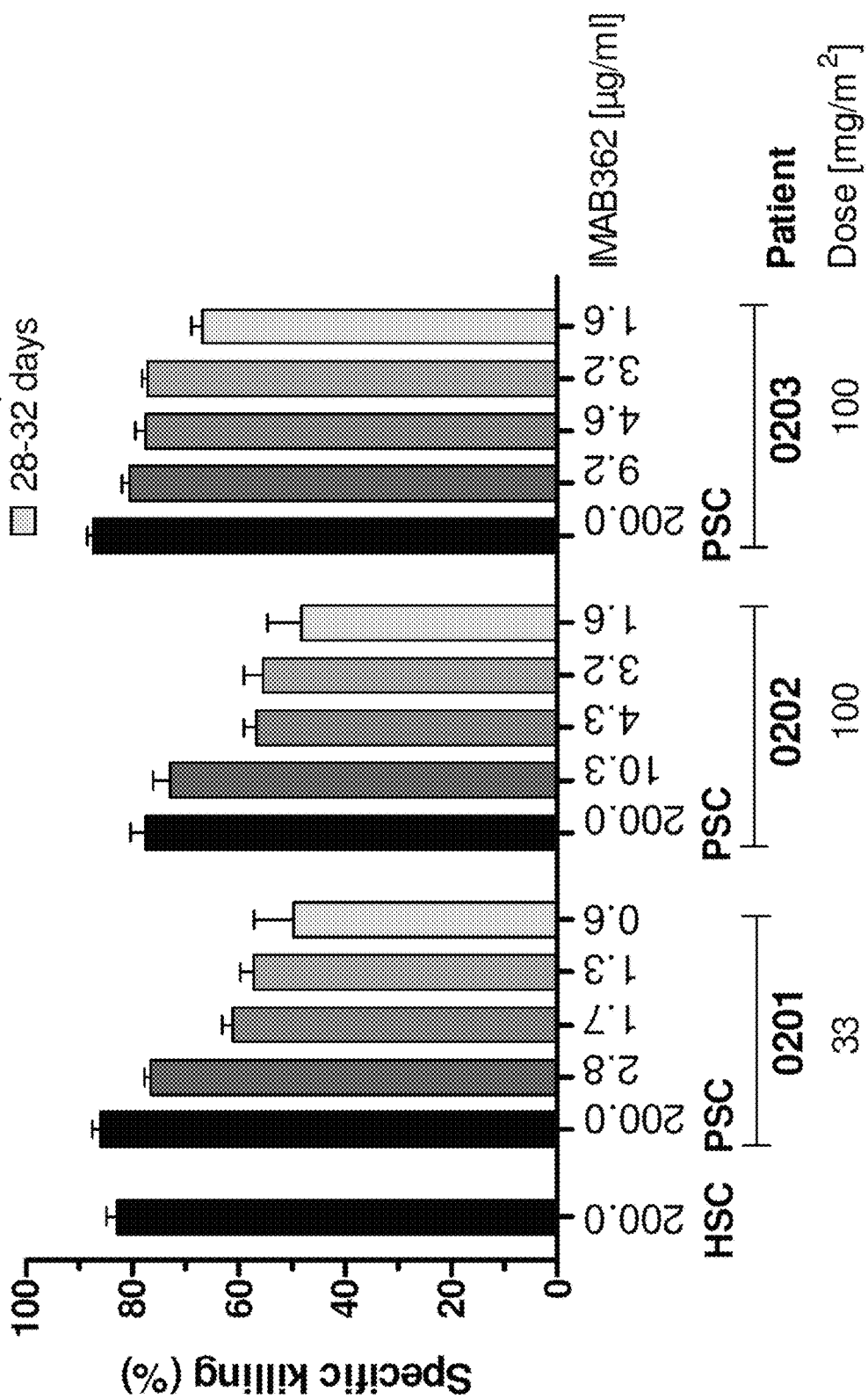

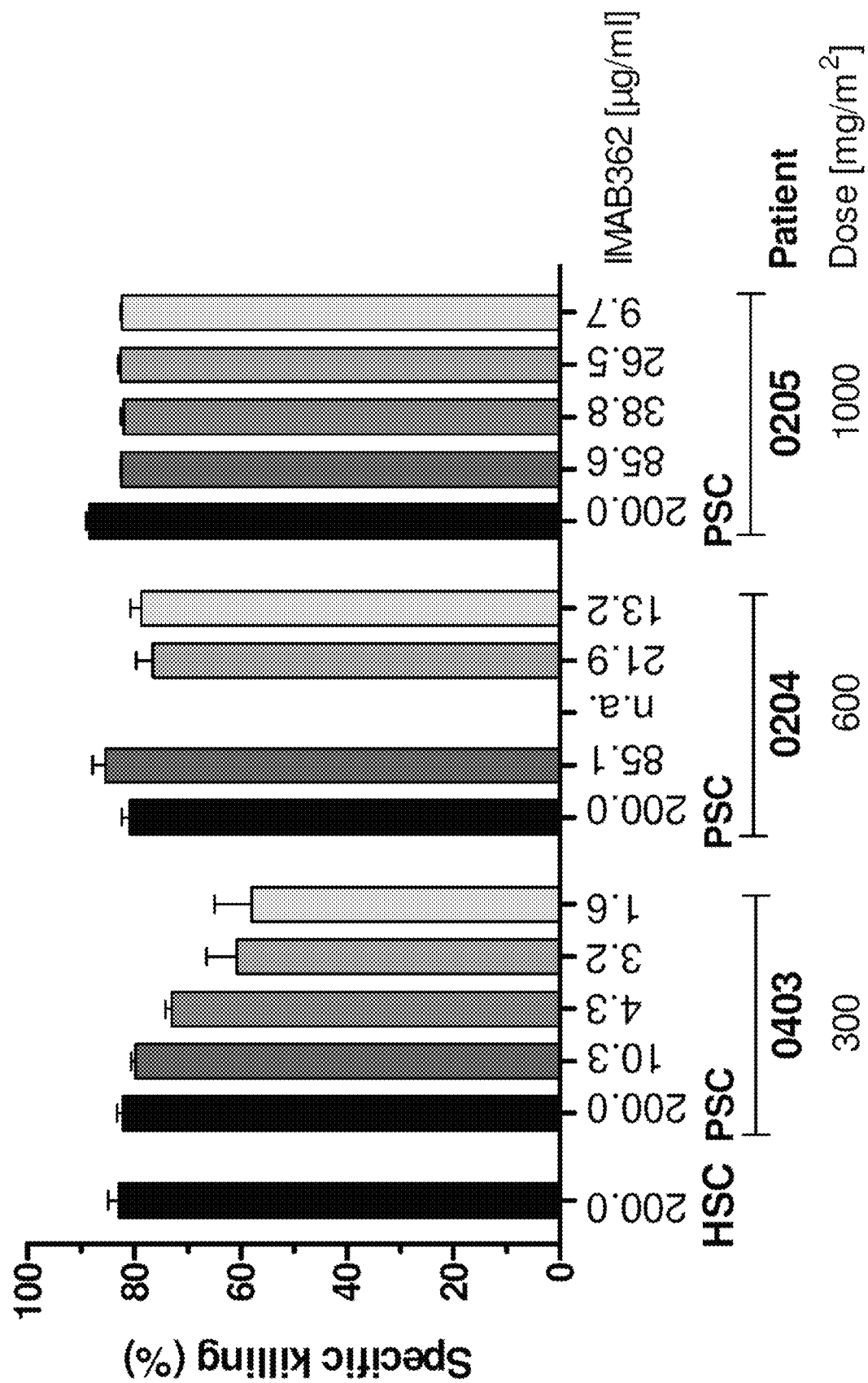

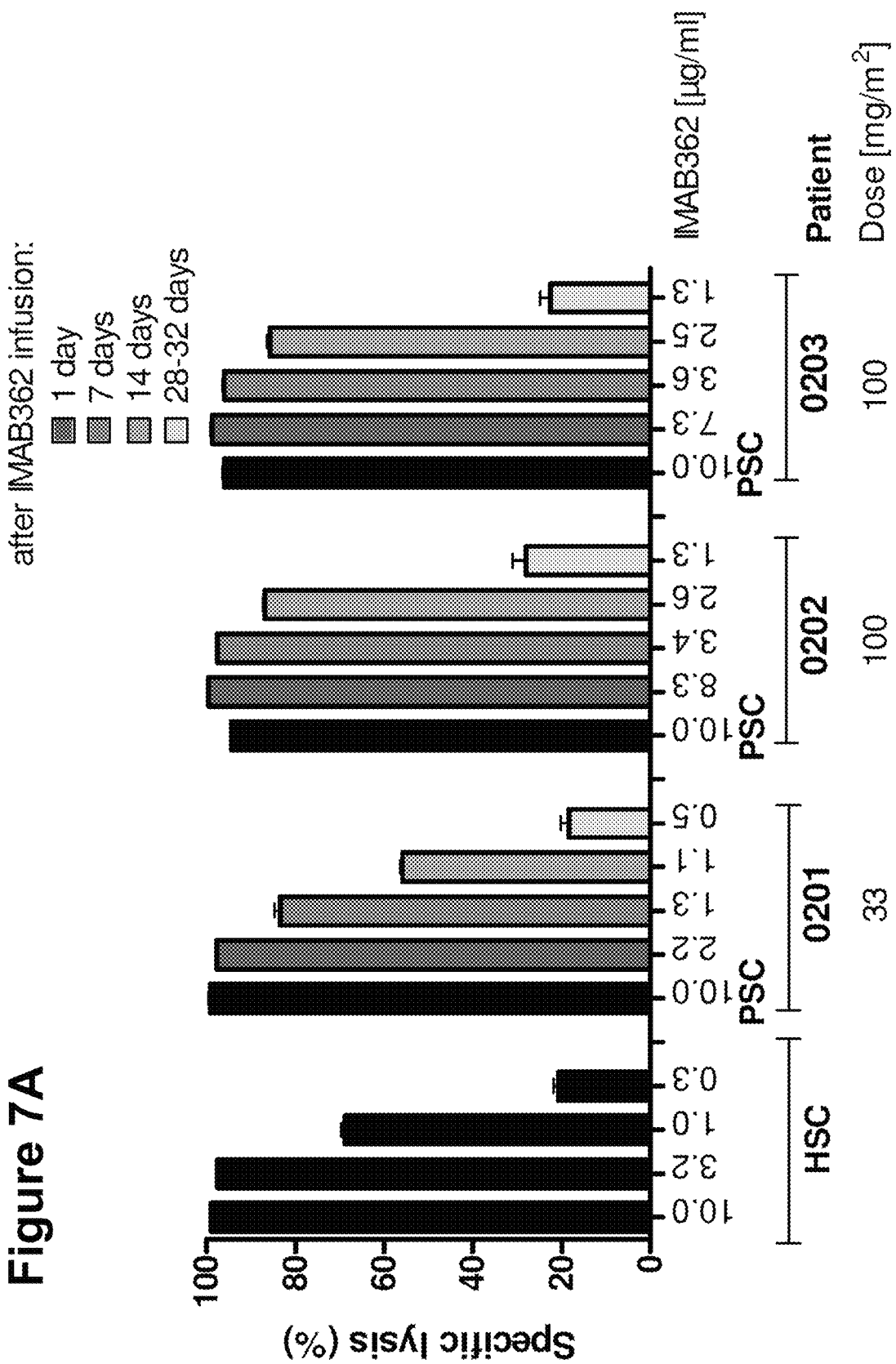

THERAPY INVOLVING ANTIBODIES AGAINST CLAUDIN 18.2 FOR TREATMENT OF CANCER

CROSS-REFERENCE TO RELATED APPLICATIONS

This application is a continuation of U.S. application Ser. No. 14/777,231, filed on Sep. 15, 2015 as a national stage entry of international application PCT/EP2014/000719, filed on Mar. 17, 2014, which claimed priority to international application PCT/EP2013/000817, filed on Mar. 18, 2013. The entire contents of each of the aforementioned applications are incorporated herein by reference.

BACKGROUND

Cancers of the stomach and the esophagus (gastroesophageal; GE) are among the malignancies with the highest unmet medical need. Gastric cancer is the second leading cause of cancer death worldwide. The incidence of esophageal cancer has increased in recent decades, coinciding with a shift in histological type and primary tumor location. Adenocarcinoma of the esophagus is now more prevalent than squamous cell carcinoma in the United States and Western Europe, with most tumors located in the distal esophagus. The overall five-year survival rate for GE cancer is 20-25%, despite the aggressiveness of established standard treatment associated with substantial side effects.

The majority of patients presents with locally advanced or metastatic disease and have to be subjected to first-line chemotherapy. Treatment regimens are based on a backbone of platinum and fluoropyrimidine derivatives mostly combined with a third compound (e.g. taxane or anthracyclines). Still, median progression free survival of 5 to 7 months and median overall survival of 9 to 11 months are the best that can be expected.

The lack of a major benefit from the various newer generation combination chemotherapy regimens for these cancers has stimulated research into the use of targeted agents. Recently, for Her2/neu-positive gastroesophageal cancers Trastuzumab has been approved. However, as only ~20% of patients express the target and are eligible for this treatment, the medical need is still high.

The tight junction molecule Claudin 18 splice variant 2 (Claudin 18.2 (CLDN18.2)) is a member of the claudin family of tight junction proteins. CLDN18.2 is a 27.8 kDa transmembrane protein comprising four membrane spanning domains with two small extracellular loops.

In normal tissues there is no detectable expression of CLDN18.2 by RT-PCR with exception of stomach. Immunohistochemistry with CLDN18.2 specific antibodies reveals stomach as the only positive tissue.

CLDN18.2 is a highly selective gastric lineage antigen expressed exclusively on short-lived differentiated gastric epithelial cells. CLDN18.2 is maintained in the course of malignant transformation and thus frequently displayed on the surface of human gastric cancer cells. Moreover, this pan-tumoral antigen is ectopically activated at significant levels in esophageal, pancreatic and lung adenocarcinomas. The CLDN18.2 protein is also localized in lymph node metastases of gastric cancer adenocarcinomas and in distant metastases especially into the ovary (so-called Krukenberg tumors).

The chimeric IgG1 antibody IMAB362 which is directed against CLDN18.2 has been developed by Ganymed Pharmaceuticals AG. IMAB362 recognizes the first extracellular domain (ECD1) of CLDN18.2 with high affinity and specificity. IMAB362 does not bind to any other claudin family member including the closely related splice variant 1 of Claudin 18 (CLDN18.1). IMAB362 shows precise tumor cell specificity and bundles four independent highly potent mechanisms of action. Upon target binding IMAB362 mediates cell killing by ADCC, CDC and induction of apoptosis induced by cross linking of the target at the tumor cell surface and direct inhibition of proliferation. Thus, IMAB362 lyses efficiently CLDN18.2-positive cells, including human gastric cancer cell lines in vitro and in vivo. Mice bearing CLDN18.2-positive cancer cell lines have a survival benefit and up to 40% of mice show regression of their tumor when treated with IMAB362.

The toxicity and PK/TK profile of IMAB362 has been thoroughly examined in mice and cynomolgus monkeys including dose range finding studies, 28-day repeated dose toxicity studies in cynomolgus and a 3-month repeated dose toxicity study in mice. In both mice (longest treatment duration weekly administration for 3 months, highest dose levels 400 mg/kg) and cynomolgus monkeys (up to 5 weekly applications of up to 100 mg/kg) repeated doses of IMAB362 i.v. are well tolerated. No signs of systemic or local toxicity are induced. Specifically, no gastric toxicity has been observed in any toxicity study. IMAB362 does not induce immune activation and cytokine release. No adverse effects on male or female reproductive organs were recorded. IMAB362 does not bind to tissues lacking the target. Biodistribution studies in mice indicate that the reason for lack of gastric toxicity is most likely compartimentalization of tight junctions at the luminal site in healthy gastric epithelia, which appears to impair accessibility of the IMAB362 epitope profoundly. This compartimentalization is lost upon malignant transformation rendering the epitope druggable by IMAB362.

Here we present data demonstrating that administration of an anti-CLDN18.2 antibody such as IMAB362 to human patients with gastroesophageal cancer is safe and well-tolerated up to a dose of at least 1000 mg/m$^2$. Furthermore, the data presented herein demonstrate that the antibody is fully functional in these patients to execute anti-tumor cell effects and evidence for antitumoral activity was obtained.

SUMMARY OF THE INVENTION

The present invention generally provides a therapy for effectively treating and/or preventing diseases associated with cells expressing CLDN18.2, including cancer diseases such as gastric cancer, esophageal cancer, pancreatic cancer, lung cancer such as non small cell lung cancer (NSCLC), ovarian cancer, colon cancer, hepatic cancer, head-neck cancer, and cancer of the gallbladder and metastases thereof, in particular gastric cancer metastasis such as Krukenberg tumors, peritoneal metastasis and lymph node metastasis. Particularly preferred cancer diseases are adenocarcinomas of the stomach, the esophagus, the pancreatic duct, the bile ducts, the lung and the ovary.

In a first aspect, the present invention provides a method of treating or preventing a cancer disease comprising administering to a patient an antibody having the ability of binding to CLDN18.2, wherein the antibody is administered so as to provide a serum level of at least 40 µg/ml. In different embodiments, the antibody is administered so as to provide a serum level of at least 50 µg/ml, at least 150 µg/ml, at least 300 µg/ml, at least 400 µg/ml or at least 500 µg/ml. In different embodiments, the antibody is administered so as to provide a serum level of not more than 800 µg/ml, 700

µg/ml, 600 µg/ml, 550 µg/ml or 500 µg/ml. In one embodiment, the serum level provided is between 40 µg/ml and 700 µg/ml, preferably 40 µg/ml and 600 µg/ml, preferably 50 µg/ml and 500 µg/ml such as between 150 µg/ml and 500 µg/ml or 300 µg/ml and 500 µg/ml. By the term "serum level", as used in the present specification, it is meant a concentration of the substance in question in the blood serum. In one embodiment, the serum level is provided for at least 7 days or at least 14 days. In one embodiment, the method comprises administering a dose/doses of the antibody of at least 300 mg/m$^2$ such as at least 600 mg/m$^2$ and preferably up to 1500 mg/m$^2$, up to 1200 mg/m$^2$ or up to 1000 mg/m$^2$.

In a second aspect, the present invention provides a method of treating or preventing a cancer disease comprising administering to a patient an antibody having the ability of binding to CLDN18.2, wherein the antibody is administered at a dose of at least 300 mg/m$^2$ such as at least 600 mg/m$^2$ and preferably up to 1500 mg/m$^2$, up to 1200 mg/m$^2$ or up to 1000 mg/m$^2$.

In a third aspect, the present invention provides a method of treating or preventing a cancer disease comprising administering to a patient an antibody having the ability of binding to CLDN18.2, wherein at least 50%, preferably 60%, 70%, 80% or 90% of the cancer cells of the patient are CLDN18.2 positive and/or at least 40%, preferably 50% or 60% of the cancer cells of the patient are positive for surface expression of CLDN18.2. In this aspect, the present invention also provides a method of treating or preventing a cancer disease, said method comprising: a. identifying a patient exhibiting at least 50%, preferably 60%, 70%, 80% or 90% CLDN18.2 positive cancer cells and/or at least 40%, preferably 50% or 60% cancer cells which are positive for surface expression of CLDN18.2; and b. administering to said patient an antibody having the ability of binding to CLDN18.2. In one embodiment, at least 95% or at least 98% of the cancer cells of the patient are CLDN18.2 positive. In one embodiment, at least 70%, at least 80% or at least 90% of the cancer cells of the patient are positive for surface expression of CLDN18.2.

In one embodiment of the method of any of the aspects described herein, treatment of the cancer disease results in achieving stable disease. In one embodiment, stable disease is achieved for at least 2 months, at least 3 months or at least 6 months.

In a fourth aspect, the present invention provides a method of achieving stable disease in a cancer patient comprising administering to the patient an antibody having the ability of binding to CLDN18.2. In one embodiment, stable disease is achieved for at least 2 months, at least 3 months or at least 6 months.

In one embodiment of the method of any of the aspects described herein, the antibody is administered in a single dose or in multiple doses.

In a fifth aspect, the present invention provides a method of treating or preventing a cancer disease comprising administering to a patient an antibody having the ability of binding to CLDN18.2, wherein the antibody is administered in multiple doses.

If according to the invention the antibody is administered in multiple doses, the antibody is preferably administered in at least 3 doses, at least 4 doses, at least 5 doses, at least 6 doses, at least 7 doses, at least 8 doses, at least 9 doses or at least 10 doses and preferably up to 30, 25, 20, 15 or 10 doses. The doses of the antibody are preferably administered in time intervals of at least 7 days, at least 10 days, at least 14 days, or at least 20 days. The doses of the antibody are preferably administered in time intervals of between 7 and 30 days, 10 and 20 days and preferably about 14 days.

In one embodiment of the method of the third, fourth or fifth aspect, the antibody is administered so as to provide a serum level of at least 40 µg/ml. In different embodiments, the antibody is administered so as to provide a serum level of at least 50 µg/ml, at least 150 µg/ml, at least 300 µg/ml, at least 400 µg/ml or at least 500 µg/ml. In different embodiments, the antibody is administered so as to provide a serum level of not more than 800 µg/ml, 700 µg/ml, 600 µg/ml, 550 µg/ml or 500 µg/ml. In one embodiment, the serum level provided is between 40 µg/ml and 700 µg/ml, preferably 40 µg/ml and 600 µg/ml, preferably 50 µg/ml and 500 µg/ml such as between 150 µg/ml and 500 µg/ml or 300 µg/ml and 500 µg/ml. In one embodiment, the serum level is provided for at least 7 days or at least 14 days. In one embodiment, the method comprises administering a dose/doses of the antibody of at least 300 mg/m$^2$ such as at least 600 mg/m$^2$ and preferably up to 1500 mg/m$^2$, up to 1200 mg/m$^2$ or up to 1000 mg/m$^2$.

In one embodiment of the method of any of the above aspects, the method further comprises administering one or more selected from the group consisting of antiemetics, antispasmodics, parasympatholytics and agents which protect gastric mucosa.

In a sixth aspect, the present invention provides a method of treating or preventing a cancer disease comprising administering to a patient an antibody having the ability of binding to CLDN18.2 and one or more selected from the group consisting of antiemetics, antispasmodics, parasympatholytics and agents which protect gastric mucosa.

If the method of the invention comprises administering one or more selected from the group consisting of antiemetics, antispasmodics, parasympatholytics and agents which protect gastric mucosa, the method in different embodiments comprises administering: (i) an antiemetic and an antispasmodic, (ii) an antispasmodic and an agent which protects gastric mucosa, (iii) an antiemetic and an agent which protects gastric mucosa or (iv) an antiemetic, an antispasmodic and an agent which protects gastric mucosa.

In one embodiment, an antiemetic is administered as antiemetic prophylaxis prior to administration of the antibody. In one embodiment, an antiemetic is administered as antiemetic intervention simultaneously with and/or following administration of the antibody. In one embodiment, the antiemetic comprises a 5-HT3 receptor antagonist and/or a neurokinin 1 (NK1) receptor antagonist. Preferably, the NK1 receptor antagonist comprises Aprepitant (e.g. Emend) and the 5-HT3 receptor antagonist comprises Ondansetron (e.g. Zofran), Granisetron (e.g. Kytril, Sancuso) or Palonosetron (e.g. Aloxi), or a combination of two or more thereof.

In one embodiment, the antispasmodic comprises butylscopolamine (Buscopan).

In one embodiment, the agent which protects gastric mucosa comprises an agent which reduces production of gastric acid. In one embodiment, the agent which protects gastric mucosa comprises an agent selected from the group consisting of proton pump inhibitors, Misoprostol and Omeprazole. In one embodiment, the agent which protects gastric mucosa comprises a combination of a proton pump inhibitor and Misoprostol. In one embodiment, the proton pump inhibitor comprises Pantoprazole (e.g. Pantozol).

In one embodiment, the method of the invention comprises administering to the patient a NK1 receptor antagonist such as Aprepitant (e.g. Emend), a 5-HT3 receptor antagonist such as Ondansetron (e.g. Zofran), Granisetron (e.g. Kytril, Sancuso) or Palonosetron (e.g. Aloxi), or a combination of two or more thereof, an antispasmodic such as butylscopolamine (e.g. Buscopan) and a proton pump inhibitor such as Pantoprazole (e.g. Pantozol).

In one embodiment of the method of any of the above aspects, the antibody is administered by i.v. infusion. In one embodiment, the i.v. infusion is over a time period of between 1 and 4 hours, preferably about 2 hours.

In a sixth aspect, the present invention provides a method of determining the responsiveness of a cancer patient to treatment or prevention of a cancer disease comprising administering an antibody having the ability of binding to CLDN18.2, said method comprising the step of determining the blood level of one or more markers in the patient, wherein the one or more markers are selected from the group consisting of CA 125, CA 15-3, CA 19-9, CEA, IL-2, IL-15, IL-6, IFNγ, and TNFα. In this aspect, prior to and following administration of an antibody having the ability of binding to CLDN18.2, such as following administration of a single dose of the antibody, biological samples such as blood may be taken from the patient to establish the level of the one or more markers. Multiple samples may be taken from the same tissue to determine average levels and to account for possible fluctuations in those levels. The level of the one or more markers following administration of the antibody is compared with the level determined prior to administration. The effect of the antibody on the patient can therefore be identified by a desired change in the level of marker following administering an antibody having the ability of binding to CLDN18.2. If the patient shows a desired change in the level of marker following administering an antibody having the ability of binding to CLDN18.2 treatment with the antibody having the ability of binding to CLDN18.2 may be commenced.

In one embodiment, the level is determined in blood, plasma or serum.

In one embodiment, the one or more markers are selected from the group consisting of CA 125, CA 15-3, CA 19-9, CEA, IL-2, IL-15, IFNγ, and TNFα and a decrease in the level of at least one of the markers following administration of the antibody indicates that the patient is responsive to treatment or prevention of a cancer disease.

In one embodiment, the marker is IL-6 and an increase in the level of the marker following administration of the antibody indicates that the patient is responsive to treatment or prevention of a cancer disease.

In an eighth aspect, the present invention provides a method of determining whether a cancer patient is amenable to treatment or prevention of a cancer disease comprising administering an antibody having the ability of binding to CLDN18.2, said method comprising the step of determining the percentage of CLDN18.2 positive cancer cells.

In this embodiment, prior to administration of an antibody having the ability of binding to CLDN18.2, a biological sample such as a tumor sample (e.g. a tumor biopsy) may be taken from the patient to establish the level of CLDN18.2 positive cancer cells. Multiple samples may be taken to determine an average level and to account for possible fluctuations in those levels. If a patient has the desired level of CLDN18.2 positive cancer cells an antibody having the ability of binding to CLDN18.2 may be administered.

In one embodiment, a level of at least 50%, preferably 60%, 70%, 80% or 90%, at least 95% or at least 98% CLDN18.2 positive cancer cells indicates that the patient is amenable to treatment or prevention of a cancer disease. In one embodiment, a level of at least 40%, preferably at least 50%, at least 60%, at least 70%, at least 80% or at least 90% cancer cells which are positive for surface expression of CLDN18.2 indicates that the patient is amenable to treatment or prevention of a cancer disease.

The antibody having the ability of binding to CLDN18.2 may bind to native epitopes of CLDN18.2 present on the surface of living cells. In one embodiment, the antibody having the ability of binding to CLDN18.2 binds to the first extracellular loop of CLDN18.2. In one embodiment, the antibody having the ability of binding to CLDN18.2 mediates cell killing by one or more of complement dependent cytotoxicity (CDC) mediated lysis, antibody dependent cellular cytotoxicity (ADCC) mediated lysis, induction of apoptosis and inhibition of proliferation. In one embodiment, the antibody having the ability of binding to CLDN18.2 is a monoclonal, chimeric or humanized antibody, or a fragment of an antibody. In one embodiment, the antibody having the ability of binding to CLDN18.2 is an antibody selected from the group consisting of (i) an antibody produced by and/or obtainable from a clone deposited under the accession no. DSM ACC2737, DSM ACC2738, DSM ACC2739, DSM ACC2740, DSM ACC2741, DSM ACC2742, DSM ACC2743, DSM ACC2745, DSM ACC2746, DSM ACC2747, DSM ACC2748, DSM ACC2808, DSM ACC2809, or DSM ACC2810, (ii) an antibody which is a chimerized or humanized form of the antibody under (i), (iii) an antibody having the specificity of the antibody under (i), and (iv) an antibody comprising the antigen binding portion or antigen binding site, in particular the variable region, of the antibody under (i) and preferably having the specificity of the antibody under (i). In one embodiment, the antibody is coupled to a therapeutic agent such as a toxin, a radioisotope, a drug or a cytotoxic agent.

In one embodiment, the cancer is CLDN18.2 positive. In one embodiment, cells of the cancer express CLDN18.2. In one embodiment, expression of CLDN18.2 is at the surface of the cells. In one embodiment, at least 50%, preferably 60%, 70%, 80% or 90% of the cancer cells are CLDN18.2 positive and/or at least 40%, preferably at least 50% of the cancer cells are positive for surface expression of CLDN18.2. In one embodiment, at least 95% or at least 98% of the cancer cells are CLDN18.2 positive. In one embodiment, at least 60%, at least 70%, at least 80% or at least 90% of the cancer cells are positive for surface expression of CLDN18.2.

In one embodiment, the cancer disease is selected from the group consisting of gastric cancer, esophageal cancer, pancreatic cancer, lung cancer, ovarian cancer, colon cancer, hepatic cancer, head-neck cancer, cancer of the gallbladder and the metastasis thereof. The cancer disease may be a Krukenberg tumor, peritoneal metastasis and/or lymph node metastasis. In one embodiment, the cancer is an adenocarcinoma, in particular an advanced adenocarcinoma. In one embodiment, the cancer is selected from the group consisting of cancer of the stomach, cancer of the esophagus, in particular the lower esophagus, cancer of the eso-gastric junction and gastroesophageal cancer. In a particularly preferred embodiment, the cancer is gastroesophageal cancer such as metastatic, refractory or recurrent advanced gastroesophageal cancer. The patient may be a HER2/neu negative patient or a patient with HER2/neu positive status but not eligible to trastuzumab therapy. In one embodiment, the patient had prior therapy with at least one drug selected from the group consisting of pyrimidine analogs (e.g. fluorouracil and/or capecitabine), platinum compounds (e.g. cisplatin and/or oxaliplatin), epirubicine, docetaxel and detoxifying agents for antineoplastic treatment (e.g. calcium folinate and/or folinic acid). In one embodiment, the patient has an ECOG performance status of between 0 and 1 and/or a Karnofsky Index of between 70 and 100%. In a particularly preferred embodiment, the patient is a human patient According to the invention, CLDN18.2 preferably has the amino acid sequence according to SEQ ID NO: 1.

The present invention also provides the agents described herein such as the antibody having the ability of binding to CLDN18.2 for use in the methods described herein.

Other features and advantages of the instant invention will be apparent from the following detailed description and claims.

BRIEF DESCRIPTION OF THE DRAWINGS

FIG. 1 shows mean blood concentration of IMAB362 during the study.

FIGS. 2A, 2B, 2C, 2D, and 2E show ADCC activity of patient PBMCs. (FIG. 2A) PBMCs were purified from 6 patient blood samples 7 days (open square) or 14 days (black squares) after IMAB362 administration. Specific lysis rates of NUGC-4 stomach cancer target cells, expressing CLDN18.2, obtained after addition of 31.63 µg/ml IMAB362 and PBMCs from a healthy donor or patient PBMCs (E:T=20:1) for 24 h. (FIG. 2B) IMAB362 concentration-dependent specific lysis of NUGC-4 cells obtained 24 h after addition of PBMCs of different patients (graphs display means±standard deviation, p value was calculated using unpaired t-test). (FIG. 2C) ADCC response curves of healthy control PBMCs upon addition of increasing IMAB362 concentrations. Assays were performed in parallel to each ADCC analysis with patient PBMCs. (FIG. 2D) ADCC response curve of patient PBMCs upon addition of increasing IMAB362 concentrations (for patient 0202 not enough PBMCs were obtained to generate a curve). (FIG. 2E) Half maximum killing rates for all patients and healthy donors was calculated with GraphPad Prism software using the build-in non-linear regression analysis tool.

FIGS. 4A, 4B, and 4C show ability of patient complement components to interact with i.v. administered IMAB362 over time. Normalized CDC assays were performed by adjusting the IMAB362 concentration in each sample to 0.5 µg/ml using pre-infusion serum of each patient (dilution factor 10-680 fold). (FIGS. 4A and 4B) CDC assays were performed as described in FIG. 3. (FIG. 4C) Each dot represents one patient measurement. Open square: 0.5 µg/ml IMAB362 in human serum. P values obtained with paired t-test. Error bars: mean±standard deviation.

FIGS. 5A and 5B show kinetics of cytotoxicity induced by i.v. administered circulating IMAB362. NUGC-4 target cells, PBMCs of one healthy donor (E:T=40:1) and patient serum samples (25% v/v) as antibody and complement source were used in a total cytotoxicity assay to measure integrated cytotoxic activity. Of each patient, serum samples were collected 1, 7, 14 and 28-32 days after IMAB362 administration. Patients were treated with escalating doses of IMAB362 (33-1000 mg/m²). The antibody concentration present in the assay is indicated below each bar. HSC: Human serum pool control spiked with fresh 200.0 µg/ml IMAB362 ($EC_{80-100}$). PSC: Patient pre-infusion serum control spiked with fresh 200.0 µg/ml IMAB362). n.a.: not available.

FIGS. 7A and 7B show CDC activity induced by IMAB362 present in patient serum. CDC assays were performed with CLDN18.2 and luciferase positive CHO-K1 target cells. They were incubated for 80 min with 20% (v/v) patient serum obtained 1, 7, 14 and 28-32 days after antibody infusion. Patients were treated with a IMAB362 dose of 33 to 1000 mg/m². The antibody concentration present in each assay is indicated below each bar. HSC: Healthy human serum pool control spiked with decreasing concentrations of IMAB362 as indicated. PC: positive control (patient pre-infusion serum spiked with 10 µg/ml IMAB362).

DETAILED DESCRIPTION OF THE INVENTION

Figure 3:
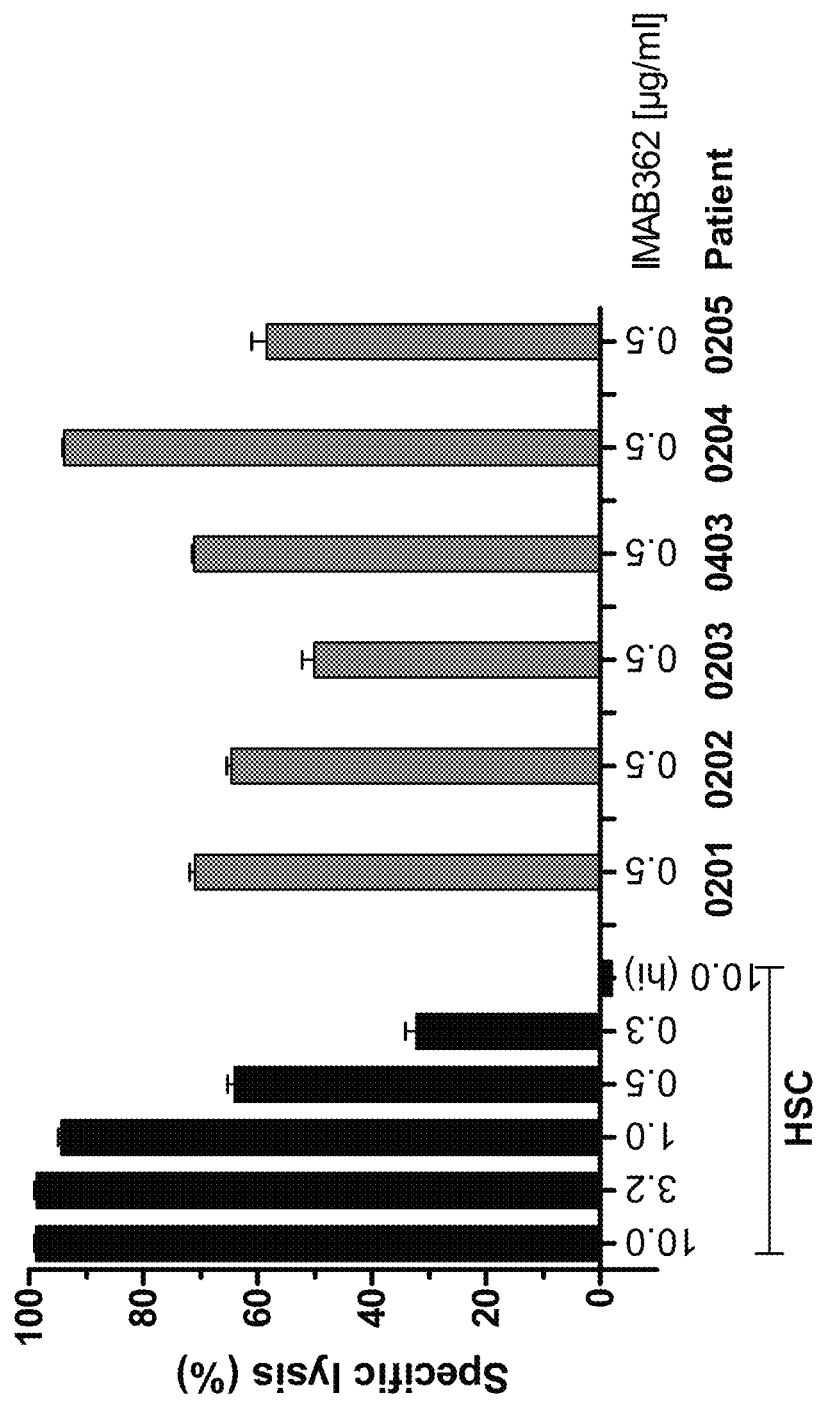
FIG. 3 shows ability of patient complement components to induce IMAB362-mediated CDC. CDC assays were performed with CLDN18.2 and luciferase positive CHO-K1 target cells. Cells, serum (20% v/v) and antibodies were incubated for 80 min at 37° C. Patient samples were prepared by addition of fresh 0.5 µg/ml IMAB362 in pre-infusion serum samples (grey bars). HSC: Healthy human serum pool control spiked with 0.3-10 µg/ml IMAB362 (positive control). Hi: Heat inactivated human serum pool spiked with 10 µg/ml IMAB362 (negative control). Patient numbers are indicated. Error bars: ±standard deviation

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IU- PAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "CLDN18" relates to claudin 18 and includes any variants, including claudin 18 splice variant 1 (claudin 18.1 (CLDN18.1)) and claudin 18 splice variant 2 (claudin 18.2 (CLDN18.2)).

The term "CLDN18.2" preferably relates to human CLDN18.2, and, in particular, to a protein comprising, preferably consisting of the amino acid sequence according to SEQ ID NO: 1 of the sequence listing or a variant of said amino acid sequence.

The term "CLDN18.1" preferably relates to human CLDN18.1, and, in particular, to a protein comprising, preferably consisting of the amino acid sequence according to SEQ ID NO: 2 of the sequence listing or a variant of said amino acid sequence.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

According to the invention, the term "CLDN18.2 positive cancer" means a cancer involving cancer cells expressing CLDN18.2, preferably on the surface of said cancer cells.

"Cell surface" is used in accordance with its normal meaning in the art, and thus includes the outside of the cell which is accessible to binding by proteins and other molecules.

CLDN18.2 is expressed on the surface of cells if it is located at the surface of said cells and is accessible to binding by CLDN18.2-specific antibodies added to the cells.

According to the invention, CLDN18.2 is not substantially expressed in a cell if the level of expression is lower compared to expression in stomach cells or stomach tissue. Preferably, the level of expression is less than 10%, preferably less than 5%, 3%, 2%, 1%, 0.5%, 0.1% or 0.05% of the expression in stomach cells or stomach tissue or even lower. Preferably, CLDN18.2 is not substantially expressed in a cell if the level of expression exceeds the level of expression in non-cancerous tissue other than stomach by no more than 2-fold, preferably 1,5-fold, and preferably does not exceed the level of expression in said non-cancerous tissue. Preferably, CLDN18.2 is not substantially expressed in a cell if the level of expression is below the detection limit and/or if the level of expression is too low to allow binding by CLDN18.2-specific antibodies added to the cells.

According to the invention, CLDN18.2 is expressed in a cell if the level of expression exceeds the level of expression in non-cancerous tissue other than stomach preferably by more than 2-fold, preferably 10-fold, 100-fold, 1000-fold, or 10000-fold. Preferably, CLDN18.2 is expressed in a cell if the level of expression is above the detection limit and/or if the level of expression is high enough to allow binding by CLDN18.2-specific antibodies added to the cells. Preferably, CLDN18.2 expressed in a cell is expressed or exposed on the surface of said cell.

According to the invention, the term "disease" refers to any pathological state, including cancer, in particular those forms of cancer described herein. Any reference herein to cancer or particular forms of cancer also includes cancer metastasis thereof. In a preferred embodiment, a disease to be treated according to the present application involves cells expressing CLDN18.2.

"Diseases associated with cells expressing CLDN18.2" or similar expressions means according to the invention that CLDN18.2 is expressed in cells of a diseased tissue or organ. In one embodiment, expression of CLDN18.2 in cells of a diseased tissue or organ is increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed. According to the invention, diseases associated with cells expressing CLDN18.2 include cancer diseases. Furthermore, according to the invention, cancer diseases preferably are those wherein the cancer cells express CLDN18.2.

As used herein, a "cancer disease" or "cancer" includes a disease characterized by aberrantly regulated cellular growth, proliferation, differentiation, adhesion, and/or migration. The three malignant properties of cancers (uncontrolled growth (division beyond the normal limits), invasion (intrusion on and destruction of adjacent tissues), and sometimes metastasis (spread to other locations in the body via lymph or blood)) differentiate cancers from benign tumors, which are self-limited, and do not invade or metastasize. Most cancers form a tumor but some, like leukemia, do not. By "cancer cell" is meant an abnormal cell that grows by a rapid, uncontrolled cellular proliferation and continues to grow after the stimuli that initiated the new growth cease. Preferably, a "cancer disease" is characterized by cells expressing CLDN18.2 and a cancer cell expresses CLDN18.2. A cell expressing CLDN18.2 preferably is a cancer cell, preferably of the cancers described herein.

According to the invention, the term "tumor" or "tumor disease" refers to an abnormal growth of cells (called neoplastic cells, tumorigenous cells or tumor cells) preferably forming a swelling or lesion. By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

According to the invention a tumor is preferably a malignant tumor. "Malignant tumor" is used synonymous with cancer.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis. One particular form of metastasis which is treatable using the therapy of the invention is metastasis originating from gastric cancer as primary site. In preferred embodiments such gastric cancer metastasis is Krukenberg tumors, peritoneal metastasis and/or lymph node metastasis.

Krukenberg tumor is an uncommon metastatic tumor of the ovary accounting for 1% to 2% of all ovarian tumors. Prognosis of Krukenberg tumor is still very poor and there is no established treatment for Krukenberg tumors. Krukenberg tumor is a metastatic signet ring cell adenocarcinoma of the ovary. Stomach is the primary site in most Krukenberg tumor cases (70%). Carcinomas of colon, appendix, and breast (mainly invasive lobular carcinoma) are the next most common primary sites. Rare cases of Krukenberg tumor originating from carcinomas of the gallbladder, biliary tract, pancreas, small intestine, ampulla of Vater, cervix, and urinary bladder/urachus have been reported.

Women with Krukenberg tumors tend to be unusually young for patients with metastatic carcinoma as they are typically in the fifth decade of their lives, with an average age of 45 years. This young age of distribution can be related in part to the increased frequency of gastric signet ring cell carcinomas in young women. Common presenting symptoms are usually related to ovarian involvement, the most common of which are abdominal pain and distension (mainly because of the usually bilateral and often large ovarian masses). The remaining patients have nonspecific gastrointestinal symptoms or are asymptomatic. In addition, Krukenberg tumor is reportedly associated with virilization resulting from hormone production by ovarian stroma. Ascites is present in 50% of the cases and usually reveals malignant cells.

Krukenberg tumors are bilateral in more than 80% of the reported cases. The ovaries are usually asymmetrically enlarged, with a bosselated contour. The sectioned surfaces are yellow or white; they are usually solid, although they are occasionally cystic. Importantly, the capsular surface of the ovaries with Krukenberg tumors is typically smooth and free of adhesions or peritoneal deposits. Of note, other metastatic tumors to the ovary tend to be associated with surface implants. This may explain why the gross morphology of Krukenberg tumor can deceptively appear as a primary ovarian tumor. However, bilateralism in Krukenberg tumor is consistent with its metastatic nature.

Patients with Krukenberg tumors have an overall mortality rate that is significantly high. Most patients die within 2 years (median survival, 14 months). Several studies show that the prognosis is poor when the primary tumor is identified after the metastasis to the ovary is discovered, and the prognosis becomes worse if the primary tumor remains covert.

By "treat" is meant to administer a compound or composition or a combination of compounds or compositions to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject.

In particular, the term "treatment of a disease" includes curing, shortening the duration, ameliorating, preventing, slowing down or inhibiting progression or worsening, or preventing or delaying the onset of a disease or the symptoms thereof.

The term "patient" means according to the invention a subject for treatment, in particular a diseased subject, including human beings, nonhuman primates or another animals, in particular mammals such as cows, horses, pigs, sheeps, goats, dogs, cats or rodents such as mice and rats. In a particularly preferred embodiment, a patient is a human being.

According to the invention, an antibody having the ability of binding to CLDN18.2 may be administered in combination with, i.e. simultaneously with, followed by and/or following, an agent stabilizing or increasing expression of CLDN18.2.

The term "agent stabilizing or increasing expression of CLDN18.2" refers to an agent or a combination of agents the provision of which to cells results in increased RNA and/or protein levels of CLDN18.2, preferably in increased levels of CLDN18.2 protein on the cell surface, compared to the situation where the cells are not provided with the agent or the combination of agents. Preferably, the cell is a cancer cell, in particular a cancer cell expressing CLDN18.2, such as a cell of the cancer types described herein. The term "agent stabilizing or increasing expression of CLDN18.2" refers, in particular, to an agent or a combination of agents the provision of which to cells results in a higher density of CLDN18.2 on the surface of said cells compared to the situation where the cells are not provided with the agent or the combination of agents. "Stabilizing expression of CLDN18.2" includes, in particular, the situation where the agent or the combination of agents prevents a decrease or reduces a decrease in expression of CLDN18.2, e.g. expression of CLDN18.2 would decrease without provision of the agent or the combination of agents and provision of the agent or the combination of agents prevents said decrease or reduces said decrease of CLDN18.2 expression. "Increasing expression of CLDN18.2" includes, in particular, the situation where the agent or the combination of agents increases expression of CLDN18.2, e.g. expression of CLDN18.2 would decrease, remain essentially constant or increase without provision of the agent or the combination of agents and provision of the agent or the combination of agents increases CLDN18.2 expression compared to the situation without provision of the agent or the combination of agents so that the resulting expression is higher compared to the situation where expression of CLDN18.2 would decrease, remain essentially constant or increase without provision of the agent or the combination of agents.

According to the invention, the term "agent stabilizing or increasing expression of CLDN18.2" includes chemotherapeutic agents or combinations of chemotherapeutic agents such as cytostatic agents. Chemotherapeutic agents may affect cells in one of the following ways: (1) Damage the DNA of the cells so they can no longer reproduce, (2) Inhibit the synthesis of new DNA strands so that no cell replication is possible, (3) Stop the mitotic processes of the cells so that the cells cannot divide into two cells.

According to the invention, the term "agent stabilizing or increasing expression of CLDN18.2" preferably relates to an agent or a combination of agents such a cytostatic compound or a combination of cytostatic compounds the provision of which to cells, in particular cancer cells, results in the cells being arrested in or accumulating in one or more phases of the cell cycle, preferably in one or more phases of the cell cycle other than the G1- and G0-phases, preferably other than the G1-phase, preferably in one or more of the G2- or S-phase of the cell cycle such as the G1/G2-, S/G2-, G2- or S-phase of the cell cycle. The term "cells being arrested in or accumulating in one or more phases of the cell cycle" means that the percentage of cells which are in said one or more phases of the cell cycle increases. Each cell goes through a cycle comprising four phases in order to replicate itself. The first phase called G1 is when the cell prepares to replicate its chromosomes. The second stage is called S, and in this phase DNA synthesis occurs and the DNA is duplicated. The next phase is the G2 phase, when the RNA and protein duplicate. The final stage is the M stage, which is the stage of actual cell division. In this final stage, the duplicated DNA and RNA split and move to separate ends of the cell, and the cell actually divides into two identical, functional cells. Chemotherapeutic agents which are DNA damaging agents usually result in an accumulation of cells in the G1 and/or G2 phase. Chemotherapeutic agents which block cell growth by interfering with DNA synthesis such as antimetabolites usually result in an accumulation of cells in the S-phase. Examples of these drugs are 6-mercaptopurine and 5-fluorouracil.

According to the invention, the term "agent stabilizing or increasing expression of CLDN18.2" includes anthracyclines such as epirubicin, platinum compounds such as oxaliplatin and cisplatin, nucleoside analogs such as 5-fluorouracil or prodrugs thereof, taxanes such as docetaxel, and camptothecin analogs such as irinotecan and topotecan, and combinations of drugs such as combinations of drugs comprising one or more of anthracyclines such as epirubicin, oxaliplatin and 5-fluorouracil such as a combination of drugs comprising oxaliplatin and 5-fluorouracil or other drug combinations described herein.

In one preferred embodiment, an "agent stabilizing or increasing expression of CLDN18.2" is an "agent inducing immunogenic cell death".

In specific circumstances, cancer cells can enter a lethal stress pathway linked to the emission of a spatiotemporally defined combination of signals that is decoded by the immune system to activate tumor-specific immune responses (Zitvogel L. et al. (2010) Cell 140: 798-804). In such scenario cancer cells are triggered to emit signals that are sensed by innate immune effectors such as dendritic cells to trigger a cognate immune response that involves CD8+ T cells and IFN-γ signalling so that tumor cell death may elicit a productive anticancer immune response. These signals include the pre-apoptotic exposure of the endoplasmic reticulum (ER) chaperon calreticulin (CRT) at the cell surface, the pre-apoptotic secretion of ATP, and the post-apoptotic release of the nuclear protein HMGB1. Together, these processes constitute the molecular determinants of immunogenic cell death (ICD). Anthracyclines, oxaliplatin, and γ irradiation are able to induce all signals that define ICD, while cisplatin, for example, which is deficient in inducing CRT translocation from the ER to the surface of dying cells—a process requiring ER stress—requires complementation by thapsigargin, an ER stress inducer.

According to the invention, the term "agent inducing immunogenic cell death" refers to an agent or a combination of agents which when provided to cells, in particular cancer cells, is capable of inducing the cells to enter a lethal stress pathway which finally results in tumor-specific immune responses. In particular, an agent inducing immunogenic cell death when provided to cells induces the cells to emit a spatiotemporally defined combination of signals, including, in particular, the pre-apoptotic exposure of the endoplasmic reticulum (ER) chaperon calreticulin (CRT) at the cell surface, the pre-apoptotic secretion of ATP, and the post-apoptotic release of the nuclear protein HMGB1.

According to the invention, the term "agent inducing immunogenic cell death" includes anthracyclines and oxaliplatin.

Anthracyclines are a class of drugs commonly used in cancer chemotherapy that are also antibiotics. Structurally, all anthracyclines share a common four-ringed 7,8,9,10-tetrahydrotetracene-5,12-quinone structure and usually require glycosylation at specific sites.

Anthracyclines preferably bring about one or more of the following mechanisms of action: 1. Inhibiting DNA and RNA synthesis by intercalating between base pairs of the DNA/RNA strand, thus preventing the replication of rapidly-growing cancer cells. 2. Inhibiting topoisomerase II enzyme, preventing the relaxing of supercoiled DNA and thus blocking DNA transcription and replication. 3. Creating iron-mediated free oxygen radicals that damage the DNA and cell membranes.

According to the invention, the term "anthracycline" preferably relates to an agent, preferably an anticancer agent for inducing apoptosis, preferably by inhibiting the rebinding of DNA in topoisomerase II.

Preferably, according to the invention, the term "anthracycline" generally refers to a class of compounds having the following ring structure

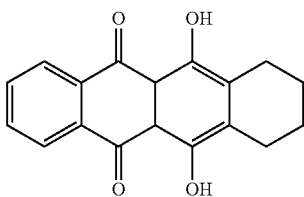 [SMILES: O=C1c2ccccc2C(=O)C2C(O)=C3CCCCC3=C(O)C12]

including analogs and derivatives, pharmaceutical salts, hydrates, esters, conjugates and prodrugs thereof.

Examples of anthracyclines and anthracycline analogs include, but are not limited to, daunorubicin (daunomycin), doxorubicin (adriamycin), epirubicin, idarubicin, rhodomycin, pyrarubicin, valrubicin, N-trifluoro-acetyl doxorubicin-14-valerate, aclacinomycin, morpholinodoxorubicin (morpholino-DOX), cyanomorpholino-doxorubicin (cyanomorpholino-DOX), 2-pyrrolino-doxorubicin (2-PDOX), 5-iminodaunomycin, mitoxantrone and aclacinomycin A (aclarubicin). Mitoxantrone is a member of the anthracendione class of compounds, which are anthracycline analogs that lack the sugar moiety of the anthracyclines but retain the planar polycyclic aromatic ring structure that permits intercalation into DNA.

Particularly preferred as anthracyline according to the invention is a compound of the following formula:

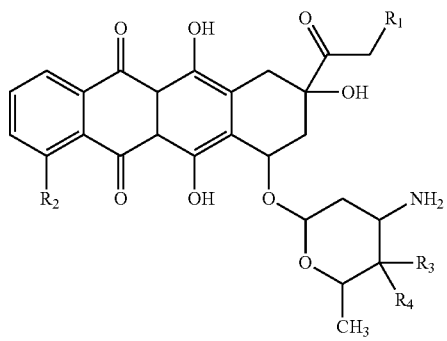

wherein
$R_1$ is selected from the group consisting of H and OH, $R_2$ is selected from the group consisting of H and OMe, $R_3$ is selected from the group consisting of H and OH, and $R_4$ is selected from the group consisting of H and OH.

In one embodiment, $R_1$ is H, $R_2$ is OMe, $R_3$ is H, and $R_4$ is OH. In another embodiment, $R_1$ is OH, $R_2$ is OMe, $R_3$ is H, and $R_4$ is OH. In another embodiment, $R_1$ is OH, $R_2$ is OMe, $R_3$ is OH, and $R_4$ is H. In another embodiment, $R_1$ is H, $R_2$ is H, $R_3$ is H, and $R_4$ is OH.

Specifically contemplated as anthracycline in the context of the present invention is epirubicin. Epirubicin is an anthracycline drug which has the following formula:

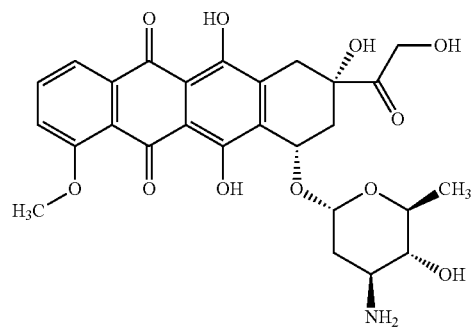 [SMILES: COc1cccc2c1C(=O)c1c(O)c3c(c(O)c1C2=O)C[C@@](O)(C(=O)CO)C[C@@H]3O[C@H]1C[C@H](N)[C@@H](O)[C@H](C)O1]

and is marketed under the trade name Ellence in the US and Pharmorubicin or Epirubicin Ebewe elsewhere. In particular, the term "epirubicin" refers to the compound (8R, 10S)-10-[(2S,4S,5R,6S)-4-amino-5-hydroxy-6-methyl-oxan-2-yl]oxy-6,11-dihydroxy-8-(2-hydroxyacetyl)-1-methoxy-8-methyl-9,10-dihydro-7H-tetracen-5,12-dion. Epirubicin is favoured over doxorubicin, the most popular anthracycline, in some chemotherapy regimens as it appears to cause fewer side-effects.

According to the invention, the term "platinum compound" refers to compounds containing platinum in their structure such as platinum complexes and includes compounds such as cisplatin, carboplatin and oxaliplatin.

The term "cisplatin" or "cisplatinum" refers to the compound cis-diamminedichloroplatinum(II) (CDDP) of the following formula:

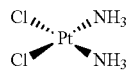

The term "carboplatin" refers to the compound cis-diammine(1,1-cyclobutanedicarboxylato)platinum(II) of the following formula:

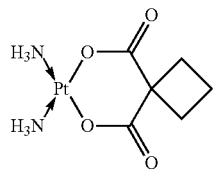

The term "oxaliplatin" refers to a compound which is a platinum compound that is complexed to a diaminocyclohexane carrier ligand of the following formula:

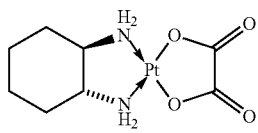

In particular, the term "oxaliplatin" refers to the compound [(1R,2R)-cyclohexane-1,2-diamine](ethanedioato-O,O')platinum(II). Oxaliplatin for injection is also marketed under the trade name Eloxatine.

The term "nucleoside analog" refers to a structural analog of a nucleoside, a category that includes both purine analogs and pyrimidine analogs. In particular, the term "nucleoside analog" refers to fluoropyrimidine derivatives which includes fluorouracil and prodrugs thereof.

The term "fluorouracil" or "5-fluorouracil" (5-FU or f5U) (sold under the brand names Adrucil, Carac, Efudix, Efudex and Fluoroplex) is a compound which is a pyrimidine analog of the following formula:

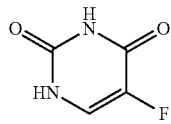

In particular, the term refers to the compound 5-fluoro-1H-pyrimidine-2,4-dione.

The term "capecitabine" (Xeloda, Roche) refers to a chemotherapeutic agent that is a prodrug that is converted into 5-FU in the tissues. Capecitabine which may be orally administered has the following formula:

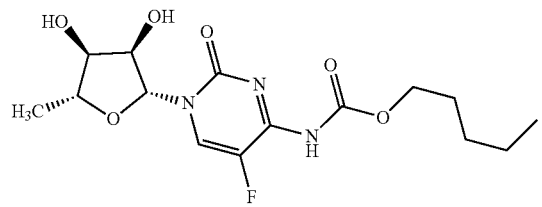 [SMILES: CCCCCOC(=O)Nc1nc(=O)n([C@@H]2O[C@H](C)[C@@H](O)[C@H]2O)cc1F]

In particular, the term refers to the compound pentyl [1-(3,4-dihydroxy-5-methyltetrahydrofuran-2-yl)-5-fluoro-2-oxo-1H-pyrimidin-4-yl]carbamate.

Taxanes are a class of diterpene compounds that were first derived from natural sources such as plants of the genus *Taxus*, but some have been synthesized artificially. The principal mechanism of action of the taxane class of drugs is the disruption of microtubule function, thereby inhibiting the process of cell division. Taxanes include docetaxel (Taxotere) and paclitaxel (Taxol).

According to the invention, the term "docetaxel" refers to a compound having the following formula:

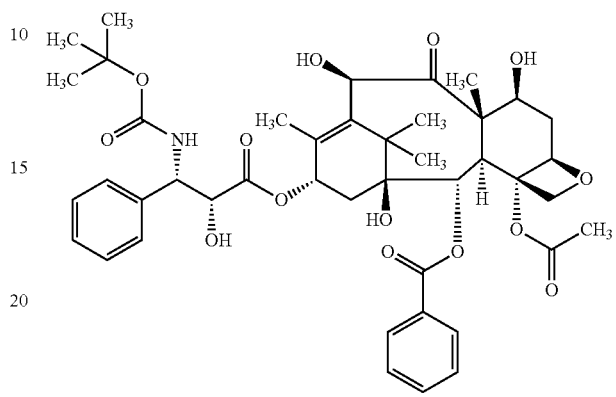

According to the invention, the term "paclitaxel" refers to a compound having the following formula:

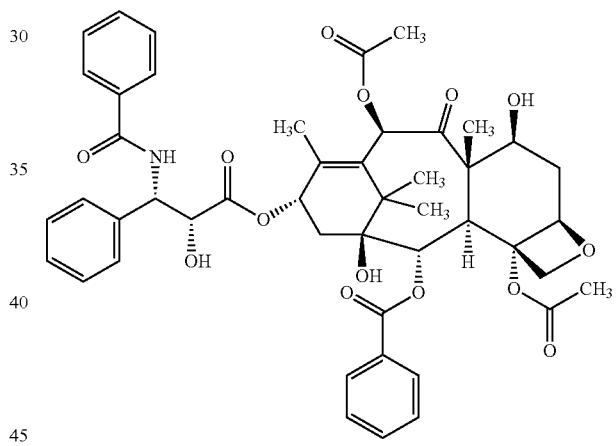

According to the invention, the term "camptothecin analog" refers to derivatives of the compound camptothecin (CPT; (S)-4-ethyl-4-hydroxy-1H-pyrano[3',4':6,7]indolizino[1,2-b] quinoline-3,14-(4H,12H)-dione). Preferably, the term "camptothecin analog" refers to compounds comprising the following structure:

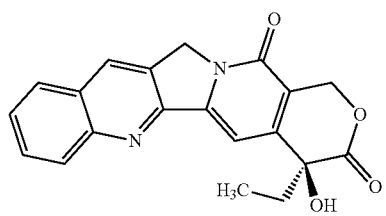 [SMILES: CC[C@@]1(O)C(=O)OCc2c1cc1n(c2=O)Cc2cc3ccccc3nc2-1]

According to the invention, preferred camptothecin analogs are inhibitors of DNA enzyme topoisomerase I (topo I). Preferred camptothecin analogs according to the invention are irinotecan and topotecan.

Irinotecan is a drug preventing DNA from unwinding by inhibition of topoisomerase I. In chemical terms, it is a semisynthetic analogue of the natural alkaloid camptothecin having the following formula:

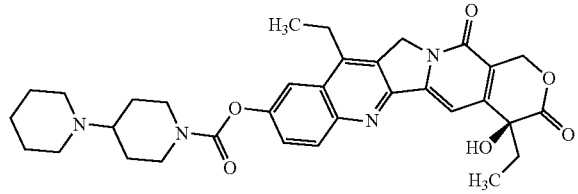 [SMILES: CCc1c2c(nc3ccc(OC(=O)N4CCC(N5CCCCC5)CC4)cc13)-c1cc3c(c(=O)n1C2)COC(=O)[C@]3(O)CC]

In particular, the term "irinotecan" refers to the compound (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate.

Topotecan is a topoisomerase inhibitor of the formula:

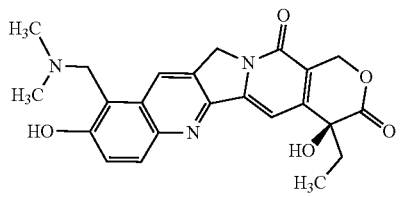 [SMILES: CC[C@@]1(O)C(=O)OCc2c1cc1n(c2=O)Cc2cc3c(CN(C)C)c(O)ccc3nc2-1]

In particular, the term "topotecan" refers to the compound (S)-10-[(dimethylamino)methyl]-4-ethyl-4,9-dihydroxy-1H-pyrano[3',4':6,7]indolizino[1,2-b]quinoline-3,14(4H,12H)-dione monohydrochloride.

According to the invention, an agent stabilizing or increasing expression of CLDN18.2 may be a chemotherapeutic agent, in particular a chemotherapeutic agent established in cancer treatment and may be part of a combination of drugs such as a combination of drugs established for use in cancer treatment. Such combination of drugs may be a drug combination used in chemotherapy, and may be a drug combination as used in a chemotherapeutic regimen selected from the group consisting of EOX chemotherapy, ECF chemotherapy, ECX chemotherapy, EOF chemotherapy, FLO chemotherapy, FOLFOX chemotherapy, FOLFIRI chemotherapy, DCF chemotherapy and FLOT chemotherapy.

The drug combination used in EOX chemotherapy comprises of epirubicin, oxaliplatin and capecitabine. The drug combination used in ECF chemotherapy comprises of epirubicin, cisplatin and 5-fluorouracil. The drug combination used in ECX chemotherapy comprises of epirubicin, cisplatin and capecitabine. The drug combination used in EOF chemotherapy comprises of epirubicin, oxaliplatin and 5-fluorouracil.

Epirubicin is normally given at a dose of 50 mg/m2, cisplatin 60 mg/m2, oxaliplatin 130 mg/m2, protracted venous infusion of 5-fluorouracil at 200 mg/m2/day and oral capecitabine 625 mg/m2 twice daily, for a total of eight 3-week cycles.

The drug combination used in FLO chemotherapy comprises of 5-fluorouracil, folinic acid and oxaliplatin (normally 5-fluorouracil 2,600 mg/m2 24-h infusion, folinic acid 200 mg/m2 and oxaliplatin 85 mg/m2, every 2 weeks).

FOLFOX is a chemotherapy regimen made up of folinic acid (leucovorin), 5-fluorouracil and oxaliplatin. The recommended dose schedule given every two weeks is as follows: Day 1: Oxaliplatin 85 mg/m² IV infusion and leucovorin 200 mg/m² IV infusion, followed by 5-FU 400 mg/m² IV bolus, followed by 5-FU 600 mg/m² IV infusion as a 22-hour continuous infusion; Day 2: Leucovorin 200 mg/m² IV infusion over 120 minutes, followed by 5-FU 400 mg/m² IV bolus given over 2-4 minutes, followed by 5-FU 600 mg/m² IV infusion as a 22-hour continuous infusion.

The drug combination used in FOLFIRI chemotherapy comprises of 5-fluorouracil, leucovorin, and irinotecan.

The drug combination used in DCF chemotherapy comprises of docetaxel, cisplatin and 5-fluorouracil.

The drug combination used in FLOT chemotherapy comprises of docetaxel, oxaliplatin, 5-fluorouracil and folinic acid.

The term "folinic acid" or "leucovorin" refers to a compound useful in synergistic combination with the chemotherapy agent 5-fluorouracil. Folinic acid has the following formula:

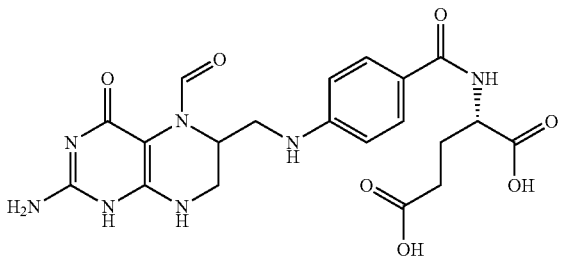 [SMILES: Nc1nc(=O)c2c([nH]1)NCC(CNc1ccc(C(=O)N[C@@H](CCC(=O)O)C(=O)O)cc1)N2C=O]

In particular, the term refers to the compound (2S)-2-{[4-[(2-amino-5-formyl-4-oxo-5,6,7,8-tetrahydro-1H-pteridin-6-yl)methylamino]benzoyl]amino}pentanedioic acid.

According to the invention, an antibody having the ability of binding to CLDN18.2 may be administered in combination with, i.e. simultaneously with, followed by and/or following, an agent stimulating γδ T cells.

γδ T cells (gamma delta T cells) represent a small subset of T cells that possess a distinct T cell receptor (TCR) on their surface. A majority of T cells have a TCR composed of two glycoprotein chains called α- and β-TCR chains. In contrast, in γδ T cells, the TCR is made up of one γ-chain and one δ-chain. This group of T cells is usually much less common than αβ T cells. Human γδ T cells play an important role in stress-surveillance responses like infectious diseases and autoimmunity. Transformation-induced changes in tumors are also suggested to cause stress-surveillance responses mediated by γδ T cells and enhance antitumor immunity. Importantly, after antigen engagement, activated γδ T cells at lesional sites provide cytokines (e.g. INFγ, TNFα) and/or chemokines mediating recruitment of other effector cells and show immediate effector functions such as cytotoxicity (via death receptor and cytolytic granules pathways) and ADCC.

The majority of γδ T cells in peripheral blood express the Vγ9Vδ2 T cell receptor (TCRγδ). Vγ9Vδ2 T cells are unique to humans and primates and are assumed to play an early and essential role in sensing "danger" by invading pathogens as they expand dramatically in many acute infections and may exceed all other lymphocytes within a few days, e.g. in tuberculosis, salmonellosis, ehrlichiosis, brucellosis, tularemia, listeriosis, toxoplasmosis, and malaria.

γδ T cells respond to small non-peptidic phosphorylated antigens (phosphoantigens) such as pyrophosphates synthesized in bacteria and isopentenyl pyrophosphate (IPP) produced in mammalian cells through the mevalonate pathway.

Whereas IPP production in normal cells is not sufficient for activation of γδ T cells, dysregulation of the mevalonate pathway in tumor cells leads to accumulation of IPP and γδ T cell activation. IPPs can also be therapeutically increased by aminobisphosphonates, which inhibit the mevalonate pathway enzyme farnesyl pyrophosphate synthase (FPPS). Among others, zoledronic acid (ZA, zoledronate, Zometa™, Novartis) represents such an aminobiphosphonate, which is already clinically administered to patients for the treatment of osteoporosis and metastasic bone disease. Upon treatment of PBMCs in vitro, ZA is taken up especially by monocytes. IPP accumulates in the monocytes and they differentiate to antigen-presenting cells stimulating development of γδ T cells. In this setting, the addition of interleukin-2 (IL-2) is preferred as growth and survival factor for activated γδ T cells. Finally, certain alkylated amines have been described to activate Vγ9Vδ2 T cells in vitro, however only at millimolar concentrations.

According to the invention, the term "agent stimulating γδ T cells" relates to compounds stimulating development of γδ T cells, in particular Vγ9Vδ2 T cells, in vitro and/or in vivo, in particular by inducing activation and expansion of γδ T cells. Preferably, the term relates to compounds which in vitro and/or in vivo increase isopentenyl pyrophosphate (IPP) produced in mammalian cells, preferably by inhibiting the mevalonate pathway enzyme farnesyl pyrophosphate synthase (FPPS).

One particular group of compounds stimulating γδ T cells are bisphosphonates, in particular nitrogen-containing bisphosphonates (N-bisphosphonates; aminobisphosphonates).

For example, suitable bisphosphonates for use in the invention may include one or more of the following compounds including analogs and derivatives, pharmaceutical salts, hydrates, esters, conjugates and prodrugs thereof: [1-hydroxy-2-(1H-imidazol-1-yl)ethane-1,1-diyl]bis(phosphonic acid), zoledronic acid, e.g. zoledronate; (dichlorophosphono-methyl)phosphonic acid, e.g. clodronate {1-hydroxy-3-[methyl(pentyl)amino]propane-1,1-diyl}bis (phosphonic acid), ibandronic acid, e.g. ibandronate (3-amino-1-hydroxypropane-1,1-diyl)bis (phosphonic acid), pamidronic acid, e.g. pamidronate; (1-hydroxy-1-phosphono-2-pyridin-3-yl-ethyl)phosphonic acid, risedronic acid, e.g. risedronate; (1-Hydroxy-2-imidazo[1,2-a]pyridin-3-yl-1-phosphonoethyl)phosphonic acid, minodronic acid; [3-(dimethylamino)-1-hydroxypropane-1,1-diyl]bis(phosphonic acid), olpadronic acid. [4-amino-1-hydroxy-1-(hydroxy-oxido-phosphoryl)-butyl]phosphonic acid, alendronic acid, e.g. alendronate; [(Cycloheptylamino)methylene]bis (phosphonic acid), incadronic acid; (1-hydroxyethan-1,1-diyl)bis(phosphonic acid), etidronic acid, e.g. etidronate; and {[(4-chlorophenyl)thio]methylene}bis(phosphonic acid), tiludronic acid.

According to the invention, zoledronic acid (INN) or zoledronate (marketed by Novartis under the trade names Zometa, Zomera, Aclasta and Reclast) is a particularly preferred bisphosphonate. Zometa is used to prevent skeletal fractures in patients with cancers such as multiple myeloma and prostate cancer, as well as for treating osteoporosis. It can also be used to treat hypercalcemia of malignancy and can be helpful for treating pain from bone metastases.

In one particularly preferred embodiment, an agent stimulating γδ T cells according to the invention is administered in combination with IL-2. Such combination has been shown to be particularly effective in mediating expansion and activation of γ9δ2 T cells.

Interleukin-2 (IL-2) is an interleukin, a type of cytokine signaling molecule in the immune system. It is a protein that attracts lymphocytes and is part of the body's natural response to microbial infection, and in discriminating between foreign (non-self) and self IL-2 mediates its effects by binding to IL-2 receptors, which are expressed by lymphocytes.

The IL-2 used according to the invention may be any IL-2 supporting or enabling the stimulation of γδ T cells and may be derived from any species, preferably human. 11-2 may be isolated, recombinantly produced or synthetic IL-2 and may be naturally occurring or modified IL-2.

According to the invention the term "antiemetic" relates to a compound, composition or drug that is effective against vomiting and/or nausea. In one embodiment, the antiemetic includes a 5-HT3 receptor antagonist and/or a neurokinin 1 (NK1) receptor antagonist.

5-HT3 receptor antagonists block serotonin receptors in the central nervous system and gastrointestinal tract. Examples thereof include, but are not limited to Ondansetron (Zofran) which can be administered in an oral tablet form, oral dissolving tablet form, or in an injection, Dolasetron (Anzemet) which can be administered in tablet form or in an injection, Granisetron (Kytril, Sancuso) which can be administered in tablet (Kytril), oral solution (Kytril), injection (Kytril), or in a single transdermal patch to the upper arm (Sancuso), Tropisetron (Navoban) which can be administered in oral capsules or in injection form, Palonosetron (Aloxi) which can be administered in an injection or in oral capsules and Mirtazapine (Remeron).

NK1 receptor antagonists include, but are not limited to Aprepitant (Emend).

A preferred combination of a 5-HT3 receptor antagonist and a NK1 receptor antagonist is a combination of Ondansetron (Zofran) and Aprepitant (Emend).

Further antiemetics which can be used according to the invention, in particular in combination with a 5-HT3 receptor antagonist and/or a NK1 receptor antagonist include but are not limited to Metoclopramide (Reglan) which acts on the GI tract as a pro-kinetic, Lorazepam, Atropin, Alizapride (Litican, Plitican, Superan, Vergentan) and Dimenhydrinate (Dramamine, Driminate, Gravol, Gravamin, Vomex, Vertirosan).

According to the invention, an antispasmodic (synonym: spasmolytic) can be administered. According to the invention the term "antispasmodic" relates a compound, composition or drug that suppresses muscle spasms. Preferably, an antispasmodic is useful for smooth muscle contraction. Preferred according to the invention are antispasmodics which are effective in treating spasmodic activity in the digestive system. Thus, preferred antispasmodics are effective in the relief of gastrointestinal spasms.

Antispasmodics include, but are not limited to butylscopolamine which is also known as scopolamine butylbromide, butylhyoscine and hyoscine butylbromide. It is marketed under the trade name Buscopan by Boehringer Ingelheim GmbH, Germany.

According to the invention, a parasympatholytic can be administered. According to the invention the term "parasympatholytic" relates to a compound, composition or drug that reduces the activity of the parasympathetic nervous system. Parasympatholytics include, but are not limited to Atropine.

According to the invention the term "proton-pump inhibitor" relates to a compound, composition or drug whose main action is a pronounced and long-lasting reduction of gastric acid production.

Proton-pump inhibitors include benzimidazole derivatives and imidazopyridine derivatives. Examples of proton-pump inhibitors include, but are not limited to Omeprazole (brand names: Gasec, Losec, Prilosec, Zegerid, ocid, Lomac, Omepral, Omez), Lansoprazole (brand names: Prevacid, Zoton, Monolitum, Inhibitol, Levant, Lupizole), Dexlansoprazole (brand name: Kapidex, Dexilant), Esomeprazole (brand names: Nexium, Esotrex, esso), Pantoprazole (brand names: Protonix, Somac, Pantoloc, Pantozol, Zurcal, Zentro, Pan, Controloc, Tecta), Rabeprazole (brand names: AcipHex, Pariet, Erraz, Zechin, Rabecid, Nzole-D, Rabeloc, Razo) and Ilaprazole (brand names: Ilapro, Lupilla, Adiza).

According to the invention, other compounds, compositions or drugs can be administered which have a protective effect on gastric mucosa, in particular if a nonsteroidal anti-inflammatory drug (NSAID) is administered.

For example, other compounds, compositions or drugs can be administered to prevent the common adverse effect of gastric ulceration of NSAIDs, in particular to prevent NSAID induced gastric ulcers. In one embodiment, Misoprostol can be administered which is a synthetic prostaglandin E1 (PGE1) analog that is used for the prevention of NSAID induced gastric ulcers. Misoprostol acts upon gastric parietal cells, inhibiting the secretion of gastric acid via G-protein coupled receptor mediated inhibition of adenylate cyclase, which leads to decreased intracellular cyclic AMP levels and decreased proton pump activity at the apical surface of the parietal cell.

Furthermore, Omeprazole proved to be at least as effective as Misoprostol in the treatment of NSAID induced ulcers but significantly better tolerated.

Nonsteroidal anti-inflammatory drugs (NSAIDs) are a class of drugs that provide analgesic and antipyretic (fever-reducing) effects, and, in higher doses, anti-inflammatory effects. The term "nonsteroidal" distinguishes these drugs from steroids. The most prominent members of this group of drugs are aspirin, ibuprofen, and naproxen.

One of the main adverse drug reactions (ADRs) associated with NSAIDs relate to the gastrointestinal (GI) effects of NSAIDs. These effects are in many cases severe enough to pose the risk of ulcer perforation and upper gastrointestinal bleeding. NSAID patients experience dyspepsia, NSAID-associated upper gastrointestinal adverse events, irritation of the gastrointestinal (GI) tract and GI ulceration. NSAIDs cause a dual assault on the GI tract: the acidic molecules directly irritate the gastric mucosa, and inhibition of COX-1 and COX-2 reduces the levels of protective prostaglandins. Inhibition of prostaglandin synthesis in the GI tract causes increased gastric acid secretion, diminished bicarbonate secretion, diminished mucus secretion and diminished trophic effects on epithelial mucosa. Thus, NSAIDs are preferably not administered according to the invention. Paracetamol or "acetaminophen" which is not classified as a NSAID because it only exerts weak anti-inflammatory effects can be administered as analgesic according to the invention, however, it may not be efficient for pain management and thus, administration of an NSAID could become necessary, in particular to avoid administration of opioids.

Commonly, gastric (but not necessarily intestinal) adverse effects can be reduced through suppressing acid production, by concomitant use of a proton pump inhibitor, e.g. Omeprazole, Esomeprazole; or the prostaglandin analogue Misoprostol.

The term "antigen" relates to an agent such as a protein or peptide comprising an epitope against which an immune response is directed and/or is to be directed. In a preferred embodiment, an antigen is a tumor-associated antigen, such as CLDN18.2, i.e., a constituent of cancer cells which may be derived from the cytoplasm, the cell surface and the cell nucleus, in particular those antigens which are produced, preferably in large quantity, intracellular or as surface antigens on cancer cells.

In the context of the present invention, the term "tumor-associated antigen" preferably relates to proteins that are under normal conditions specifically expressed in a limited number of tissues and/or organs or in specific developmental stages and are expressed or aberrantly expressed in one or more tumor or cancer tissues. In the context of the present invention, the tumor-associated antigen is preferably associated with the cell surface of a cancer cell and is preferably not or only rarely expressed in normal tissues.

The term "epitope" refers to an antigenic determinant in a molecule, i.e., to the part in a molecule that is recognized by the immune system, for example, that is recognized by an antibody. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. An epitope of a protein such as CLDN18.2 preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

The term "antibody" refers to a glycoprotein comprising at least two heavy (H) chains and two light (L) chains inter-connected by disulfide bonds, and includes any molecule comprising an antigen binding portion thereof. The term "antibody" includes monoclonal antibodies and fragments or derivatives of antibodies, including, without limitation, human antibodies, humanized antibodies, chimeric antibodies, single chain antibodies, e.g., scFv's and antigen-binding antibody fragments such as Fab and Fab' fragments and also includes all recombinant forms of antibodies, e.g., antibodies expressed in prokaryotes, unglycosylated antibodies, and any antigen-binding antibody fragments and derivatives as described herein. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The antibodies described herein may be human antibodies. The term "human antibody", as used herein, is intended to include antibodies having variable and constant regions derived from human germline immunoglobulin sequences. The human antibodies described herein may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

The terms "antigen-binding portion" of an antibody (or simply "binding portion") or "antigen-binding fragment" of an antibody (or simply "binding fragment") or similar terms refer to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "bispecific molecule" is intended to include any agent, e.g., a protein, peptide, or protein or peptide complex, which has two different binding specificities. For example, the molecule may bind to, or interact with (a) a cell surface antigen, and (b) an Fc receptor on the surface of an effector cell. The term "multispecific molecule" or "heterospecific molecule" is intended to include any agent, e.g., a protein, peptide, or protein or peptide complex, which has more than two different binding specificities. For example, the molecule may bind to, or interact with (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to CLDN18.2, and to other targets, such as Fc receptors on effector cells. The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90: 6444-6448; Poljak, R. J., et al. (1994) Structure 2: 1121-1123).

An antibody may be conjugated to a therapeutic moiety or agent, such as a cytotoxin, a drug (e.g., an immunosuppressant) or a radioisotope. A cytotoxin or cytotoxic agent includes any agent that is detrimental to and, in particular, kills cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Suitable therapeutic agents for forming antibody conjugates include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin, cisplatin, bleomycin, sulfate, carmustine, chlorambucil, cyclophosphamide or ricin A.

Antibodies also can be conjugated to a radioisotope, e.g., iodine-131, yttrium-90 or indium-111, to generate cytotoxic radiopharmaceuticals.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *Pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

As used herein, an antibody is "derived from" a particular germline sequence if the antibody is obtained from a system by immunizing an animal or by screening an immunoglobulin gene library, and wherein the selected antibody is at least 90%, more preferably at least 95%, even more preferably at least 96%, 97%, 98%, or 99% identical in amino acid sequence to the amino acid sequence encoded by the germline immunoglobulin gene. Typically, an antibody derived from a particular germline sequence will display no more than 10 amino acid differences, more preferably, no more than 5, or even more preferably, no more than 4, 3, 2, or 1 amino acid difference from the amino acid sequence encoded by the germline immunoglobulin gene.

As used herein, the term "heteroantibodies" refers to two or more antibodies, derivatives thereof, or antigen binding regions linked together, at least two of which have different specificities. These different specificities include a binding specificity for an Fc receptor on an effector cell, and a binding specificity for an antigen or epitope on a target cell, e.g., a tumor cell.

The antibodies described herein may be monoclonal antibodies. The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The antibodies described herein may be recombinant antibodies. The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

Antibodies described herein may be derived from different species, including but not limited to mouse, rat, rabbit, guinea pig and human.

Antibodies described herein include polyclonal and monoclonal antibodies and include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

The term "transfectoma", as used herein, includes recombinant eukaryotic host cells expressing an antibody, such as CHO cells, NS/0 cells, HEK293 cells, HEK293T cells, plant cells, or fungi, including yeast cells.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

The invention includes all antibodies and derivatives of antibodies as described herein which for the purposes of the invention are encompassed by the term "antibody". The term "antibody derivatives" refers to any modified form of an antibody, e.g., a conjugate of the antibody and another agent or antibody, or an antibody fragment.

The antibodies described herein are preferably isolated. An "isolated antibody" as used herein, is intended to refer to an antibody which is substantially free of other antibodies having different antigenic specificities (e.g., an isolated antibody that specifically binds to CLDN18.2 is substantially free of antibodies that specifically bind antigens other than CLDN18.2). An isolated antibody that specifically binds to an epitope, isoform or variant of human CLDN18.2 may, however, have cross-reactivity to other related antigens, e.g., from other species (e.g., CLDN18.2 species homologs). Moreover, an isolated antibody may be substantially free of other cellular material and/or chemicals. In one embodiment of the invention, a combination of "isolated"

monoclonal antibodies relates to antibodies having different specificities and being combined in a well defined composition or mixture.

The term "binding" according to the invention preferably relates to a specific binding.

According to the present invention, an antibody is capable of binding to a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An antibody is not (substantially) capable of binding to a target if it has no significant affinity for said target and does not bind significantly, in particular does not bind detectably, to said target in standard assays. Preferably, the antibody does not detectably bind to said target if present in a concentration of up to 2, preferably 10, more preferably 20, in particular 50 or 100 µg/ml or higher. Preferably, an antibody has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the antibody is capable of binding. For example, if the $K_D$ for binding of an antibody to the target to which the antibody is capable of binding is $10^{-7}$ M, the $K_D$ for binding to a target for which the antibody has no significant affinity would be is at least $10^{-6}$ M, $10^{-5}$ M, $10^{-4}$ M, $10^{-3}$ M, $10^{-2}$ M, or $10^{-1}$ M.

An antibody is specific for a predetermined target if it is capable of binding to said predetermined target while it is not capable of binding to other targets, i.e. has no significant affinity for other targets and does not significantly bind to other targets in standard assays. According to the invention, an antibody is specific for CLDN18.2 if it is capable of binding to CLDN18.2 but is not (substantially) capable of binding to other targets. Preferably, an antibody is specific for CLDN18.2 if the affinity for and the binding to such other targets does not significantly exceed the affinity for or binding to CLDN18.2-unrelated proteins such as bovine serum albumin (BSA), casein, human serum albumin (HSA) or non-claudin transmembrane proteins such as MHC molecules or transferrin receptor or any other specified polypeptide. Preferably, an antibody is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an antibody to the target for which it is specific is $10^{-7}$ M, the $K_D$ for binding to a target for which it is not specific would be at least $10^{-6}$ M, $10^{-5}$ M, $10^{-4}$ M, $10^{-3}$ M, $10^{-2}$ M, or $10^{-1}$ M.

Binding of an antibody to a target can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. Affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

According to the invention an antibody having the ability of binding to CLDN18.2 is an antibody capable of binding to an epitope present in CLDN18.2, preferably an epitope located within the extracellular domains of CLDN18.2, in particular the first extracellular domain, preferably amino acid positions 29 to 78 of CLDN18.2. In particular embodiments, an antibody having the ability of binding to CLDN18.2 is an antibody capable of binding to (i) an epitope on CLDN18.2 which is not present on CLDN18.1, preferably SEQ ID NO: 3, 4, and 5, (ii) an epitope localized on the CLDN18.2-loop1, preferably SEQ ID NO: 8, (iii) an epitope localized on the CLDN18.2-loop2, preferably SEQ ID NO: 10, (iv) an epitope localized on the CLDN18.2-loopD3, preferably SEQ ID NO: 11, (v) an epitope, which encompass CLDN18.2-loop1 and CLDN18.2-loopD3, or (vi) a non-glycosylated epitope localized on the CLDN18.2-loopD3, preferably SEQ ID NO: 9.

According to the invention an antibody having the ability of binding to CLDN18.2 preferably is an antibody having the ability of binding to CLDN18.2 but not to CLDN18.1. Preferably, an antibody having the ability of binding to CLDN18.2 is specific for CLDN18.2. Preferably, an antibody having the ability of binding to CLDN18.2 preferably is an antibody having the ability of binding to CLDN18.2 expressed on the cell surface. In particular preferred embodiments, an antibody having the ability of binding to CLDN18.2 binds to native epitopes of CLDN18.2 present on the surface of living cells. Preferably, an antibody having the ability of binding to CLDN18.2 binds to one or more peptides selected from the group consisting of SEQ ID NOs: 1, 3-11, 44, 46, and 48-50. Preferably, an antibody having the ability of binding to CLDN18.2 is specific for the afore mentioned proteins, peptides or immunogenic fragments or derivatives thereof. An antibody having the ability of binding to CLDN18.2 may be obtained by a method comprising the step of immunizing an animal with a protein or peptide comprising an amino acid sequence selected from the group consisting of SEQ ID NOs: 1, 3-11, 44, 46, and 48-50, or a nucleic acid or host cell expressing said protein or peptide. Preferably, the antibody binds to cancer cells, in particular cells of the cancer types mentioned above and, preferably, does not bind substantially to non-cancerous cells.

Preferably, binding of an antibody having the ability of binding to CLDN18.2 to cells expressing CLDN18.2 induces or mediates killing of cells expressing CLDN18.2. The cells expressing CLDN18.2 are preferably cancer cells and are, in particular, selected from the group consisting of tumorigenic gastric, esophageal, pancreatic, lung, ovarian, colon, hepatic, head-neck, and gallbladder cancer cells. Preferably, the antibody induces or mediates killing of cells by inducing one or more of complement dependent cytotoxicity (CDC) mediated lysis, antibody dependent cellular cytotoxicity (ADCC) mediated lysis, apoptosis, and inhibition of proliferation of cells expressing CLDN18.2. Preferably, ADCC mediated lysis of cells takes place in the presence of effector cells, which in particular embodiments are selected from the group consisting of monocytes, mononuclear cells, NK cells and PMNs. Inhibiting proliferation of cells can be measured in vitro by determining proliferation of cells in an assay using bromodeoxyuridine (5-bromo-2-deoxyuridine, BrdU). BrdU is a synthetic nucleoside which is an analogue of thymidine and can be incorporated into the newly synthesized DNA of replicating cells (during the S phase of the cell cycle), substituting for thymidine during DNA replication. Detecting the incorporated chemical using, for example, antibodies specific for BrdU indicates cells that were actively replicating their DNA.

In preferred embodiments, antibodies described herein can be characterized by one or more of the following properties:
a) specificity for CLDN18.2;
b) a binding affinity to CLDN18.2 of about 100 nM or less, preferably, about 5-10 nM or less and, more preferably, about 1-3 nM or less,
c) the ability to induce or mediate CDC on CLDN18.2 positive cells;
d) the ability to induce or mediate ADCC on CLDN18.2 positive cells;
e) the ability to inhibit the growth of CLDN18.2 positive cells;
f) the ability to induce apoptosis of CLDN18.2 positive cells.

hybridoma deposited at the DSMZ (Mascheroder Weg 1b, 31824 Braunschweig, Germany; new address: Inhoffenstr. 7B, 31824 Braunschweig, Germany) and having the following designation and accession number:
a. 182-D1106-055, accession no. DSM ACC2737, deposited on Oct. 19, 2005
b. 182-D1106-056, accession no. DSM ACC2738, deposited on Oct. 19, 2005
c. 182-D1106-057, accession no. DSM ACC2739, deposited on Oct. 19, 2005
d. 182-D1106-058, accession no. DSM ACC2740, deposited on Oct. 19, 2005
e. 182-D1106-059, accession no. DSM ACC2741, deposited on Oct. 19, 2005
f. 182-D1106-062, accession no. DSM ACC2742, deposited on Oct. 19, 2005,
g. 182-D1106-067, accession no. DSM ACC2743, deposited on Oct. 19, 2005
h. 182-D758-035, accession no. DSM ACC2745, deposited on Nov. 17, 2005
i. 182-D758-036, accession no. DSM ACC2746, deposited on Nov. 17, 2005
j. 182-D758-040, accession no. DSM ACC2747, deposited on Nov. 17, 2005
k. 182-D1106-061, accession no. DSM ACC2748, deposited on Nov. 17, 2005
l. 182-D1106-279, accession no. DSM ACC2808, deposited on Oct. 26, 2006
m. 182-D1106-294, accession no. DSM ACC2809, deposited on Oct. 26, 2006,
n. 182-D1106-362, accession no. DSM ACC2810, deposited on Oct. 26, 2006.

Preferred antibodies according to the invention are those produced by and obtainable from the above-described hybridomas; i.e. 37G11 in the case of 182-D1106-055, 37H8 in the case of 182-D1106-056, 38G5 in the case of 182-D1106-057, 38H3 in the case of 182-D1106-058, 39F11 in the case of 182-D1106-059, 43A11 in the case of 182-D1106-062, 61C2 in the case of 182-D1106-067, 26B5 in the case of 182-D758-035, 26D12 in the case of 182-D758-036, 28D10 in the case of 182-D758-040, 42E12 in the case of 182-D1106-061, 125E1 in the case of 182-D1106-279, 163E12 in the case of 182-D1106-294, and 175D10 in the case of 182-D1106-362; and the chimerized and humanized forms thereof.

Preferred chimerized antibodies and their sequences are shown in the following table.

|  | clone | mAb | Isotype | variable region | chimerized antibody |
|---|---|---|---|---|---|
| heavy chain | 43A11 | 182-D1106-062 | IgG2a | SEQ ID NO: 29 | SEQ ID NO: 14 |
|  | 163E12 | 182-D1106-294 | IgG3 | SEQ ID NO: 30 | SEQ ID NO: 15 |
|  | 125E1 | 182-D1106-279 | IgG2a | SEQ ID NO: 31 | SEQ ID NO: 16 |
|  | 166E2 | 182-D1106-308 | IgG3 | SEQ ID NO: 33 | SEQ ID NO: 18 |
|  | 175D10 | 182-D1106-362 | IgG1 | SEQ ID NO: 32 | SEQ ID NO: 17 |
|  | 45C1 | 182-D758-187 | IgG2a | SEQ ID NO: 34 | SEQ ID NO: 19 |
| light chain | 43A11 | 182-D1106-062 | IgK | SEQ ID NO: 36 | SEQ ID NO: 21 |
|  | 163E12 | 182-D1106-294 | IgK | SEQ ID NO: 35 | SEQ ID NO: 20 |
|  | 125E1 | 182-D1106-279 | IgK | SEQ ID NO: 37 | SEQ ID NO: 22 |
|  | 166E2 | 182-D1106-308 | IgK | SEQ ID NO: 40 | SEQ ID NO: 25 |
|  | 175D10 | 182-D1106-362 | IgK | SEQ ID NO: 39 | SEQ ID NO: 24 |
|  | 45C1 | 182-D758-187 | IgK | SEQ ID NO: 38 | SEQ ID NO: 23 |
|  | 45C1 | 182-D758-187 | IgK | SEQ ID NO: 41 | SEQ ID NO: 26 |
|  | 45C1 | 182-D758-187 | IgK | SEQ ID NO: 42 | SEQ ID NO: 27 |
|  | 45C1 | 182-D758-187 | IgK | SEQ ID NO: 43 | SEQ ID NO: 28 |

In a particularly preferred embodiment, an antibody having the ability of binding to CLDN18.2 is produced by a In preferred embodiments, antibodies, in particular chimerised forms of antibodies according to the invention include antibodies comprising a heavy chain constant region (CH) comprising an amino acid sequence derived from a human heavy chain constant region such as the amino acid sequence represented by SEQ ID NO: 13 or a fragment thereof. In further preferred embodiments, antibodies, in particular chimerised forms of antibodies according to the invention include antibodies comprising a light chain constant region (CL) comprising an amino acid sequence derived from a human light chain constant region such as the amino acid sequence represented by SEQ ID NO: 12 or a fragment thereof. In a particular preferred embodiment, antibodies, in particular chimerised forms of antibodies according to the invention include antibodies which comprise a CH comprising an amino acid sequence derived from a human CH such as the amino acid sequence represented by SEQ ID NO: 13 or a fragment thereof and which comprise a CL comprising an amino acid sequence derived from a human CL such as the amino acid sequence represented by SEQ ID NO: 12 or a fragment thereof.

In one embodiment, an antibody having the ability of binding to CLDN18.2 is a chimeric mouse/human IgG1 monoclonal antibody comprising kappa, murine variable light chain, human kappa light chain constant region allotype Km(3), murine heavy chain variable region, human IgG1 constant region, allotype G1m(3).

In certain preferred embodiments, chimerised forms of antibodies include antibodies comprising a heavy chain comprising an amino acid sequence selected from the group consisting of SEQ ID NOs: 14, 15, 16, 17, 18, 19, and a fragment thereof and/or comprising a light chain comprising an amino acid sequence selected from the group consisting of SEQ ID NOs: 20, 21, 22, 23, 24, 25, 26, 27, 28, and a fragment thereof.

In certain preferred embodiments, chimerised forms of antibodies include antibodies comprising a combination of heavy chains and light chains selected from the following possibilities (i) to (ix):
(i) the heavy chain comprises an amino acid sequence represented by SEQ ID NO: 14 or a fragment thereof and the light chain comprises an amino acid sequence represented by SEQ ID NO: 21 or a fragment thereof,
(ii) the heavy chain comprises an amino acid sequence represented by SEQ ID NO: 15 or a fragment thereof and the light chain comprises an amino acid sequence represented by SEQ ID NO: 20 or a fragment thereof,
(iii) the heavy chain comprises an amino acid sequence represented by SEQ ID NO: 16 or a fragment thereof and the light chain comprises an amino acid sequence represented by SEQ ID NO: 22 or a fragment thereof,
(iv) the heavy chain comprises an amino acid sequence represented by SEQ ID NO: 18 or a fragment thereof and the light chain comprises an amino acid sequence represented by SEQ ID NO: 25 or a fragment thereof,
(v) the heavy chain comprises an amino acid sequence represented by SEQ ID NO: 17 or a fragment thereof and the light chain comprises an amino acid sequence represented by SEQ ID NO: 24 or a fragment thereof,
(vi) the heavy chain comprises an amino acid sequence represented by SEQ ID NO: 19 or a fragment thereof and the light chain comprises an amino acid sequence represented by SEQ ID NO: 23 or a fragment thereof,
(vii) the heavy chain comprises an amino acid sequence represented by SEQ ID NO: 19 or a fragment thereof and the light chain comprises an amino acid sequence represented by SEQ ID NO: 26 or a fragment thereof,
(viii) the heavy chain comprises an amino acid sequence represented by SEQ ID NO: 19 or a fragment thereof and the light chain comprises an amino acid sequence represented by SEQ ID NO: 27 or a fragment thereof, and
(ix) the heavy chain comprises an amino acid sequence represented by SEQ ID NO: 19 or a fragment thereof and the light chain comprises an amino acid sequence represented by SEQ ID NO: 28 or a fragment thereof.

The antibody according to (v) is particularly preferred.

"Fragment" or "fragment of an amino acid sequence" as used above relates to a part of an antibody sequence, i.e. a sequence which represents the antibody sequence shortened at the N- and/or C-terminus, which when it replaces said antibody sequence in an antibody retains binding of said antibody to CLDN18.2 and preferably functions of said antibody as described herein, e.g. CDC mediated lysis or ADCC mediated lysis. Preferably, a fragment of an amino acid sequence comprises at least 80%, preferably at least 90%, 95%, 96%, 97%, 98%, or 99% of the amino acid residues from said amino acid sequence. A fragment of an amino acid sequence selected from the group consisting of SEQ ID NOs: 14, 15, 16, 17, 18, 19, 20, 21, 22, 23, 24, 25, 26, 27, and 28 preferably relates to said sequence wherein 17, 18, 19, 20, 21, 22 or 23 amino acids at the N-terminus are removed.

In a preferred embodiment, an antibody having the ability of binding to CLDN18.2 comprises a heavy chain variable region (VH) comprising an amino acid sequence selected from the group consisting of SEQ ID NOs: 29, 30, 31, 32, 33, 34, and a fragment thereof.

In a preferred embodiment, an antibody having the ability of binding to CLDN18.2 comprises a light chain variable region (VL) comprising an amino acid sequence selected from the group consisting of SEQ ID NO: 35, 36, 37, 38, 39, 40, 41, 42, 43, and a fragment thereof.

In certain preferred embodiments, an antibody having the ability of binding to CLDN18.2 comprises a combination of heavy chain variable region (VH) and light chain variable region (VL) selected from the following possibilities (i) to (ix):
(i) the VH comprises an amino acid sequence represented by SEQ ID NO: 29 or a fragment thereof and the VL comprises an amino acid sequence represented by SEQ ID NO: 36 or a fragment thereof,
(ii) the VH comprises an amino acid sequence represented by SEQ ID NO: 30 or a fragment thereof and the VL comprises an amino acid sequence represented by SEQ ID NO: 35 or a fragment thereof,
(iii) the VH comprises an amino acid sequence represented by SEQ ID NO: 31 or a fragment thereof and the VL comprises an amino acid sequence represented by SEQ ID NO: 37 or a fragment thereof,
(iv) the VH comprises an amino acid sequence represented by SEQ ID NO: 33 or a fragment thereof and the VL comprises an amino acid sequence represented by SEQ ID NO: 40 or a fragment thereof,
(v) the VH comprises an amino acid sequence represented by SEQ ID NO: 32 or a fragment thereof and the VL comprises an amino acid sequence represented by SEQ ID NO: 39 or a fragment thereof,
(vi) the VH comprises an amino acid sequence represented by SEQ ID NO: 34 or a fragment thereof and the VL comprises an amino acid sequence represented by SEQ ID NO: 38 or a fragment thereof,
(vii) the VH comprises an amino acid sequence represented by SEQ ID NO: 34 or a fragment thereof and the VL comprises an amino acid sequence represented by SEQ ID NO: 41 or a fragment thereof, (viii) the VH comprises an amino acid sequence represented by SEQ ID NO: 34 or a fragment thereof and the VL comprises an amino acid sequence represented by SEQ ID NO: 42 or a fragment thereof, (ix) the VH comprises an amino acid sequence represented by SEQ ID NO: 34 or a fragment thereof and the VL comprises an amino acid sequence represented by SEQ ID NO: 43 or a fragment thereof.

The antibody according to (v) is particularly preferred.

In a preferred embodiment, an antibody having the ability of binding to CLDN18.2 comprises a VH comprising a set of complementarity-determining regions CDR1, CDR2 and CDR3 selected from the following embodiments (i) to (vi):

(i) CDR1: positions 45-52 of SEQ ID NO: 14, CDR2: positions 70-77 of SEQ ID NO: 14, CDR3: positions 116-125 of SEQ ID NO: 14, (ii) CDR1: positions 45-52 of SEQ ID NO: 15, CDR2: positions 70-77 of SEQ ID NO: 15, CDR3: positions 116-126 of SEQ ID NO: 15, (iii) CDR1: positions 45-52 of SEQ ID NO: 16, CDR2: positions 70-77 of SEQ ID NO: 16, CDR3: positions 116-124 of SEQ ID NO: 16, (iv) CDR1: positions 45-52 of SEQ ID NO: 17, CDR2: positions 70-77 of SEQ ID NO: 17, CDR3: positions 116-126 of SEQ ID NO: 17, (v) CDR1: positions 44-51 of SEQ ID NO: 18, CDR2: positions 69-76 of SEQ ID NO: 18, CDR3: positions 115-125 of SEQ ID NO: 18, and (vi) CDR1: positions 45-53 of SEQ ID NO: 19, CDR2: positions 71-78 of SEQ ID NO: 19, CDR3: positions 117-128 of SEQ ID NO: 19.

In a preferred embodiment, an antibody having the ability of binding to CLDN18.2 comprises a VL comprising a set of complementarity-determining regions CDR1, CDR2 and CDR3 selected from the following embodiments (i) to (ix):

(i) CDR1: positions 47-58 of SEQ ID NO: 20, CDR2: positions 76-78 of SEQ ID NO: 20, CDR3: positions 115-123 of SEQ ID NO: 20, (ii) CDR1: positions 49-53 of SEQ ID NO: 21, CDR2: positions 71-73 of SEQ ID NO: 21, CDR3: positions 110-118 of SEQ ID NO: 21, (iii) CDR1: positions 47-52 of SEQ ID NO: 22, CDR2: positions 70-72 of SEQ ID NO: 22, CDR3: positions 109-117 of SEQ ID NO: 22, (iv) CDR1: positions 47-58 of SEQ ID NO: 23, CDR2: positions 76-78 of SEQ ID NO: 23, CDR3: positions 115-123 of SEQ ID NO: 23, (v) CDR1: positions 47-58 of SEQ ID NO: 24, CDR2: positions 76-78 of SEQ ID NO: 24, CDR3: positions 115-123 of SEQ ID NO: 24, (vi) CDR1: positions 47-58 of SEQ ID NO: 25, CDR2: positions 76-78 of SEQ ID NO: 25, CDR3: positions 115-122 of SEQ ID NO: 25, (vii) CDR1: positions 47-58 of SEQ ID NO: 26, CDR2: positions 76-78 of SEQ ID NO: 26, CDR3: positions 115-123 of SEQ ID NO: 26, (viii) CDR1: positions 47-58 of SEQ ID NO: 27, CDR2: positions 76-78 of SEQ ID NO: 27, CDR3: positions 115-123 of SEQ ID NO: 27, and (ix) CDR1: positions 47-52 of SEQ ID NO: 28, CDR2: positions 70-72 of SEQ ID NO: 28, CDR3: positions 109-117 of SEQ ID NO: 28.

In a preferred embodiment, an antibody having the ability of binding to CLDN18.2 comprises a combination of VH and VL each comprising a set of complementarity-determining regions CDR1, CDR2 and CDR3 selected from the following embodiments (i) to (ix):

(i) VH: CDR1: positions 45-52 of SEQ ID NO: 14, CDR2: positions 70-77 of SEQ ID NO: 14, CDR3: positions 116-125 of SEQ ID NO: 14, VL: CDR1: positions 49-53 of SEQ ID NO: 21, CDR2: positions 71-73 of SEQ ID NO: 21, CDR3: positions 110-118 of SEQ ID NO: 21, (ii) VH: CDR1: positions 45-52 of SEQ ID NO: 15, CDR2: positions 70-77 of SEQ ID NO: 15, CDR3: positions 116-126 of SEQ ID NO: 15, VL: CDR1: positions 47-58 of SEQ ID NO: 20, CDR2: positions 76-78 of SEQ ID NO: 20, CDR3: positions 115-123 of SEQ ID NO: 20, (iii) VH: CDR1: positions 45-52 of SEQ ID NO: 16, CDR2: positions 70-77 of SEQ ID NO: 16, CDR3: positions 116-124 of SEQ ID NO: 16, VL: CDR1: positions 47-52 of SEQ ID NO: 22, CDR2: positions 70-72 of SEQ ID NO: 22, CDR3: positions 109-117 of SEQ ID NO: 22, (iv) VH: CDR1: positions 44-51 of SEQ ID NO: 18, CDR2: positions 69-76 of SEQ ID NO: 18, CDR3: positions 115-125 of SEQ ID NO: 18, VL: CDR1: positions 47-58 of SEQ ID NO: 25, CDR2: positions 76-78 of SEQ ID NO: 25, CDR3: positions 115-122 of SEQ ID NO: 25, (v) VH: CDR1: positions 45-52 of SEQ ID NO: 17, CDR2: positions 70-77 of SEQ ID NO: 17, CDR3: positions 116-126 of SEQ ID NO: 17, VL: CDR1: positions 47-58 of SEQ ID NO: 24, CDR2: positions 76-78 of SEQ ID NO: 24, CDR3: positions 115-123 of SEQ ID NO: 24, (vi) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-58 of SEQ ID NO: 23, CDR2: positions 76-78 of SEQ ID NO: 23, CDR3: positions 115-123 of SEQ ID NO: 23, (vii) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-58 of SEQ ID NO: 26, CDR2: positions 76-78 of SEQ ID NO: 26, CDR3: positions 115-123 of SEQ ID NO: 26, (viii) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-58 of SEQ ID NO: 27, CDR2: positions 76-78 of SEQ ID NO: 27, CDR3: positions 115-123 of SEQ ID NO: 27, and (ix) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-52 of SEQ ID NO: 28, CDR2: positions 70-72 of SEQ ID NO: 28, CDR3: positions 109-117 of SEQ ID NO: 28.

In further preferred embodiments, an antibody having the ability of binding to CLDN18.2 preferably comprises one or more of the complementarity-determining regions (CDRs), preferably at least the CDR3 variable region, of the heavy chain variable region (VH) and/or of the light chain variable region (VL) of a monoclonal antibody against CLDN18.2, preferably of a monoclonal antibody against CLDN18.2 described herein, and preferably comprises one or more of the complementarity-determining regions (CDRs), preferably at least the CDR3 variable region, of the heavy chain variable regions (VH) and/or light chain variable regions (VL) described herein. In one embodiment said one or more of the complementarity-determining regions (CDRs) are selected from a set of complementarity-determining regions CDR1, CDR2 and CDR3 described herein. In a particularly preferred embodiment, an antibody having the ability of binding to CLDN18.2 preferably comprises the complementarity-determining regions CDR1, CDR2 and CDR3 of the heavy chain variable region (VH) and/or of the light chain variable region (VL) of a monoclonal antibody against CLDN18.2, preferably of a monoclonal antibody against CLDN18.2 described herein, and preferably comprises the complementarity-determining regions CDR1, CDR2 and CDR3 of the heavy chain variable regions (VH) and/or light chain variable regions (VL) described herein.

In one embodiment an antibody comprising one or more CDRs, a set of CDRs or a combination of sets of CDRs as described herein comprises said CDRs together with their intervening framework regions. Preferably, the portion will also include at least about 50% of either or both of the first and fourth framework regions, the 50% being the C-terminal 50% of the first framework region and the N-terminal 50% of the fourth framework region. Construction of antibodies made by recombinant DNA techniques may result in the introduction of residues N- or C-terminal to the variable regions encoded by linkers introduced to facilitate cloning or other manipulation steps, including the introduction of linkers to join variable regions of the invention to further protein sequences including immunoglobulin heavy chains, other variable domains (for example in the production of diabodies) or protein labels.

In one embodiment an antibody comprising one or more CDRs, a set of CDRs or a combination of sets of CDRs as described herein comprises said CDRs in a human antibody framework.

Reference herein to an antibody comprising with respect to the heavy chain thereof a particular chain, or a particular region or sequence preferably relates to the situation wherein all heavy chains of said antibody comprise said particular chain, region or sequence. This applies correspondingly to the light chain of an antibody.

The term "nucleic acid", as used herein, is intended to include DNA and RNA. A nucleic acid may be single-stranded or double-stranded, but preferably is double-stranded DNA.

According to the invention, the term "expression" is used in its most general meaning and comprises the production of RNA or of RNA and protein/peptide. It also comprises partial expression of nucleic acids. Furthermore, expression may be carried out transiently or stably.

The teaching given herein with respect to specific amino acid sequences, e.g. those shown in the sequence listing, is to be construed so as to also relate to variants of said specific sequences resulting in sequences which are functionally equivalent to said specific sequences, e.g. amino acid sequences exhibiting properties identical or similar to those of the specific amino acid sequences. One important property is to retain binding of an antibody to its target or to sustain effector functions of an antibody. Preferably, a sequence which is a variant with respect to a specific sequence, when it replaces the specific sequence in an antibody retains binding of said antibody to CLDN18.2 and preferably functions of said antibody as described herein, e.g. CDC mediated lysis or ADCC mediated lysis.

It will be appreciated by those skilled in the art that in particular the sequences of the CDR, hypervariable and variable regions can be modified without losing the ability to bind CLDN18.2. For example, CDR regions will be either identical or highly homologous to the regions of antibodies specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions of antibodies specifically disclosed herein.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

The term "transgenic animal" refers to an animal having a genome comprising one or more transgenes, preferably heavy and/or light chain transgenes, or transchromosomes (either integrated or non-integrated into the animal's natural genomic DNA) and which is preferably capable of expressing the transgenes. For example, a transgenic mouse can have a human light chain transgene and either a human heavy chain transgene or human heavy chain transchromosome, such that the mouse produces human anti-CLDN18.2 antibodies when immunized with CLDN18.2 antigen and/or cells expressing CLDN18.2. The human heavy chain transgene can be integrated into the chromosomal DNA of the mouse, as is the case for transgenic mice, e.g., HuMAb mice, such as HCo7 or HCo12 mice, or the human heavy chain transgene can be maintained extrachromosomally, as is the case for transchromosomal (e.g., KM) mice as described in WO 02/43478. Such transgenic and transchromosomal mice may be capable of producing multiple isotypes of human monoclonal antibodies to CLDN18.2 (e.g., IgG, IgA and/or IgE) by undergoing V-D-J recombination and isotype switching.

"Reduce", "decrease" or "inhibit" as used herein means an overall decrease or the ability to cause an overall decrease, preferably of 5% or greater, 10% or greater, 20% or greater, more preferably of 50% or greater, and most preferably of 75% or greater, in the level, e.g. in the level of expression or in the level of proliferation of cells.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%, at least 200%, at least 500%, at least 1000%, at least 10000% or even more.

Mechanisms of mAb Action

Although the following provides considerations regarding the mechanism underlying the therapeutic efficacy of antibodies of the invention it is not to be considered as limiting to the invention in any way.

The antibodies described herein preferably interact with components of the immune system, preferably through ADCC or CDC. Antibodies described herein can also be used to target payloads (e.g., radioisotopes, drugs or toxins) to directly kill tumor cells or can be used synergistically with traditional chemotherapeutic agents, attacking tumors through complementary mechanisms of action that may include anti-tumor immune responses that may have been compromised owing to a chemotherapeutic's cytotoxic side effects on T lymphocytes. However, antibodies described herein may also exert an effect simply by binding to CLDN18.2 on the cell surface, thus, e.g. blocking proliferation of the cells.

Antibody-Dependent Cell-Mediated Cytotoxicity

ADCC describes the cell-killing ability of effector cells as described herein, in particular lymphocytes, which preferably requires the target cell being marked by an antibody.

ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that leads to antigen presentation and the induction of tumor-directed T-cell responses. Preferably, in vivo induction of ADCC will lead to tumor-directed T-cell responses and host-derived antibody responses.

Complement-Dependent Cytotoxicity

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the $C_H2$ domains of participating antibody molecules such as IgG molecules (C1q is one of three subcomponents of complement C1). Preferably these uncloaked C1q binding sites convert the previously low-affinity C1 q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell.

Antibodies described herein can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl.

Acad. Sci. U.S.A. 92:9348 (1995), see also Rossi et al., Am. J. Clin. Pathol. 124: 295 (2005)).

In yet another preferred embodiment, human monoclonal antibodies can be generated using transgenic or transchromosomal mice carrying parts of the human immune system rather than the mouse system. These transgenic and transchromosomic mice include mice known as HuMAb mice and KM mice, respectively, and are collectively referred to herein as "transgenic mice." The production of human antibodies in such transgenic mice can be performed as described in detail for CD20 in WO2004 035607

Yet another strategy for generating monoclonal antibodies is to directly isolate genes encoding antibodies from lymphocytes producing antibodies of defined specificity e.g. see Babcock et al., 1996; A novel strategy for generating monoclonal antibodies from single, isolated lymphocytes producing antibodies of defined specificities. For details of recombinant antibody engineering see also Welschof and Kraus, Recombinant antibodies for cancer therapy ISBN-0-89603-918-8 and Benny K. C. Lo Antibody Engineering ISBN 1-58829-092-1.

To generate antibodies, mice can be immunized with carrier-conjugated peptides derived from the antigen sequence, i.e. the sequence against which the antibodies are to be directed, an enriched preparation of recombinantly expressed antigen or fragments thereof and/or cells expressing the antigen, as described. Alternatively, mice can be immunized with DNA encoding the antigen or fragments thereof. In the event that immunizations using a purified or enriched preparation of the antigen do not result in antibodies, mice can also be immunized with cells expressing the antigen, e.g., a cell line, to promote immune responses.

The immune response can be monitored over the course of the immunization protocol with plasma and serum samples being obtained by tail vein or retroorbital bleeds. Mice with sufficient titers of immunoglobulin can be used for fusions. Mice can be boosted intraperitoneally or intravenously with antigen expressing cells 3 days before sacrifice and removal of the spleen to increase the rate of specific antibody secreting hybridomas.

To generate hybridomas producing monoclonal antibodies, splenocytes and lymph node cells from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using antigen expressing cells, antibodies with specificity for the antigen can be identified. The antibody secreting hybridomas can be replated, screened again, and if still positive for monoclonal antibodies can be subcloned by limiting dilution. The stable subclones can then be cultured in vitro to generate antibody in tissue culture medium for characterization.

Antibodies also can be produced in a host cell transfectoma using, for example, a combination of recombinant DNA techniques and gene transfection methods as are well known in the art (Morrison, S. (1985) Science 229: 1202).

For example, in one embodiment, the gene(s) of interest, e.g., antibody genes, can be ligated into an expression vector such as a eukaryotic expression plasmid such as used by the GS gene expression system disclosed in WO 87/04462, WO 89/01036 and EP 338 841 or other expression systems well known in the art. The purified plasmid with the cloned antibody genes can be introduced in eukaryotic host cells such as CHO cells, NS/0 cells, HEK293T cells or HEK293 cells or alternatively other eukaryotic cells like plant derived cells, fungal or yeast cells. The method used to introduce these genes can be methods described in the art such as electroporation, lipofectine, lipofectamine or others. After introduction of these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively, the cloned antibody genes can be expressed in other expression systems, including prokaryotic cells, such as microorganisms, e.g. *E. coli*. Furthermore, the antibodies can be produced in transgenic non-human animals, such as in milk from sheep and rabbits or in eggs from hens, or in transgenic plants; see e.g. Verma, R., et al. (1998) J. Immunol. Meth. 216: 165-181; Pollock, et al. (1999) J. Immunol. Meth. 231: 147-157; and Fischer, R., et al. (1999) Biol. Chem. 380: 825-839.

Chimerization

Murine monoclonal antibodies can be used as therapeutic antibodies in humans when labeled with toxins or radioactive isotopes. Nonlabeled murine antibodies are highly immunogenic in man when repetitively applied leading to reduction of the therapeutic effect. The main immunogenicity is mediated by the heavy chain constant regions. The immunogenicity of murine antibodies in man can be reduced or completely avoided if respective antibodies are chimerized or humanized. Chimeric antibodies are antibodies, the different portions of which are derived from different animal species, such as those having a variable region derived from a murine antibody and a human immunoglobulin constant region. Chimerisation of antibodies is achieved by joining of the variable regions of the murine antibody heavy and light chain with the constant region of human heavy and light chain (e.g. as described by Kraus et al., in Methods in Molecular Biology series, Recombinant antibodies for cancer therapy ISBN-0-89603-918-8). In a preferred embodiment chimeric antibodies are generated by joining human kappa-light chain constant region to murine light chain variable region. In an also preferred embodiment chimeric antibodies can be generated by joining human lambda-light chain constant region to murine light chain variable region. The preferred heavy chain constant regions for generation of chimeric antibodies are IgG1, IgG3 and IgG4. Other preferred heavy chain constant regions for generation of chimeric antibodies are IgG2, IgA, IgD and IgM.

Humanization

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332: 323-327; Jones, P. et al. (1986) Nature 321: 522-525; and Queen, C. et al. (1989) Proc. Natl. Acad. Sci. U.S.A. 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual evenly across the variable region.

The ability of antibodies to bind an antigen can be determined using standard binding assays (e.g., ELISA, Western Blot, Immunofluorescence and flow cytometric analysis).

To purify antibodies, selected hybridomas can be grown in two-liter spinner-flasks for monoclonal antibody purification. Alternatively, antibodies can be produced in dialysis based bioreactors. Supernatants can be filtered and, if necessary, concentrated before affinity chromatography with protein G-sepharose or protein A-sepharose. Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected monoclonal antibodies bind to unique epitopes, site-directed or multi-site directed mutagenesis can be used.

To determine the isotype of antibodies, isotype ELISAs with various commercial kits (e.g. Zymed, Roche Diagnostics) can be performed. Wells of microtiter plates can be coated with anti-mouse Ig. After blocking, the plates are reacted with monoclonal antibodies or purified isotype controls, at ambient temperature for two hours. The wells can then be reacted with either mouse IgG1, IgG2a, IgG2b or IgG3, IgA or mouse IgM-specific peroxidase-conjugated probes. After washing, the plates can be developed with ABTS substrate (1 mg/ml) and analyzed at OD of 405-650. Alternatively, the IsoStrip Mouse Monoclonal Antibody Isotyping Kit (Roche, Cat. No. 1493027) may be used as described by the manufacturer.

In order to demonstrate presence of antibodies in sera of immunized mice or binding of monoclonal antibodies to living cells expressing antigen, flow cytometry can be used. Cell lines expressing naturally or after transfection antigen and negative controls lacking antigen expression (grown under standard growth conditions) can be mixed with various concentrations of monoclonal antibodies in hybridoma supernatants or in PBS containing 1% FBS, and can be incubated at 4° C. for 30 min.

After washing, the APC- or Alexa647-labeled anti IgG antibody can bind to antigen-bound monoclonal antibody under the same conditions as the primary antibody staining. The samples can be analyzed by flow cytometry with a FACS instrument using light and side scatter properties to gate on single, living cells. In order to distinguish antigen-specific monoclonal antibodies from nonspecific binders in a single measurement, the method of co-transfection can be employed. Cells transiently transfected with plasmids encoding antigen and a fluorescent marker can be stained as described above. Transfected cells can be detected in a different fluorescence channel than antibody-stained cells. As the majority of transfected cells express both transgenes, antigen-specific monoclonal antibodies bind preferentially to fluorescence marker expressing cells, whereas nonspecific antibodies bind in a comparable ratio to non-transfected cells. An alternative assay using fluorescence microscopy may be used in addition to or instead of the flow cytometry assay. Cells can be stained exactly as described above and examined by fluorescence microscopy.

In order to demonstrate presence of antibodies in sera of immunized mice or binding of monoclonal antibodies to living cells expressing antigen, immunofluorescence microscopy analysis can be used. For example, cell lines expressing either spontaneously or after transfection antigen and negative controls lacking antigen expression are grown in chamber slides under standard growth conditions in DMEM/F12 medium, supplemented with 10% fetal calf serum (FCS), 2 mM L-glutamine, 100 IU/ml penicillin and 100 μg/ml streptomycin. Cells can then be fixed with methanol or paraformaldehyde or left untreated. Cells can then be reacted with monoclonal antibodies against the antigen for 30 min. at 25° C. After washing, cells can be reacted with an Alexa555-labelled anti-mouse IgG secondary antibody (Molecular Probes) under the same conditions. Cells can then be examined by fluorescence microscopy.

Cell extracts from cells expressing antigen and appropriate negative controls can be prepared and subjected to sodium dodecyl sulfate (SDS) polyacrylamide gel electrophoresis. After electrophoresis, the separated antigens will be transferred to nitrocellulose membranes, blocked, and probed with the monoclonal antibodies to be tested. IgG binding can be detected using anti-mouse IgG peroxidase and developed with ECL substrate.

Antibodies can be further tested for reactivity with antigen by Immunohistochemistry in a manner well known to the skilled person, e.g. using paraformaldehyde or acetone fixed cryosections or paraffin embedded tissue sections fixed with paraformaldehyde from non-cancer tissue or cancer tissue samples obtained from patients during routine surgical procedures or from mice carrying xenografted tumors inoculated with cell lines expressing spontaneously or after transfection antigen. For immunostaining, antibodies reactive to antigen can be incubated followed by horseradish-peroxidase conjugated goat anti-mouse or goat anti-rabbit antibodies (DAKO) according to the vendors instructions.

Antibodies can be tested for their ability to mediate phagocytosis and killing of cells expressing CLDN18.2. The testing of monoclonal antibody activity in vitro will provide an initial screening prior to testing in vivo models.

Antibody Dependent Cell-Mediated Cytotoxicity (ADCC):

Briefly, polymorphonuclear cells (PMNs), NK cells, monocytes, mononuclear cells or other effector cells, from healthy donors can be purified by Ficoll Hypaque density centrifugation, followed by lysis of contaminating erythrocytes. Washed effector cells can be suspended in RPMI supplemented with 10% heat-inactivated fetal calf serum or, alternatively with 5% heat-inactivated human serum and mixed with $^{51}$Cr labeled target cells expressing CLDN18.2, at various ratios of effector cells to target cells. Alternatively, the target cells may be labeled with a fluorescence enhancing ligand (BATDA). A highly fluorescent chelate of Europium with the enhancing ligand which is released from dead cells can be measured by a fluorometer. Another alternative technique may utilize the transfection of target cells with luciferase. Added lucifer yellow may then be oxidated by viable cells only. Purified anti-CLDN18.2 IgGs can then be added at various concentrations. Irrelevant human IgG can be used as negative control. Assays can be carried out for 4 to 20 hours at 37° C. depending on the effector cell type used. Samples can be assayed for cytolysis by measuring $^{51}$Cr release or the presence of the EuTDA chelate in the culture supernatant. Alternatively, luminescence resulting from the oxidation of lucifer yellow can be a measure of viable cells.

Anti-CLDN18.2 monoclonal antibodies can also be tested in various combinations to determine whether cytolysis is enhanced with multiple monoclonal antibodies.

Complement Dependent Cytotoxicity (CDC):

Monoclonal anti-CLDN18.2 antibodies can be tested for their ability to mediate CDC using a variety of known techniques. For example, serum for complement can be obtained from blood in a manner known to the skilled person. To determine the CDC activity of mAbs, different methods can be used. $^{51}$Cr release can for example be measured or elevated membrane permeability can be assessed using a propidium iodide (PI) exclusion assay. Briefly, target cells can be washed and $5 \times 10^5$/ml can be incubated with various concentrations of mAb for 10-30 min. at room temperature or at 37° C. Serum or plasma can then be added to a final concentration of 20% (v/v) and the cells incubated at 37° C. for 20-30 min. All cells from each sample can be added to the PI solution in a FACS tube. The mixture can then be analyzed immediately by flow cytometry analysis using FACSArray.

In an alternative assay, induction of CDC can be determined on adherent cells. In one embodiment of this assay, cells are seeded 24 h before the assay with a density of $3 \times 10^4$/well in tissue-culture flat-bottom microtiter plates. The next day growth medium is removed and the cells are incubated in triplicates with antibodies. Control cells are incubated with growth medium or growth medium containing 0.2% saponin for the determination of background lysis and maximal lysis, respectively. After incubation for 20 min. at room temperature supernatant is removed and 20% (v/v) human plasma or serum in DMEM (prewarmed to 37° C.) is added to the cells and incubated for another 20 min. at 37° C. All cells from each sample are added to propidium iodide solution (10 µg/ml). Then, supernatants are replaced by PBS containing 2.5 µg/ml ethidium bromide and fluorescence emission upon excitation at 520 nm is measured at 600 nm using a Tecan Safire. The percentage specific lysis is calculated as follows: % specific lysis=(fluorescence sample-fluorescence background)/(fluorescence maximal lysis-fluorescence background)×100.

Induction of Apoptosis and Inhibition of Cell Proliferation by Monoclonal Antibodies:

To test for the ability to initiate apoptosis, monoclonal anti-CLDN18.2 antibodies can, for example, be incubated with CLDN18.2 positive tumor cells, e.g., SNU-16, DAN-G, KATO-III or CLDN18.2 transfected tumor cells at 37° C. for about 20 hours. The cells can be harvested, washed in Annexin-V binding buffer (BD biosciences), and incubated with Annexin V conjugated with FITC or APC (BD biosciences) for 15 min. in the dark. All cells from each sample can be added to PI solution (10 µg/ml in PBS) in a FACS tube and assessed immediately by flow cytometry (as above). Alternatively, a general inhibition of cell-proliferation by monoclonal antibodies can be detected with commercially available kits. The DELFIA Cell Proliferation Kit (Perkin-Elmer, Cat. No. AD0200) is a non-isotopic immunoassay based on the measurement of 5-bromo-2'-deoxyuridine (BrdU) incorporation during DNA synthesis of proliferating cells in microplates. Incorporated BrdU is detected using europium labelled monoclonal antibody. To allow antibody detection, cells are fixed and DNA denatured using Fix solution. Unbound antibody is washed away and DELFIA inducer is added to dissociate europium ions from the labelled antibody into solution, where they form highly fluorescent chelates with components of the DELFIA Inducer. The fluorescence measured—utilizing time-resolved fluorometry in the detection—is proportional to the DNA synthesis in the cell of each well.

Preclinical Studies

Monoclonal antibodies which bind to CLDN18.2 also can be tested in an in vivo model (e.g. in immune deficient mice carrying xenografted tumors inoculated with cell lines expressing CLDN18.2, e.g. DAN-G, SNU-16, or KATO-III, or after transfection, e.g. HEK293) to determine their efficacy in controlling growth of CLDN18.2-expressing tumor cells.

In vivo studies after xenografting CLDN18.2 expressing tumor cells into immunocompromised mice or other animals can be performed using antibodies described herein. Antibodies can be administered to tumor free mice followed by injection of tumor cells to measure the effects of the antibodies to prevent formation of tumors or tumor-related symptoms. Antibodies can be administered to tumor-bearing mice to determine the therapeutic efficacy of respective antibodies to reduce tumor growth, metastasis or tumor related symptoms. Antibody application can be combined with application of other substances as cystostatic drugs, growth factor inhibitors, cell cycle blockers, angiogenesis inhibitors or other antibodies to determine synergistic efficacy and potential toxicity of combinations. To analyze toxic side effects mediated by antibodies animals can be inoculated with antibodies or control reagents and thoroughly investigated for symptoms possibly related to CLDN18.2-antibody therapy. Possible side effects of in vivo application of CLDN18.2 antibodies particularly include toxicity at CLDN18.2 expressing tissues including stomach. Antibodies recognizing CLDN18.2 in human and in other species, e.g. mice, are particularly useful to predict potential side effects mediated by application of monoclonal CLDN18.2-antibodies in humans.

Mapping of epitopes recognized by antibodies can be performed as described in detail in "Epitope Mapping Protocols (Methods in Molecular Biology) by Glenn E. Morris ISBN-089603-375-9 and in "Epitope Mapping: A Practical Approach" Practical Approach Series, 248 by Olwyn M. R. Westwood, Frank C. Hay.

The compounds and agents described herein may be administered in the form of any suitable pharmaceutical composition.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may used for preparing pharmaceutically acceptable salts and are included in the invention. Pharmaceutically acceptable salts of this kind comprise in a non limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

An injectable formulation may comprise a pharmaceutically acceptable excipient such as Ringer Lactate.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavoring agents, or colorants.

The agents and compositions described herein may be administered via any conventional route, such as by parenteral administration including by injection or infusion. Administration is preferably parenterally, e.g. intravenously, intraarterially, subcutaneously, intradermally or intramuscularly.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The agents and compositions described herein can be administered to patients, e.g., in vivo, to treat or prevent a variety of disorders such as those described herein. Preferred patients include human patients having disorders that can be corrected or ameliorated by administering the agents and compositions described herein. This includes disorders involving cells characterized by an altered expression pattern of CLDN18.2.

For example, in one embodiment, antibodies described herein can be used to treat a patient with a cancer disease, e.g., a cancer disease such as described herein characterized by the presence of cancer cells expressing CLDN18.2.

The pharmaceutical compositions and methods of treatment described according to the invention may also be used for immunization or vaccination to prevent a disease described herein.

The present invention is further illustrated by the following examples which are not be construed as limiting the scope of the invention.

EXAMPLES

Example 1: Clinical First-in-Human Single-Dose Multi-Center, Phase I, Open-Label, i.v. Infusion Escalation Study Evaluating the Safety and Tolerability of IMAB362 in Hospitalized Patients with Advanced Gastroesophageal Cancer A clinical first-in-human single-dose multi-center, phase I, open-label, i.v. infusion escalation study in humans with IMAB362 was performed to determine the maximum tolerated or applicable single dose (MTD) of IMAB362, examine the safety, tolerability and adverse event profile of IMAB362, determine the pharmacokinetics profile of single escalating doses of IMAB362, determine the immunogenicity of a single dose application of IMAB362, and determine the potential antitumor activity of IMAB362 in patients with advanced gastroesophageal (GE) cancer.

This study was designed as a first-in-human phase I, multi-center, non-randomized, inter-patient single-dose escalation, open-label clinical study with a single intravenous infusion of IMAB362 and a 4-week treatment free follow-up period.

To be included in the study, patients had to fulfill all of the following inclusion criteria:

Metastatic, refractory or recurrent disease of advanced gastroesophageal cancer proven by histology CLDN18.2 expression confirmed by immunohistochemistry or availability of a tissue sample of the tumor suitable for determination of CLDN18.2 expression Prior standard chemotherapy containing a fluoropyrimidine, a platinum compound and/or epirubicine, and—if clinically appropriate—docetaxel At least 1 measurable site of the disease according to RECIST criteria (Computer tomography (CT)-scans or Magnetic resonance tomography (MRT) not older than 6 weeks before study entry)

18 years of age or older

Written informed consent after being informed of the study

ECOG performance status (PS) 0-1 OR Karnofsky 70-100%

Life expectancy >3 months

Platelet count ≥100,000/mm$^3$

Hemoglobin ≥10 g/dl

INR <1.5

Bilirubin normal

AST and ALT <2.5 times upper limit of normal (ULN) (5 times ULN if liver metastases are present)

Creatinine <1.5×ULN

For women with childbearing potential (last menstruation less than 2 years prior to enrolment): Negative pregnancy test (β-HCG) at baseline and using two highly effective methods of contraception for 8 weeks after the infusion of the study drug Male patients must use an accepted contraceptive method for 8 weeks after the infusion of the study drug.

Patients presenting one or more of the following criteria were not to be included in the study:

Pregnancy or breastfeeding

Prior allergic reaction or intolerance to a monoclonal antibody, including humanized and chimeric antibodies Prior inclusion in the present study Less than 3 weeks since prior anti-tumor chemotherapy or radiotherapy Other investigational agents or devices concurrently or within 4 weeks prior to this study Other concurrent anticancer agents or therapies History of positive test for human immunodeficiency virus (HIV) antibody Known hepatitis Uncontrolled or severe illness including, but not limited to, any of the following:

Ongoing or active infection requiring parenteral antibiotics

Symptomatic congestive heart failure

Unstable angina pectoris

Uncontrolled hypertension

Clinically significant cardiac arrhythmia

Myocardial infarction within the past 6 months

Gastric bleeding within last four weeks

Symptomatic peptic ulcer

Clinical symptoms of cerebral metastasis or documented metastasis

Psychiatric illness or social situations that would preclude study compliance

Concurrent administration of anticoagulation agents with vitamin K antagonists (e.g. Coumadin)

Concurrent administration of therapeutic doses of heparin (prophylactic doses are acceptable).

From a total of 29 patients, 15 patients received study medication and were allocated to one of the dose cohorts (33, 100, 300, 600 or 1000 mg IMAB362/m$^2$). These patients formed the safety population (SP). As no potentially dose limiting toxicities occurred in any of the dose groups, no additional patients had to be tested to confirm potential dose limiting toxicities. Therefore, no more than 3 patients in each dose cohort, i.e. 15 patients overall, received study medication.

Patient allocation to the different IMAB362 dose cohorts is given in Table 1, below.

TABLE 1

Allocation of patients

| IMAB362 dose cohort | Patient no. |
|---|---|
| 33 mg/m$^2$ | 0201 |
|  | 0103 |
|  | 0104 |
| 100 mg/m$^2$ | 0202 |
|  | 0105 |
|  | 0203 |

TABLE 1-continued

Allocation of patients

| IMAB362 dose cohort | Patient no. |
|---|---|
| 300 mg/m$^2$ | 1101 |
|  | 0403 |
|  | 1201 |
| 600 mg/m$^2$ | 0302 |
|  | 0204 |
|  | 1202 |
| 1000 mg/m$^2$ | 0205 |
|  | 0106 |
|  | 0112 |

No patient terminated the study prematurely, i.e. all patients completed the study according to protocol.

A. Safety Evaluation

IMAB362 was found to be safe and well tolerated.

Only 25 AEs (adverse events), which occurred in 8 of the patients were rated as treatment-related. Treatment-related AEs were similar between the dose groups. More than half of these AEs were gastrointestinal disorders (mostly nausea, vomiting). Only one of these related AEs was rated as severe (vomiting), whereas all others were mild or moderate. All related AEs recovered, except for one case of dysgeusia (CTC grade 1 (mild)) with unknown outcome and a case of increased GGT (CTC grade 2 (moderate)) which did not recover.

No dose limiting toxicity (DLT), defined as a treatment-related AE that occurred during or within four weeks after the study drug infusion and was either grade 3 toxicity (except for nausea, vomiting, and alopecia) or grade 4 or 5 toxicity (according to CTC version 3.0), was observed in any of the dose groups. Accordingly, the maximum tolerated or applicable single dose (MTD) of IMAB362 determined in the present study is 1000 mg/m$^2$.

No related SAE and no suspected unexpected serious adverse reaction (SUSAR) occurred in the present study.

Only 7 patients had at least one laboratory value out of reference range assessed as grade 3 (severe). No dose-effect relationship and no clear relatedness to the study drug was observed. No laboratory values of CTC grade 4 (life-threatening) or 5 (death) were reported.

In conclusion, no relevant differences in AE profile and other safety parameters between the dose groups could be seen. Generally speaking, IMAB362 given in a single dose was observed to be safe and well-tolerated with nausea and vomiting being the most common related adverse event.

B. Evaluation of Pharmacokinetics and Immunogenicity

For determination of drug concentration the IMAB362 serum levels of all patients were measured immediately before the infusion of study medication, at the end of the infusion, at 3, 8, 12 and 24 hours after the end of the infusion and on days 3 (V3), 5 (V4), 8 (V5), 15 (V6) and 29 (V7).

An overview of the IMAB362 serum levels in the course of the study for each patient is given in Table 2. For unknown reasons for one patient (no. 1201) in the 300 mg/m$^2$ dose group a low IMAB362 serum level (12.633 µg/ml) was measured already before infusion of the study drug (V2, day 0).

TABLE 2

Time course of IMAB362 serum level [μg/ml] per patient

| Pat. no. | IMAB362 dose group | V2 0 h post infusion | V2 3 h post infusion | V2 8 h post infusion | V2 12 h post infusion | V2 24 h post infusion | V3 day 2 | V4 day 5 (±1) | V5 day 8 (±1) | V6 day 15 (±2) | V7 day 29 (±7) |
|---|---|---|---|---|---|---|---|---|---|---|---|
| 0103 | 33 mg/m² | 14.9 | 14.6 | 12.1 | 13.7 | 11.7 | 8.0 | 5.3 | 5.4 | 3.8 | 1.9 |
| 0104 | 33 mg/m² | 12.5 | 15.1 | 12.3 | 10.1 | 9.7 | 11.3 | 7.0 | 3.6 | 2.3 | 1.3 |
| 0201 | 33 mg/m² | 15.4 | 12.6 | 12.7 | 10.6 | 11.2 | 9.5 | 9.5 | 6.6 | 5.3 | 2.3 |
| 0105 | 100 mg/m² | 75.6 | 65.8 | 61.6 | 63.4 | 48.8 | 37.5 | 24.4 | 19.0 | 15.8 | 11.3 |
| 0202 | 100 mg/m² | 59.3 | 49.4 | 47.4 | 41.2 | 41.4 | 35.6 | 18.5 | 17.1 | 12.8 | 6.4 |
| 0203 | 100 mg/m² | 38.5 | 36.8 | 41.1 | 35.5 | 36.6 | 25.4 | 19.6 | 18.2 | 12.6 | 6.3 |
| 0403 | 300 mg/m² | — | 164.2 | 161.6 | 125.0 | 114.0 | 90.2 | 59.8 | 43.9 | 20.9 | 11.4 |
| 1101 | 300 mg/m² | 176.1 | 171.5 | 145.5 | 150.5 | 146.5 | 86.3 | 65.9 | 65.3 | 42.7 | 36.8 |
| 1201 | 300 mg/m² | 153.1 | 169.5 | 147.7 | 124.6 | 97.8 | 135.1 | 124.3 | 63.7 | 47.7 | 33.3 |
| 0204 | 600 mg/m² | 315.7 | 298.2 | 285.8 | 284.3 | 340.4 | 218.0 | 136.7 | — | 87.5 | 52.9 |
| 0302 | 600 mg/m² | 361.6 | 335.0 | 342.6 | 285.1 | 239.1 | 140.9 | 82.2 | 28.4 | 11.0 | 2.0 |
| 1202 | 600 mg/m² | 242.2 | 290.1 | 281.0 | 237.6 | 207.9 | 170.2 | 131.6 | 58.1 | 37.0 | 23.6 |
| 0106 | 1000 mg/m² | 493.7 | 606.1 | 488.9 | 465.9 | 452.7 | 367.8 | 259.9 | 158.8 | 79.3 | 34.7 |
| 0112 | 1000 mg/m² | 359.0 | 465.9 | 375.9 | 356.5 | 311.0 | 273.1 | 220.6 | 192.8 | 154.1 | 84.4 |
| 0205 | 1000 mg/m² | 479.7 | 435.9 | 366.7 | 331.6 | 343.9 | 279.7 | 193.9 | 155.3 | 105.9 | 38.9 |

* Peak concentration ($C_{max}$) of each patient is printed in bold

The mean observed peak concentrations ($C_{max}$) per dose group are shown in Table 3. Increasing mean values for $C_{max}$ correspond to the increasing infusion dosages of IMAB362.

TABLE 3

Peak concentrations ($C_{max}$) of IMAB362 during study - Summary of descriptive statistics

| | | $C_{max}$ [μg/mL] | | | | |
|---|---|---|---|---|---|---|
| IMAB362 dose group | N | Mean | SD | Min | Median | Max |
| 33 mg/m² | 3 | 15.1 | 0.3 | 14.9 | 15.1 | 15.4 |
| 100 mg/m² | 3 | 58.7 | 17.3 | 41.1 | 59.3 | 75.6 |
| 300 mg/m² | 3 | 169.9 | 5.9 | 164.2 | 169.5 | 176.1 |
| 600 mg/m² | 3 | 330.7 | 36.7 | 290.1 | 340.4 | 361.6 |
| 1000 mg/m² | 3 | 517.3 | 77.3 | 465.9 | 479.7 | 606.1 |

A graphical presentation of the mean blood concentrations of IMAB362 during the study is given in FIG. 1.

Highest IMAB362 levels were measured from directly at the end of infusion to up to 8 hours after end of infusion. At 3 hours after end of infusion the mean IMAB362 concentration was 14.1 μg/mL in the 33 mg/m² group, 50.7 μg/mL in the 100 mg/m² group, 164.2 μg/mL in the 300 mg/m² group, 307.8 μg/mL in the 600 mg/m² group, and 502.6 μg/mL in the 1000 mg/m² group.

Pharmacokinetics of IMAB362 is dose-dependent. Highest dose levels were observed within the first 8 hours after the 2 hours infusion. The mean half-life of IMAB362 was 8.5 days overall, ranging from about 5 to about 12 days in the different dose cohorts.

We determined from in vitro mode-of-action studies that at IMAB362 concentrations of 50 μg/ml robust execution of anti-tumor cell effects via ADCC, CDC and inhibition of proliferation can be expected and that $EC_{50}$ values of ADCC and CDC, which are considered as main mode of actions, are even covered with half of this concentration level. Based on this knowledge, 300 mg/m² and 600 mg/m² dose levels were identified for closer assessment in multiple dose studies with IMAB362. Patients who had received 300 mg/m² and 600 mg/m² IMAB362 were clearly above these levels at day 8 (V5) and close to 50 μg/m at day 15 (V3).

There was no evidence for anti-drug antibodies in patients after this single dose of IMAB362.

C. Evaluation of Antitumoral Activity

The primary measure for assessment of potential antitumoral activity was the tumor status according to RECIST (version 1.0) classification at 2 to 5 weeks after IMAB362 infusion (V3/V7). As all patients completed the study according to protocol, assessments were done exclusively at V7, i.e. 4 to 5 weeks after drug infusion. All patients were evaluated by CT.

Three patients had no measurable disease (patients 1101 and 1201 had no target lesion, for patient 0302 the respective data were unavailable) but were included into population for analysis of antitumoral activity, as this was not a formal efficacy evaluation.

Overall, for none of the patients a complete or partial response could be assessed. Stable disease was observed for one of the 15 patients in the 600 mg/m² dose group. While in the treated patients the percentage of tumor cells staining positive for CLDN18.2 ranged from 1% to 80% (up to 50% tumor cells with membranous staining), 90% or more of the tumor cells of this patient stained positive for CLDN18.2 with a large fraction of the tumor cells exhibiting membranous staining. Two patients in the 300 mg/m² group did also not progress and as they had no target lesion they were not evaluable for objective tumor response and were rated as non-CR, non-PD. The duration of the SD was about 2 months. The duration of non-CR, non-PD were about two months and 6 weeks, respectively.

An overview of the overall response by patient is given in Table 4.

TABLE 4

Tumor status (overall response) at V7 by patient

| IMAB362 dose cohort | Patient no. | Tumor status at V7 |
|---|---|---|
| 33 mg/m² | 0103 | Progressive disease |
| | 0104 | Progressive disease |
| | 0201 | Progressive disease |
| 100 mg/m² | 0105 | Progressive disease |
| | 0202 | Progressive disease |
| | 0203 | Progressive disease |
| 300 mg/m² | 0403 | Progressive disease |
| | 1101* | Non-CR, non-PD |
| | 1201* | Non-CR, non-PD |

TABLE 4-continued

Tumor status (overall response) at V7 by patient

| IMAB362 dose cohort | Patient no. | Tumor status at V7 |
|---|---|---|
| 600 mg/m² | 0204 | Stable disease |
| | 0302* | Progressive disease |
| | 1202 | Progressive disease |
| 1000 mg/m² | 0106 | Progressive disease |
| | 0112 | Progressive disease |
| | 0205 | Progressive disease |

*Patients without measurable disease (patients 1101 and 1201 had no target lesion, for patient 0302 the respective data were unavailable)

The different parameters contributing to the assessment of tumor status (overall response) are described in the following.

Regarding the change in sum of longest diameters (target lesion), status of non-target lesions after IMAB362 treatment, occurrence of new lesions, an overview of the evaluation results after IMAB362 treatment (assessed at V7) is provided in Table 5.

TABLE 5

Evaluation of parameters for assessment of tumor status at V7 by patient

| IMAB362 dose group | Patient no. | Percentage change in sum of longest diameter in target lesion | Unequivocal progression of a non-target lesion | New lesions |
|---|---|---|---|---|
| 33 mg/m² | 0103 | +30.2% | yes | no |
| | 0104 | +10.0% | yes | yes |
| | 0201 | +33.3% | yes | yes |
| 100 mg/m² | 0105 | +25.9% | no | yes |
| | 0202 | +35.9% | yes | yes |
| | 0203 | +35.1% | No non-target lesion | no |
| 300 mg/m² | 0403 | −37.8% | yes | yes |
| | 1101 | No target lesion | Unavailable data | no |
| | 1201 | No target lesion | no | no |
| 600 mg/m² | 0204 | +7.4% | no | no |
| | 0302 | Unavailable data | Unavailable data | yes |
| | 1202 | +66.7% | no | yes |
| 1000 mg/m² | 0106 | +36.5% | no | yes |
| | 0112 | +40.0% | no | no |
| | 0205 | −2.8% | No non-target lesion | yes |

The percentage change in sum of longest diameters of target lesion from V1 to V7 did not show any clear difference for different treatment doses.

For non-target lesions an unequivocal progression (from V1 to V7) was reported more frequently in patients in the lower dose levels but not in the 600 mg/m² and 1000 mg/m² dose levels.

In one patient in the 300 mg/m² group (0403) an unequivocal progression was observed in non-target lesion and a decrease in the longest diameter in one target lesion lymph node.

With regard to new lesions no preference for one of the dose groups was observed.

In case of patients 0302 (600 mg/m² dose group) and 0205 (1000 mg/m² dose group) the occurrence of new lesions was the reason for the assessment of overall response as progressive disease.

For assessment of the status of the non-target lesions according to RECIST, the level of the serum tumor antigens CA 125, CA 15-3, CA 19-9, and CEA was determined by the central laboratory at V2 (day 1, prior to infusion), V6 and V7.

An overview of the serum tumor markers for the 3 patients with an overall response of at least stable disease is given in Table 6.

TABLE 6

Serum tumor markers during the study of patients with overall response of at least stable disease

| Dose group | Patient ID | Tumor marker | Time point | Level | Out of reference range |
|---|---|---|---|---|---|
| 300 mg/m² | 1101 | CA 125 | V2 (prior inf.) | 21.2 U/mL | |
| | | | V6 | 20.6 U/mL | |
| | | | V7 | 27.7 U/mL | |
| | | CA 15-3 | V2 (prior inf.) | 21.3 U/mL | |
| | | | V6 | 21.0 U/mL | |
| | | | V7 | 21.3 U/mL | |
| | | CA 19-9 | V2 (prior inf.) | <0.6 U/mL | |
| | | | V6 | <0.6 U/mL | |
| | | | V7 | <0.6 U/mL | |
| | | CEA | V2 (prior inf.) | 1.7 ng/mL | |
| | | | V6 | 2.0 ng/mL | |
| | | | V7 | 2.1 ng/mL | |
| | 1201 | CA 125 | V2 (prior inf.) | 13.5 U/mL | |
| | | | V6 | 13.7 U/mL | |
| | | | V7 | 11.5 U/mL | |
| | | CA 15-3 | V2 (prior inf.) | 11.6 U/mL | |
| | | | V6 | 11.3 U/mL | |
| | | | V7 | 11.3 U/mL | |
| | | CA 19-9 | V2 (prior inf.) | 68.0 U/mL | yes |
| | | | V6 | 68.8 U/mL | yes |
| | | | V7 | 63.0 U/mL | yes |
| | | CEA | V2 (prior inf.) | 3.2 ng/mL | |
| | | | V6 | 2.6 ng/mL | |
| | | | V7 | 3.0 ng/mL | |
| 600 mg/m² | 0204 | CA 125 | V2 (prior inf.) | 59.2 U/mL | yes |
| | | | V6 | 50.2 U/mL | yes |
| | | | V7 | 35.1 U/mL | yes |
| | | CA 15-3 | V2 (prior inf.) | 477.5 U/mL | yes |
| | | | V6 | 372.3 U/mL | yes |
| | | | V7 | 310.4 U/mL | yes |
| | | CA 19-9 | V2 (prior inf.) | >10000 U/mL | yes |
| | | | V6 | 5667 U/mL | yes |
| | | | V7 | 3979 U/mL | yes |
| | | CEA | V2 (prior inf.) | 40.3 ng/mL | yes |
| | | | V6 | 25.2 ng/mL | yes |
| | | | V7 | 19.4 ng/mL | yes |

Of the 3 patients with stable disease or Non-CR/Non-PD according to imaging two patients had stable tumor marker levels in the observation period. One patient (0204) showed profound decrease of all 4 tumor markers after treatment. Most of the patients with progressive disease, in contrast, experienced an increase of tumor marker levels.

The tumor status (according to RECIST classification) at 4 to 5 weeks after IMAB362 infusion (V3/V7) was compared to baseline. Overall, for none of the patients a complete or partial response could be assessed. One of the 15 patients (in the 600 mg/m² dose group) showed stable disease at study end. Two patients in the 300 mg/m² dose group with non-measurable disease showed non-CR/non-PD. In line with this, tumor marker levels of these three patients either stayed stable (2 patients) or even decreased profoundly (1 patient). Most of the patients with progressive disease showed increase of tumor marker levels over time.

Regarding the parameters contributing to the assessment of tumor status (overall response), a decrease in one lesion was observed in the dose group 300 mg/m². At screening (V1), 13 of the 15 patients had a total of 32 non-target lesions. After IMAB362 treatment (assessed at V7) an unequivocal progression of a non-target lesion was reported for a total of 5 patients, 3 in the 33 mg/m² dose group, 1 in the 100 mg/m² group and 1 in the 300 mg/m² dose group. For none of these 5 patients the overall response was assessed as progressive disease only due to the progression of their non-target lesions. A total of 17 new lesions were observed in the course of the study, evenly distributed over the dose groups. In case of 2 patients (in the 600 mg/m² and 1000 mg/m² dose groups) the occurrence of new lesions was the reason for the assessment of overall response as progressive disease.

Moreover, ancillary data was collected in selected patients, showing that the patients serum components and the patients PBMCs are fully functional and potent in mediating the major IMAB362 modes of action CDC and ADCC, respectively.

In conclusion, hints for antitumoral activity (stable disease, tumor marker decrease) were observed in the 300 mg/m² and 600 mg/m² dose groups. Due to the small sample size of the dose groups, it is difficult to conclude on trends for efficacy.

C. Overall Conclusions

This trial was designed as first-in-human phase I, multicenter, non-randomized, inter-patient single-dose escalation, open-label clinical study with a single intravenous infusion of IMAB362 and a 4-week treatment-free follow-up period.

A total of 15 patients received study medication and were allocated to one of the dose cohorts (33, 100, 300, 600 or 1000 mg IMAB362/m²). The dose groups can be regarded as comparable. No relevant imbalances concerning the demographic data and baseline characteristics could be observed.

Regarding the primary objective of the study, no dose limiting toxicity (DLT) was observed in any of the dose groups. Therefore, the applicable single dose of IMAB362 in the present study was 1000 mg/m². IMAB362 was safe and well-tolerated with nausea and vomiting being the most common related adverse events.

The AE profile and the AE incidence was found to be similar in the different dose groups. No apparent differences between the dose groups could be observed in numbers of individual patients with clinically significant deteriorations in any hematological, biochemistry or coagulation parameters.

Regarding the potential antitumor activity of IMAB362 according to RECIST criteria, a complete or partial response could not be observed for any of the patients. One of the 15 patients (in the 600 mg/m² dose group) showed stable disease at study end. Two patients in the 300 mg/m² dose group with non-measurable disease showed non-CR/non-PD. Of these 3 patients with stable disease according to imaging two had stable tumor marker levels in the observation period. One patient showed profound decrease of all 4 tumor markers after treatment.

This and the pharmacokinetic studies, showing that targeted serum levels for IMAB362 are achieved at 600 mg/m² dose levels, support that this dose should be evaluated further.

Moreover, ancillary data confirms that the patients' immune effectors are fully functional and potent in mediating the major IMAB362 modes of action CDC and ADCC, respectively.

Example 2: Drug Potency

The aims of the in vitro analyses performed for this Phase I clinical study included an analysis if (i) effector cells present in patient blood are able to induce IMAB362-dependent ADCC, (ii) the complement system of the patient is able to induce IMAB362-dependent CDC and (iii) the ability of IMAB362 to induce ADCC and CDC is altered after administration in patients.

Different types of assays were performed to study the cytolytic activity induced by IMAB362 after administration in patients in detail. The assays were either performed with patient serum or patient PBMCs isolated from blood samples (Table 7). For comparison and to verify functionality of CDC and serum ADCC assays, a human serum pool (generated from healthy human subjects), in which fresh IMAB362 was serially diluted, was included in parallel in each assay. To test functionality of ADCC assays with PBMCs, blood cells isolated from a healthy donor were used as positive control in the same assay for each patient.

A. Materials and Methods

For the different in vitro assays patient serum samples were collected prior to infusion of IMAB362 and 1, 7, 14 and 28-32 days after IMAB362 antibody administration (Table 7). They were used as a source of IMAB362 antibody and complement in CDC or as antibody source in serum ADCC assays. Pre-infusion serum of patients was used as "no IMAB362" negative control and for dilution of patient serum samples to adjust the IMAB362 concentration to 0.5 µg/ml. Fresh blood samples were collected 14 days after infusion (7 days for patient 0203) and were used as a source of effector cells for ADCC assays.

TABLE 7

Overview of serum and blood samples collected for each patient.

| Subject No | IMAB362 dose [mg/m²] | Pre-infusion (y/n) | Serum obtained after infusion on day | | | Blood obtained on day |
|---|---|---|---|---|---|---|
| 0201 | 33 | y | 1 | 7 | 14 30 | 14 |
| 0202 | 100 | y | 1 | 7 | 14 28 | 14 |
| 0203 | 100 | y | 1 | 7 | 14 28 | 14 |
| 0403 | 300 | y | 1 | 7 | 14 28 | 7 |
| 0204 | 600 | y | 1 | n.o. | 14 32 | 14 |
| 0205 | 1000 | y | 1 | 7 | 14 30 | 14 | n.o.: serum sample was not obtained from clinical study site

Blood samples were collected from patients (Table 7), serum was harvested and serum aliquots were prepared and immediately stored at −80° C. Analysis of all these samples was performed in one single experiment after collection of all 24 serum samples.

For ADCC, fresh blood samples (15 ml Na₂EDTA) were used to isolate PBMCs and ADCC assays were performed the next day.

The capability of patients' PBMCs to induce ADCC in conjunction with IMAB362 was tested ex vivo by using fresh 15 ml Na₂-EDTA anti-coagulated blood samples obtained from the patients 14 days (7 days for patient 0203) after IMAB362 administration. PBMCs of blood samples were isolated upon arrival using Ficoll density gradient centrifugation. PBMCs were cultivated for 24 h and ADCC assays were performed the next day with luciferase-transfected CLDN18.2-positive NUGC4 human gastric cancer cells as targets in conjunction with various concentrations of exogenously added IMAB362. PBMCs were added in an E:T ratio of 20:1 and assays were incubated for 24 h at 37° C., 5% CO₂ PBMCs obtained from a healthy donor were tested in the same setting in parallel to analyze validity of the assay (positive assay control). This PBMC stock was stored in liquid N₂ and for each ADCC assay with patients' PBMCs, an aliquot from this PBMC stock was thawed and analyzed in parallel.

Characterized materials used were:

CLDN18.2 positive target cells: transiently luciferase-transfected NUGC4-10cH11E10 stomach cancer cells Positive control effector cells: PBMCs obtained from a healthy donor (frozen $N_2$-stock lot ID: 276-SMS-09-00706, 4e7c/vial, MNZ, 08.07.07.SJA)

Functional control antibody: IMAB362 in serial dilutions (0.4 ng/ml-126.5 µg/ml)

Assay negative control antibody: Istotype control (Rituximab, 126.5 µg/ml)

The ability of patient serum components to induce complement-dependent cytotoxicity (CDC) in conjunction with IMAB362 was analyzed ex vivo over time. Serum samples were collected and stored at −80° C. and all patient samples were assayed in parallel in the same experiment. In addition to pre-infusion serum to which a fixed amount of 0.5 µg/ml IMAB362 (representing the in vitro $EC_{50}$ concentration) was added exogenously, also samples collected 1, 7, 14 and 28-32 days after IMAB362 administration were tested, in which circulating IMAB362 had to be adjusted to 0.5 µg/ml (CDC with normalization). The final serum concentration in each assay was adjusted to 20%. Luciferase-transfected CHO-K1 cells stably transfected with CLDN18.2 were used as targets. For comparison a serum pool of healthy human donors spiked with IMAB362 was tested.

Characterized Materials Used were:

CLDN18.2 positive target cells: Stably transfected CHO-K1 p740 luci #2A5 cells.

Assay positive control: IMAB362 serial dilutions (1:3.16) prepared in human serum pool from healthy donors, resulting in final concentrations ranging from 31.6 ng/ml to 10.0 µg/ml.

Functional control antibody: IMAB362 adjusted to 0.5 µg/ml final assay concentration in each patient pre-infusion serum sample.

Assay negative control antibody: Isotype control antibody diluted in human serum pool (Rituximab).

The kinetics of the overall cytotoxicity mediated by IMAB362 in human circulation, integrating its capability to induce ADCC and CDC, was analyzed in an "one tube" assay.

Serum of each patient collected 7, 14 and 28-32 days after i.v. administration of IMAB362, and thus comprising complement factors of the patient plus circulating IMAB362, was tested in this assay. Serum was applied in each assay to a final serum concentration of 25% (v/v). PBMCs of a healthy control were added as effector cells, whereas NUGC-4 cells served as target cells with an E:T ratio of 40:1.

In an additional setting, the serum was heat-inactivated destroying the complement activity. This second assay thus exclusively reflects ADCC activity induced by IMAB362 present in the patient serum.

During the Phase I study, serum samples were collected and stored at −80° C. All patient samples were assayed in parallel in the same experiment.

Characterized Materials Used were:

CLDN18.2 positive target cells: Stably luciferase-transfected NUGC-4 10CH11 luci eGFP #2 stomach cancer cells.

Effector cells: PBMCs from a healthy donor (fresh buffy coat).

Functional control antibody: IMAB362 serial dilutions (0.26 ng/ml-200.0 µg/ml) spiked in human serum pool.

Sample positive control: Patient pre-infusion serum sample spiked with IMAB362 (200.0 µg/ml) (representing $EC_{80-100}$ for IMAB362 in this setting).

Assay negative control antibody: Isotype control antibody in human serum pool (Rituximab).

The ability of IMAB362 to interact and activate complement present in the patient serum and to induce complement-dependent cytotoxicity (CDC) after prolonged circulation in patient blood was analyzed ex vivo 1, 7, 14 and 28-32 days after IMAB362 administration. The assay was performed by directly using the patient serum samples in the assay (CDC without normalization). As a positive control pre-infusion serum to which a fixed amount of 10 µg/ml IMAB362 (representing the in vitro $EC_{90-100}$ concentration) was added exogenously. The final serum concentration in each assay was adjusted to 20%. Luciferase-transfected CHO-K1 cells stably transfected with CLDN18.2 were used as targets. For comparison a serum pool of healthy human donors spiked with IMAB362 was tested. During the Phase I study serum samples were collected and stored at −80° C. All patient samples were assayed in parallel in the same experiment.

Characterized Materials Used were:

CLDN18.2 positive target cells: Stably transfected CHO-K1 p740 luci #2A5 cells.

Functional control antibody: IMAB362 serial dilutions (1:3.16) prepared in human serum pool from healthy donors, resulting in final concentrations ranging from 31.6 ng/ml to 10.0 µg/ml.

Sample positive control: Pre-infusion patient serum samples each spiked with IMAB362 (10.0 µg/ml) in (in vitro CDC-$EC_{90-100}$ concentration).

Assay negative control antibody: Isotype control antibody diluted in human serum pool.

B. Results

Capability of Patients' PBMCs to Mediate ADCC

In order to analyze the capability of patient immune cells to lyse CLDN18.2 expressing tumor cells, NUGC-4-gastric cancer cells, endogenously expressing CLDN18.2, were incubated with increasing concentrations of IMAB362 and with patient PBMCs. Assays with PBMCs from a healthy donor were included as functional control.

Patient PBMCs showed IMAB362-dose dependent lysis rates with a maximum of 27 to 77% at a concentration of ~30 µg/ml. This is not significantly different (unpaired t-test) from the maximal lysis rates of 14 to 56% obtained with healthy control PBMCs tested in the same assays (FIG. 2). ADCC activity was most profound for patient 0204.

These data show, that PBMCs of gastric cancer patients are not inferior in inducing ADCC of human CLDN18.2 positive gastric cancer cells in conjunction with IMAB362 as compared to PBMCs obtained from healthy donors.

Capability of the Patients' Complement System to Induce CDC

The ability of patient complement to interact with IMAB362 present in the serum and to induce CDC was tested. The pre-infusion serum samples were spiked with fresh 0.5 µg/ml IMAB362 and CDC activity was compared to the same antibody concentration spiked in human serum pool. Serum/antibody samples were incubated with CHO-K1 p740 luci #2A5 cells and lysis was determined after 80 min by measuring luciferase activity.

Figure 4A:
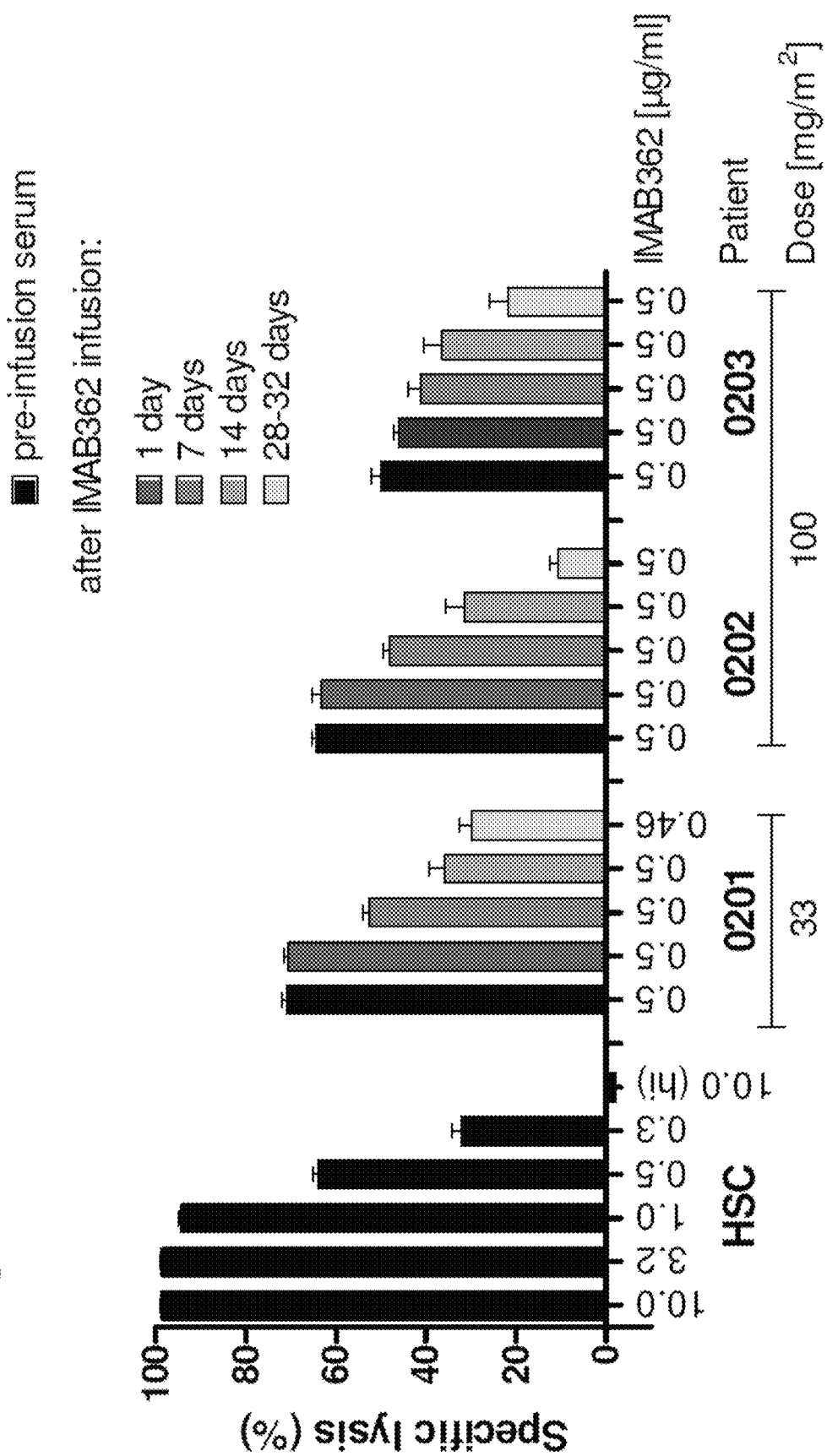
Figure 4B:
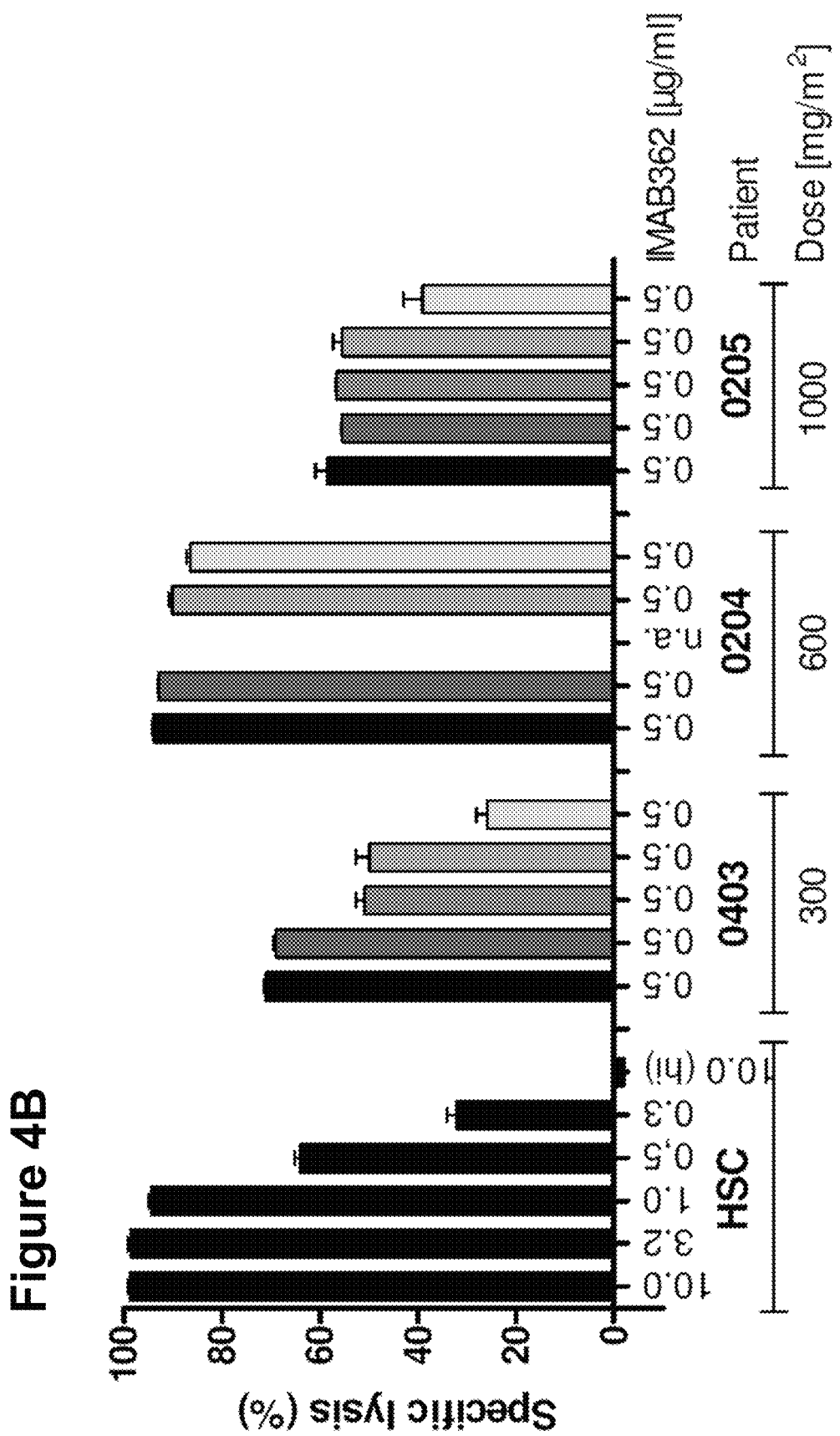

All patients were capable to induce significant CDC within 80 min (FIG. 3). For 5 out of 6 patients maximum lysis rates ranging from 50 to 71% were observed. This is comparable to data we obtained by parallel testing with pooled sera from healthy controls (64.5%). Noteworthy, patient 0204 showed highest CDC activity with fresh IMAB362 (93.9%).

loss in CDC activity after 28-32 days is significant and most pronounced in patients treated with low doses of IMAB362 (FIG. 4). In patients treated with high doses (0204; 600 mg/m$^2$ and 0205; 1000 mg/m$^2$) CDC activity appeared to be better conserved over the time period investigated. Based on currently available data, the underlying mechanism for this decline is not understood so far.

TABLE 8

IMAB362 concentrations in patient serum at different time points used in the different ADCC and CDC assays.

| Subject No. | IMAB362 treatment (mg/m$^3$) | Time after IMAB362 treatment (days) | IMAB362 concentration in undiluted patient serum[1] [µg/ml] | Dilution factor for obtaining 0.5 µg/ml IMAB362 in CDC assays (fold) | IMAB362 concentration in cytotoxicity assays [µg/ml] | IMAB362 concentration in non-normalized CDC assays [µg/ml] |
|---|---|---|---|---|---|---|
| 0201 | 33 | 1 | 11.17 | 22.34 | 2.79 | 2.2 |
|  |  | 7 | 6.63 | 13.27 | 1.66 | 1.4 |
|  |  | 14 | 5.30 | 10.60 | 1.32 | 1.1 |
|  |  | 30 | 2.31 | 4.62 | 0.58 | 0.5 |
| 0202 | 100 | 1 | 41.37 | 82.74 | 10.34 | 8.3 |
|  |  | 7 | 17.08 | 34.15 | 4.27 | 3.4 |
|  |  | 14 | 12.78 | 25.56 | 3.16 | 2.6 |
|  |  | 28 | 6.41 | 12.82 | 1.60 | 1.3 |
| 0203 | 100 | 1 | 36.58 | 73.17 | 9.15 | 7.3 |
|  |  | 7 | 18.24 | 36.48 | 4.56 | 3.6 |
|  |  | 14 | 12.63 | 25.26 | 3.16 | 2.5 |
|  |  | 28 | 6.34 | 12.69 | 1.59 | 1.3 |
| 0403 | 300 | 1 | 113.40 | 227.91 | 28.49 | 22.8 |
|  |  | 7 | 43.91 | 87.81 | 10.98 | 8.7 |
|  |  | 14 | 20.97 | 41.95 | 5.24 | 4.2 |
|  |  | 28 | 11.41 | 22.81 | 2.85 | 2.3 |
| 0204 | 600 | 1 | 340.38 | 680.76 | 85.10 | 68.1 |
|  |  | 7 | n.a. | n.a. | n.a. | n.a. |
|  |  | 14 | 87.53 | 175.06 | 21.88 | 17.5 |
|  |  | 32 | 52.86 | 105.72 | 13.22 | 10.6 |
| 0205 | 1000 | 1 | 343.93 | 687.86 | 85.60 | 68.8 |
|  |  | 7 | 155.28 | 310.56 | 38.82 | 31.1 |
|  |  | 14 | 105.91 | 211.81 | 26.48 | 21.2 |
|  |  | 30 | 38.92 | 77.84 | 9.73 | 7.8 | n.a. not available;
n.d.: excluded, not determined;
[1]concentration measured by vivoScience via ELISA Capability of Soluble Effectors in the Patient Serum to Induce Cell Killing with Intravenously Circulating IMAB362

Next, the ability of patients' serum to interact with i.v. administered IMAB362 over the time span of its circulation in the patient was investigated by testing serum samples collected at different time points after IMAB362 administration in CDC assays on CLDN18.2 positive CHO-K1 target cells. Serum samples were the source for patient-specific soluble effectors including complement as well as for IMAB362. IMAB362 concentrations in serum samples were determined by ELISA (vivoScience) (Table 8) and adjusted to a final IMAB362 concentration of 0.5 µg/ml (median EC50 of IMAB362) using the corresponding pre-infusion serum of each patient as diluents. As IMAB362 concentrations differ depending on treatment dose and time point of blood collection, the dilution factor for the samples differed considerably between patients ranging from 4.6fold to 688fold. A serum pool from healthy donors (HSC) was used as a control (FIG. 4).

As compared to the positive control (pre-infusion serum of the respective patient+fresh IMAB362) killing activity is retained within the first 24 h, whereas cytolytic activity of serum samples collected one week later is decreased, which is progressing further in the following weeks (FIG. 4). Even so, considerable cytotoxicity was executed by patients serum even 2 weeks after administration of IMAB362. The Effect of Serum Components on IMAB362 Induced Cytotoxicity ADCC activity of mABs may be impaired in the presence of human serum. The effect of the patients sera on ADCC activity was investigated. To this aim, serum of each patient collected 7, 14 and 28-32 days after IMAB362 administration and thus representing complement factors of the patient plus circulating i.v. administered IMAB362 was used. All patient serum samples were diluted to 25% (v/v) final serum concentration and the remaining IMAB362 concentration in each patient assay sample was calculated (Table 8). PBMCs from one healthy donor were used as effectors and NUGC-4 cells as target cells (E:T ratio=40:1) in this ADCC assay. All assays for all patients were performed in parallel in one single experiment using the same conditions, target cells and donor PBMCs to ensure comparability. As functional assay control the healthy human serum pool was spiked with IMAB362 (200.0 µg/ml). As additional positive control the individual patient pre-infusion serum samples were spiked with 200.0 µg/ml IMAB362 (representing in vitro $EC_{80\text{-}100}$ for IMAB362 in this system).

We observed in all assays that IMAB362 antibodies present in patient serum after administration are highly active and induce cytotoxicity (FIG. 5). Biological activity of IMAB362 was retained over 28-32 days after administration with specific killing still being above 48% in all dose groups. Overall differences between dose groups were surprisingly modest, suggesting a saturation effect. In patients treated with lower doses (33-300 mg/m$^2$) a moderate decrease in specific killing from 77.7-87.4% down to 48.3-66.8% was observed over time correlating with the decrease in the antibody concentrations in the serum (FIG. 5 upper panel). Highest activity stably maintained over time was observed in patients treated with 600 or 1000 mg/m$^2$ IMAB362 (FIG. 5 lower panel).

Figure 6A:
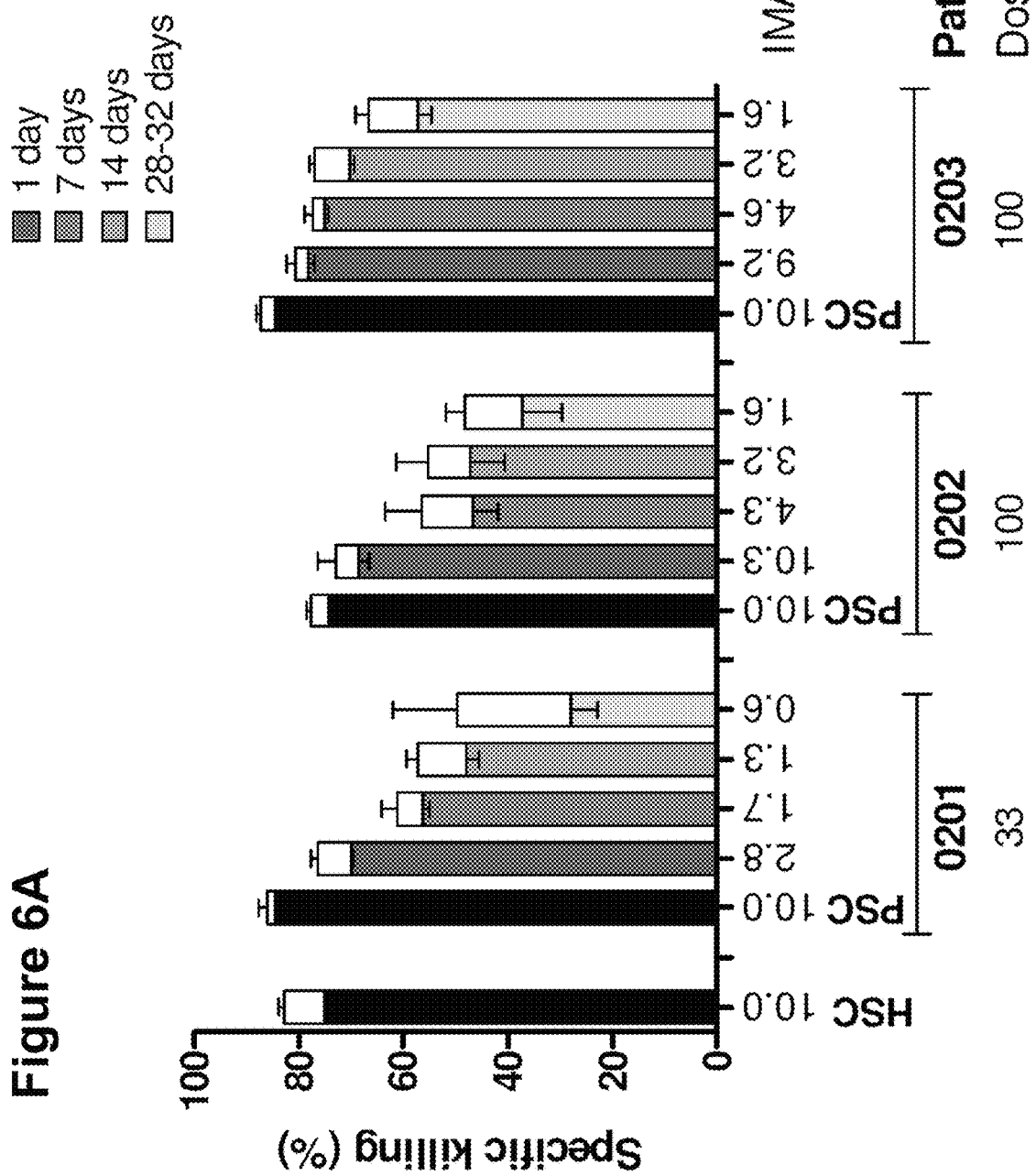
FIGS. 6A and 6B show kinetics of ADCC activity of IMAB362 in heat-inactivated patient serum. The assay was performed as described in the previous figure, except here patient complement was heat-inactivated (56° C., 30 min) to single out ADCC activity (black and grey bar parts) and to calculate additive effects of serum components (white bar parts).
Figure 6B:
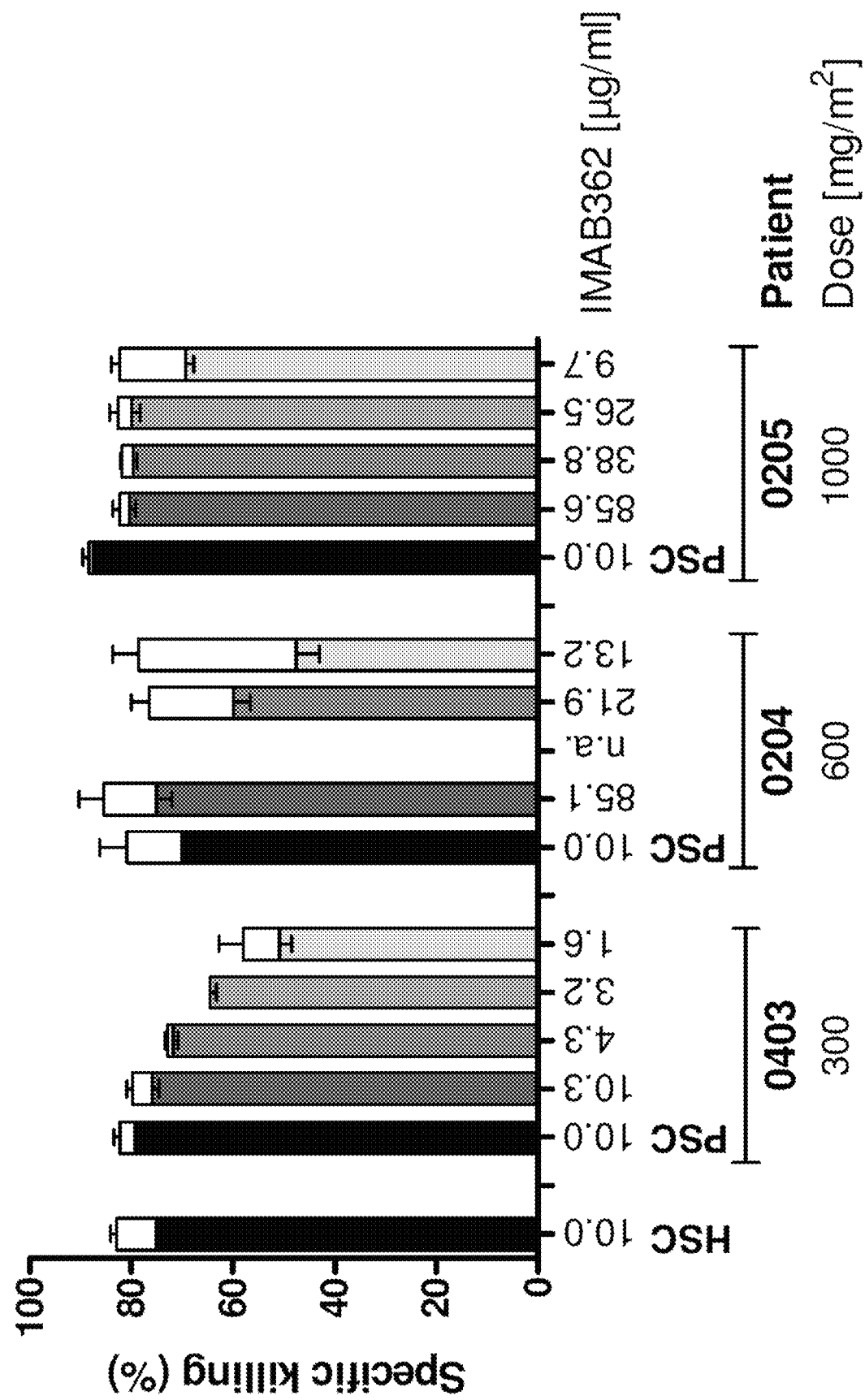

This assay was repeated with serum samples, in which complement factors were inactivated by incubating them at 56° C. for 30 min. Cytotoxicity with heat-inactivated patient serum samples was lower as compared to those obtained with untreated serum samples in all cases. Similar decreases were also observed with the heat-inactivated pool from healthy donors (HSC, FIG. 6).

In summary, these data indicate that patient serum does not inhibit ADCC capability of soluble serum components but instead add to IMAB362 induced total cytolytic activity.

Kinetics of IMAB362 Mediated CDC in Patient Serum

In order to determine the kinetics of CDC capability of IMAB362 in serum from patients of the different dose groups serum samples were collected 1, 7, 14 and 28 days after IMAB362 administration.

Again, this serum served as source for complement as well as for IMAB362. Final serum concentrations were adjusted to 20% (v/v) final volume. The final IMAB362 concentrations in each CDC assay sample are listed in Table 7. As positive control, patient pre-infusion samples were spiked with fresh IMAB362 antibody to a final concentration of 10 µg/ml (in vitro EC$_{95}$ of IMAB362 in this CDC assay system). Furthermore, for functional control of the CDC assay, serial dilutions of IMAB362 (0.032-10 µg/ml) were prepared in human serum pool. A standardized assay with CHO-K1 cells stably transfected with CLDN18.2 and luciferase were used as target cells. All serum samples were thawed and tested in parallel in the same experiment.

Figure 7B:
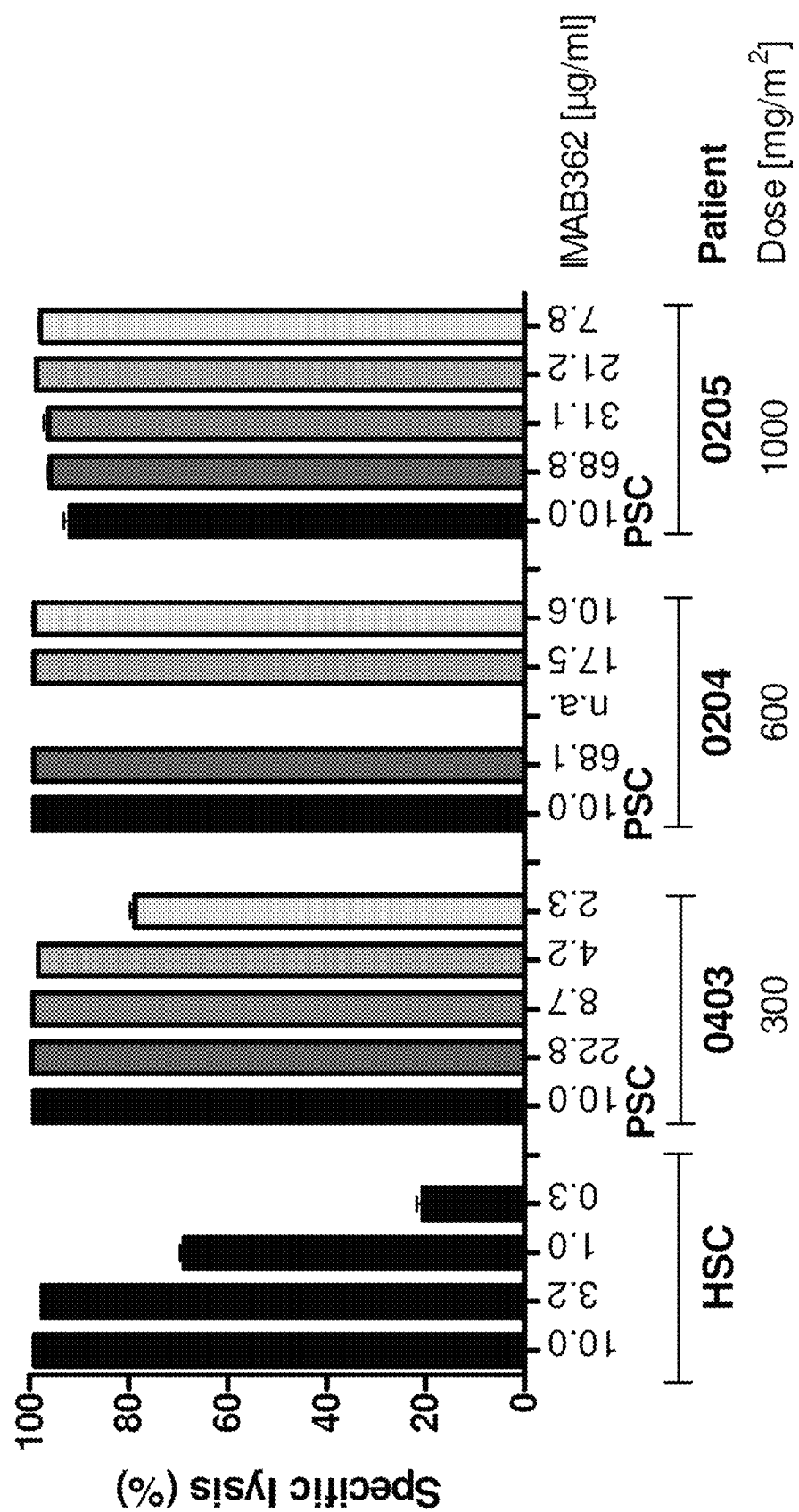

CDC activity correlates well with the antibody concentration in each serum sample (FIG. 7). Most importantly, the data suggests that CDC-mediated cytotoxic activity is maintained over 4 weeks. In particular, patients of high dose groups show no drop of CDC activity over this time.

Summary and Conclusions

Patients with GEC appear not to be impaired in their capability to induce both ADCC and CDC of CLDN18.2 expressing target cells in conjunction with IMAB362. Noteworthy, max. specific lysis seen in ADCC and CDC and EC$_{50}$ measured for ADCC were highest for patient 0204, who had the most prominent clinical and serum tumor antigen response.

Ex vivo analysis of CDC with circulating IMAB362 at different time points after its administration showed that still 2 weeks after administration there is sufficient active IMAB362 circulating in the patients to induce profound ADCC and CDC.

CDC activity of patients in conjunction with circulating IMAB362 is reduced over time for so far unknown reasons.

Example 3: Cytokines

Cytokine serum levels may serve as indicators of the immune status of a patient. In this clinical trial the objective of analyzing cytokines was primarily for supporting safety monitoring. We reviewed cytokines within this ancillary analysis from the viewpoint of defining potential biomarker candidates.

Cytokine levels were determined on day 1 prior to IMAB362 infusion and on days 3 and 5 of the treatment cycle. Studied cytokines comprised proinflammatory (IL-1, IL-6, IL-12, IFNγ, TNFα) and anti-inflammatory (IL-4, IL-10) cytokines and cytokines necessary for growth and function of T cells (IL-2) and NK cell proliferation (IL-2, IL-15).

Cytokines were analyzed by ELISA and flow cytometry (Interlab). Cytokines were analyzed according to Interlab SOP-MU-IMM.M.0144. 05 "Flow Cytomix Cytokin-Check IL4, IL6, IL13, TNF-alpha, IFN-gamma, MCP-1, IL10 IL2, IL1-β, IL12p70, IL8, IL17A, IL23" and SOP-MU-IMM.M.0151.02 "Humanes Interleukin 15".

Cytokine serum levels of IL-1, IL-2, IL-4, IL-6, IL-10, IL-12, IL-15, IFNγ, and TNFα were analyzed for 14 out of 15 patients (Table 9). No cytokine levels were determined for patient 0403 (300 mg/m$^2$). Only serum cytokine level values, which were above reference range, were analyzed for temporal changes. Reference range values were defined by Interlab (see CSR GM-IMAB-001).

TABLE 9

Cytokine serum levels on Day 1, Day 3 and Day 5
Cytokine serum levels of all patients were measured on Day 1, Day 3 and Day 5. The reference range for each cytokine is indicated. Values below or above the detection limit were set to the respective detection limit for calculations.

| (Reference range [pg/mL]) | Day | Patient |||||||||||||| 
|---|---|---|---|---|---|---|---|---|---|---|---|---|---|---|---|
| | | 0103 | 0104 | 0201 | 0105 | 0202 | 0203 | 1101 | 1201 | 0204 | 0302 | 1202 | 0106 | 0112 | 0205 |
| | | \multicolumn{14}{c}{Dose [mg/m$^2$]} |
| | | 33 ||| 100 ||| 300 ||| 600 ||| 1000 |||
| | | \multicolumn{14}{c}{Proinflammatory cytokines [pg/mL]:} |
| IL-1 | 1 | <4.2 | <4.2 | <4.2 | <4.2 | <4.2 | 11.7 | <4.2 | <4.2 | <4.2 | <4.2 | <4.2 | <4.2 | <4.2 | <4.2 |
| (<5.2) | 3 | <4.2 | <4.2 | <4.2 | <4.2 | <4.2 | <4.2 | <4.2 | <4.2 | <4.2 | <4.2 | <4.2 | <4.2 | <4.2 | <4.2 |
| | 5 | <4.2 | <4.2 | <4.2 | <4.2 | <4.2 | <4.2 | <4.2 | <4.2 | <4.2 | <4.2 | <4.2 | <4.2 | <4.2 | <4.2 |
| IL-6 | 1 | <1.2 | <1.2 | <1.2 | 10.7 | <1.2 | 8.3 | <1.2 | 2.6 | 6.4 | 4.2 | 2.8 | <1.2 | 16 | 4.2 |
| (<4.5) | 3 | <1.2 | 25.7 | <1.2 | 5.2 | <1.2 | 5.9 | <1.2 | 2.6 | 123 | 4.2 | 12.5 | <1.2 | <1.2 | 2.8 |
| | 5 | <1.2 | 11.6 | <1.2 | 5.2 | <1.2 | 7.5 | 5.3 | <1.2 | 27.9 | 4.2 | 23.4 | <1.2 | <1.2 | 5.6 |
| IL-12 | 1 | <1.5 | <1.5 | 3.9 | <1.5 | <1.5 | <1.5 | <1.5 | <1.5 | <1.5 | <1.5 | <1.5 | <1.5 | <1.5 | <1.5 |
| (<11.6) | 3 | <1.5 | <1.5 | 3.9 | <1.5 | <1.5 | <1.5 | <1.5 | <1.5 | <1.5 | <1.5 | <1.5 | <1.5 | <1.5 | <1.5 |
| | 5 | <1.5 | <1.5 | <1.5 | <1.5 | <1.5 | <1.5 | <1.5 | <1.5 | <1.5 | <1.5 | <1.5 | <1.5 | <1.5 | <1.5 |
| IFNγ | 1 | <1.6 | <1.6 | 182 | <1.6 | <1.6 | 26.2 | 30.7 | <1.6 | <1.6 | <1.6 | 81.2 | <1.6 | <1.6 | 35.9 |
| (<45.0) | 3 | <1.6 | <1.6 | 173 | <1.6 | <1.6 | <1.6 | <1.6 | <1.6 | <1.6 | <1.6 | <1.6 | <1.6 | <1.6 | <1.6 |
| | 5 | <1.6 | <1.6 | 71.8 | <1.6 | <1.6 | <1.6 | 3.5 | <1.6 | <1.6 | <1.6 | <1.6 | <1.6 | <1.6 | <1.6 |

TABLE 9-continued

Cytokine serum levels on Day 1, Day 3 and Day 5
Cytokine serum levels of all patients were measured on Day 1, Day 3 and Day 5. The reference range for each cytokine is indicated. Values below or above the detection limit were set to the respective detection limit for calculations.

| (Reference range [pg/mL]) | Day | Patient 0103 | 0104 | 0201 | 0105 | 0202 | 0203 | 1101 | 1201 | 0204 | 0302 | 1202 | 0106 | 0112 | 0205 |
|---|---|---|---|---|---|---|---|---|---|---|---|---|---|---|---|
| | | 33 | | | 100 | | | 300 | | 600 | | | 1000 | | |
| | | Dose [mg/m$^2$] | | | | | | | | | | | | | |
| TNFα (<17.5) | 1 | <3.2 | <3.2 | 29.8 | <3.2 | <3.2 | 10.1 | <3.2 | <3.2 | <3.2 | <3.2 | <3.2 | <3.2 | <3.2 | <3.2 |
| | 3 | <3.2 | <3.2 | 15.7 | <3.2 | <3.2 | 4.6 | <3.2 | <3.2 | <3.2 | <3.2 | <3.2 | <3.2 | <3.2 | <3.2 |
| | 5 | <3.2 | <3.2 | 10.1 | <3.2 | <3.2 | <3.2 | <3.2 | <3.2 | <3.2 | <3.2 | <3.2 | <3.2 | <3.2 | <3.2 |
| Anti-inflammatory cytokines [pg/mL]: | | | | | | | | | | | | | | | |
| IL-4 (20.8) | 1 | <20.8 | <20.8 | 57.1 | <20.8 | 28.1 | <20.8 | <20.8 | <20.8 | <20.8 | <20.8 | <20.8 | <20.8 | <20.8 | <20.8 |
| | 3 | <20.8 | <20.8 | <20.8 | <20.8 | 21.2 | <20.8 | <20.8 | <20.8 | <20.8 | <20.8 | <20.8 | <20.8 | <20.8 | <20.8 |
| | 5 | <20.8 | <20.8 | <20.8 | <20.8 | 28.1 | <20.8 | <20.8 | <20.8 | <20.8 | <20.8 | <20.8 | <20.8 | <20.8 | <20.8 |
| IL-10 (<6.0) | 1 | 20.7 | 27.3 | 38.1 | <6.0 | 20.7 | 14.1 | 9.0 | <6.0 | <6.0 | <6.0 | <6.0 | <6.0 | <6.0 | <6.0 |
| | 3 | 19.4 | 23.3 | 28.6 | <6.0 | 22.0 | <6.0 | <6.0 | <6.0 | <6.0 | <6.0 | <6.0 | <6.0 | <6.0 | <6.0 |
| | 5 | 20.7 | 27.3 | 23.3 | <6.0 | 22.0 | <6.0 | 13.6 | <6.0 | <6.0 | <6.0 | <6.0 | <6.0 | <6.0 | <6.0 |
| Cytokines for T-cell and NK cell function and proliferation [pg/mL]: | | | | | | | | | | | | | | | |
| IL-2 (<20.0) | 1 | <16.4 | <16.4 | 354 | <16.4 | 55.3 | 45.4 | <16.4 | <16.4 | <16.4 | <16.4 | 42.8 | <16.4 | <16.4 | 42.8 |
| | 3 | 17.3 | <16.4 | 259 | <16.4 | <16.4 | <16.4 | <16.4 | <16.4 | <16.4 | <16.4 | <16.4 | <16.4 | <16.4 | <16.4 |
| | 5 | <16.4 | <16.4 | 162 | <16.4 | <16.4 | <16.4 | 71.4 | <16.4 | <16.4 | <16.4 | <16.4 | <16.4 | <16.4 | <16.4 |
| IL-15 (<3.0) | 1 | <3.0 | 698 | <3.0 | <3.0 | 51 | <3.0 | <3.0 | 18.3 | <3.0 | <3.0 | 23.1 | <3.0 | <3.0 | <3.0 |
| | 3 | <3.0 | 646 | <3.0 | <3.0 | 43 | <3.0 | <3.0 | 18.3 | <3.0 | <3.0 | 14.7 | <3.0 | <3.0 | <3.0 |
| | 5 | <3.0 | 582 | <3.0 | <3.0 | 47.7 | <3.0 | <3.0 | 11.7 | 6.0 | <3.0 | 10 | <3.0 | <3.0 | <3.0 |

Proinflammatory cytokine levels (IL-1, IL-6, IL-12, IFNγ, TNFα) were above the respective reference ranges in 9 out of 14 patients (0104, 0105, 0201, 0203, 0204, 0112, 1202, 0112, 0205). IFNγ levels were elevated in two patients (0201, 1202), TNFα level was elevated in one of these two patients (0201). In both patients IFNγ and TNFα levels were elevated before administration of IMAB362 and decreased on the following days. IL-6 levels were elevated in eight patients (0104, 0105, 0203, 1101, 0204, 0112, 1202, 0205). No clear pattern in IL-6 level changes with respect to IMAB362 administration and dose-effect relationship becomes evident. IL-6 levels of patient 0204 (600 mg/m$^2$ IMAB362) were not elevated prior to administration but increased considerably 2 days after infusion, a pattern not displayed by any other patient. IL-1 and IL-12 levels stayed within the respective reference range for all patients.

Anti-inflammatory cytokine levels (IL-4, IL-10) were above the respective reference range in 6 out of 14 patients (0103, 0104, 0201, 0202, 0203, 1101). IL-10 levels were elevated in six patients (0103, 0104, 0201, 0202, 0203, 1101), IL-4 levels were elevated in two of these patients (0201, 0202). Fluctuations of anti-inflammatory cytokine levels show no clear pattern with respect to administration of IMAB362 and dose-effect relationship.

The cytokines for T-cell and NK cell function and proliferation IL-2 and IL-15 levels were above the respective reference range in 9 out of 14 patients (0104, 0201, 0202, 0203, 1101, 1201, 0204, 1202, 0205). IL-2 levels were above reference range in six patients (0201, 0202, 0203, 1101, 1202, 0205), IL-15 levels were above reference range in five patients (0104, 0202, 1201, 0204, 1202). Seven out of nine patients (0104, 0201, 0202, 0203, 1201, 1202, 0205) with elevated IL-2/IL-15 levels pre-administration displayed a cytokine level decrease on subsequent days: IL-2/IL-15 levels were above respective reference range prior to IMAB362 administration and decreased on the second and fourth day after IMAB362 administration. The most pronounced decrease in this group was observed for the IL-2 serum concentrations. In all five patients (0201, 0202, 0203, 1202, 0205) with increased IL-2 pre-infusion levels a decrease to less than 50% of respective pre-infusion levels was observed on the fourth day after administration. This decrease could be observed also in one patient (0201) with a considerably elevated IL-2 level (354 pg/mL) before administration of 33 mg/m$^2$ IMAB362.

A different IL-2 concentration profile was shown by patient 1101 (300 mg/m$^2$ IMAB362) with IL-2 levels in reference range before infusion and 2 days later but elevated IL-2 concentration on the fourth day after infusion.

The IL-15 level was decreased on the fourth day after administration in all four patients (0104, 0202, 1201, 1202) with elevated IL-15 pre-infusion levels. This concentration profile is very similar to the observed IL-2 concentration profile although the relative level decrease is not as pronounced.

No dose-effect relationship can be discerned for any of the analyzed cytokines.

Summarizing the above, analysis of pre-treatment levels of patients showed that IL-6, IL-10, IL-2, IL-15 are elevated in a substantial fraction of late stage patients with gastroesophageal disease. In contrast, none or only single patients had elevated levels of IL-1, IL-12, IL-4, IFNγ, and TNFα.

Analysis of alteration of cytokine levels within the first 5 days after IMAB362 treatment led to following observations. In all five patients with elevated IL-2 levels, these levels were found to decline profoundly, with four of five patients reaching normal reference values. Similarly, in all four patients with elevated IL-15 levels a moderate decrease after IMAB362 administration was observed. Decrease of elevated levels after treatment were also seen for single patients with elevated levels of IFNγ and TNFα, respectively. IL-6, in contrast, increased after IMAB362 administration, with four patients pre-treatment and 7 of 14 patients on day 5 post-treatment showing IL-6 above reference levels.

Example 4: International, Multicenter, Open-Label, Phase IIa, Multiple Dose Study Evaluating the Efficacy and Safety of Multiple Doses of IMAB362 in Patients with Advanced Adenocarcinoma of the Stomach or the Lower Esophagus An international, multicenter, open-label, phase IIa, multiple dose study was performed to investigate the efficacy and safety of multiple doses of IMAB362 in patients with advanced adenocarcinoma of the stomach or the lower esophagus. The primary objective of this study was to study the rate of remission (CR, PR) according to RECIST. The secondary objectives of this study were: frequency and severity of adverse events according to CTCAE v3.0 and tolerability of multiple doses of IMAB362, progression-free survival time (PFS): The time from start of the first infusion to date of first observed disease progression or death due to any cause (whichever occurs first), immunogenicity by analysis of human anti-chimeric antibodies, quality of life, clinical benefit (CR, PR and SD according to RECIST), and pharmacokinetics of IMAB362 by serum levels.

Patients underwent screening for determination of presence of the IMAB362 target CLDN18.2 in their tumor. CLDN18.2 status was determined by immunohistochemistry with an anti-claudin-18 antibody, to be conducted according to a standardized protocol. Patient with tumors with at least 50% of the cells were stained with at least 2+(double intensity) staining intensity were enrolled into this trial. The inclusion and exclusion criteria were checked during the screening visit (V1). Patients were recruited from university hospitals specialized in the treatment of gastroesophageal cancer.

Patients had to fulfill all of the following inclusion criteria:
  Metastatic, refractory or recurrent disease of advanced adenocarcinoma of the stomach or lower esophagus proven by histology
  CLDN18.2 expression confirmed by immunohistochemistry in paraffin embedded tumor tissue sample in at least 50% of the tumor cells with a staining intensity of at least 2+ (on a scale from 0 to 3+)
  At least 1 measurable site of disease according to RECIST criteria (CT scans or MRI not older than 2 weeks before visit 2)
  Age ≥18 years
  Written Informed consent
  ECOG performance status (PS) 0-1 or Karnofsky Index 70-100%
  Life expectancy >3 months
  Platelet count ≥100,000/mm$^3$
  Hemoglobin ≥10 g/dl
  Bilirubin normal
  AST and ALT <2.5 times upper limit of normal (ULN) (5 times ULN if liver metastases are present)
  Creatinine <1.5×ULN
  For women with childbearing potential (last menstruation less than 2 years prior to enrolment): Negative pregnancy test (β-HCG) at baseline and using two highly effective methods of contraception during the treatment phase and for 8 weeks after the last infusion of the study drug
  Male patients whose sexual partners were women of child bearing potential had to use an accepted contraceptive method during the treatment phase and for 8 weeks after the last infusion of the study drug Patients meeting any one or more of the following exclusion criteria were not eligible for study entry:
  Pregnancy or breastfeeding
  Prior severe allergic reaction or intolerance to a monoclonal antibody, including humanized or chimeric antibodies
  Less than 3 weeks since prior chemo- or radiation therapy
  Other investigational agents or devices concurrently or within 4 weeks prior to this study
  Other concurrent anticancer therapies (not for the indication under study treatment)
  Known HIV infection or known active hepatitis (A, B, C)
  Concurrent anticoagulation with vitamin K antagonists (e.g. Coumadin, Marcumar)
  Therapeutic doses of heparin (prophylactic doses are accepted)
  Uncontrolled illness including, but not limited to any of the following:
    Ongoing or active infection requiring parenteral antibiotics
    Symptomatic congestive heart failure
    Unstable angina pectoris
    Uncontrolled hypertension
    Clinically significant cardiac arrhythmia
    Myocardial infarction within the past 6 months
    Gastric bleeding within last four weeks
    Symptomatic peptic ulcer
    Clinical symptoms of cerebral metastasis
  Psychiatric illness or social situations that would preclude study compliance All patients of all cohorts received repeated doses of IMAB362 every two weeks on visits 2, 5, 6, 7 and 8 (5 applications). The dose escalation procedure comprehended the following cohorts with two different doses (antibody/body surface area) of IMAB362:
  Cohort 1: 300 mg/m$^2$
  Cohort 2: 600 mg/m$^2$
  Cohort 3: 600 mg/m$^2$ The antibody solution was given as a 2 h intravenous infusion every two weeks. It was important that the time of infusion was not less than 2 hours. For the infusion, an infusion system (e.g. Infusomat® fmS) had to be used in order to control the infusion time. The infusion set delivered with the study drug, which was tested for compatibility by the manufacturer, had to be used for the drug application. The time of the infusion of the study drug had to be in the morning. A qualified physician had to be available for the time during the infusion and 24 hours thereafter.

Thirty-seven patients received at least one treatment. Unfortunately for 3 of them the documentation is not completely in the database so that 34 patients will be included in the all patients treated set (APT set) and will be used for the safety analysis. Four, 6 and 24 patients were allocated respectively to cohort 1 with 300 mg/m$^2$ IMAB362, cohort 2 with 600 mg/m$^2$ IMAB362 and cohort 3 with 600 mg/m$^2$ IMAB362.

During the treatment phase one patient in cohort 1, three patients in cohort 2, and 12 patients in cohort 3 discontinued the study before having received 5 infusions of IMAB362 and completed visit 9 (incl. second tumor imaging) two weeks after the 5$^{th}$ infusion. These patients have been replaced.

Two patients in cohort 2 did not have measurable disease at baseline and were excluded from efficacy analysis. Minor protocol deviations such as baseline tumor evaluation >14 days earlier than Visit 2 (n=3; 8.8%), hemoglobin <10 g/dl (n=5; 14.7%), abnormal values for bilirubin (n=3, 8.8%), ALT or AST >2.5 ULN (>5 ULN in case of liver metastases) (n=2; 5.9%), a value for creatinine >1.5 ULN (n=1; 2.9%)

and prolonged time windows (>15 days) between screening period and start of treatment (n=2; 5.9%) occurred, but did not lead to exclusion from any analysis. One patient had a myocardial infarction within the last 6 months. A waiver was granted.

Since in cohort 2 and 3 the patients received the same dose of 600 mg/m², it was decided to analyze these patients as one group. All patients (n=34) of the APT set were Caucasian. The median age was 62 (range of 45-65 years) in the 300 mg/m² dose group and 61 (range of 42-77 years) in the 600 mg/m² dose group.

An overview of the localization of the cancer and the result of the histopathological grading is shown in Table 10. The median time period between first diagnosis and screening visit for this study was 16 months (min 2.7/max 56). The HER2/neu expression status was mostly unknown for the patients except for 5 patients treated with 600 mg/m². One of these 5 patients was HER2/neu positive.

TNM classification was specified for cancer of the stomach (n=16) and the esophagus or gastroesophageal junction (n=19). In the APT set 25% of the patients presented with primary tumors of the stomach classified with T1 or 2, 31% presented with T3, 25% with T4 primary tumors and for 19% it was unknown. Sixty-Nine (69) % of the patients in the APT set had at least one or two infiltrated lymph nodes indicated by the N1 classification and 56% of the patients suffered from peripheral metastases (M1) at the time of diagnosis. Sixty-nine (69) % of patients with cancer of the esophagus or gastroesophageal junction were diagnosed with ≥T3. At least one or two infiltrated lymph nodes (N1) were reported for 84% of the patients. In addition 84% of the patients presented with peripheral metastases.

TABLE 10

Overview of location and type of tumor at first diagnosis
(One patient had esophageal and stomach cancer; several patients had stomach cancer affecting different parts of the stomach)

|  | 300 mg/m² N (%) | 600 mg/m² N (%) | APT set N (%) |
|---|---|---|---|
| Number of patients | 4 | 30 | 34 |
| Esophagus | — | 2 (6.7) | 2 (6.7) |
| Gastroesophageal Junction | 1 (25.0) | 16 (53.3) | 17 (50.0) |
| distal | — | 4 | 4 |
| cardia | — | 8 | 8 |
| subcardia | 1 | 2 | 3 |
| unspecified | — | 2 | 2 |
| Stomach | 3 (75.0) | 13 (43.3) | 16 (47.1) |
| fundus | — | 2 | 2 |
| corpus | — | 6 | 6 |
| antrum | — | 3 | 3 |
| pylorus | — | — | — |
| unspecified | 3 | 6 | 9 |
| Type of tumor |  |  |  |
| intestinal | — | 8 | 8 |
| diffuse | 1 | 6 | 7 |
| signet ring cell CA | — | 4 | 4 |
| mixed | — | 1 | 1 |
| unspecified | 3 | 12 | 15 |
| Histopathological grading |  |  |  |
| G2 | — | 10 | 10 |
| G2-3 | 1 | 2 | 3 |
| G3 | 1 | 14 | 15 |
| G3-4 | — | 1 | 1 |
| Unknown | 2 | 3 | 5 |

On a MedDRA SOC basis, the most frequent clinically relevant previous diseases were surgical procedures in 25 patients (73.5%), chemotherapy in 30 patients (88.2%) and radiation in 7 patients (79.4%). In most cases, the surgery consisted of the surgical removal of organs (like gastrectomy (72%), oesophagectomy (16%), lymphadenectomy (32%), cholecystectomy (20%)).

All patients, except four, had at least one previous therapy for their study disease. On a WHO DD ATC basis, the most frequently used drugs were pyrimidine analogues (fluorouracil and/or capecitabine), platinum compounds (cisplatin and/or oxaliplatin), and detoxifying agents for antineoplastic treatment (calcium folinate and/or folinic acid). Other previous medicinal treatments (ending at the day of infusion at the latest) were also documented.

A total of 30 of the 34 patients (88.2%) had at least one concomitant disease, i.e. a disease that was ongoing at the day of infusion of study medication. On a MedDRA SOC basis, the most common diagnoses were 'gastrointestinal disorders' in 19 patients (56%), 'general disorders' in 12 patients (35%), 'metabolism and nutrition disorders' in 10 patients (29%) and 'musculoskeletal and connective tissue disorders' in 8 patients (23.5%). Concomitant therapies were mainly drugs for acid related disorders (17 patients; 50%), analgesics (12 patients; 35.3%) and medication for GI disorders (10 patients; 29.4%).

A. Safety Evaluation

Because the injections of the study medication were administered by the investigators at the study centers, and the patients had to stay in the hospital for observation for at least 24 hours and up to 72 hours, the overall compliance according to the study protocol was ensured. The assignment of the eligible subjects to the dose cohorts was exactly performed as specified by the study protocol (supervised by the DSMB). The study duration, defined as time from the date of screening visit part 1 to last study day ranged from min. 18 to max. 355 days. The median study duration was 106 days. 16 patients terminated the study prematurely before target visit 9.

Patients in all dose groups had a median number of 4.5 to 5 infusions of IMAB362. The median duration of one IMAB362 infusion in the APT set was 125 minutes. There was one patient with a duration of less than the 120 minutes specified in the protocol. This patient stopped the infusion due to vomiting, and prematurely discontinued the study.

The safety analysis was carried out for the APT set comprising all 34 patients who received at least one dose of 300 mg/m² (n=4) or 600 mg/m² (n=30). Two-hundred-forty-one (241) adverse events by physician's description were coded according to MedDRA dictionary and translated into preferred terms. Adverse events according to preferred terms have been counted only once for each patient (also if the same adverse event occurred more than once for that patient during the study). The highest NCI-CTC grade occurring in each patient was recorded. Thirty-two (32, 94%) patients had at least one adverse event (regardless of relationship) during the study. No adverse event was documented for 2 patients. Overall 6 patients (18%) did not experience a possibly drug related adverse event. One-hundred-four (104) drug related adverse events by preferred terms were reported for 28 patients. Eight (8) possibly drug related serious adverse events were reported for 4 patients. The number of patient in the lower dose group (300 mg/m²) was too small to allow detailed comparison between both dose groups. The incidence of patients with related adverse events in the 300 mg/m² cohort and the 600 mg/m² group (cohort 2 and 3) are 75 and 83% respectively.

In total, AEs from the SOCs 'gastrointestinal disorders' (27/34 patient 79.4%), 'general disorders and administration site conditions' (26/34 patients, 76.5%) were reported most frequently. On a MedDRA PT basis, the most frequently documented AEs were 'nausea' (57 events in 18 patients), 'vomiting' (52 events in 16 patients) and 'fatigue' (20 events in 14 patients). In total only 192 of the recorded AEs were assessed by the investigators as related to study medication. These treatment-related AEs were classified in 104 different preferred terms and were observed in 28/34 patients.

Most related adverse events were mild to moderate. There were 8 (23.5%) patients with moderate drug-related treatment emergent events and 12 (35.3%) patients with severe related treatment emergent events.

Drug related AEs of severe intensity were reported for 2 patients in the 300 mg/m$^2$ dose group, vomiting and in one patient concomitant nausea. In the 600 mg/m$^2$ dose group 10 patients experienced severe drug related adverse events, 6 patients with vomiting of whom 3 patients experienced in addition nausea, one patient with hypersensitivity (allergic reaction), one patient with salivary hypersecretion one patient with dehydration, and one patient with hypoalbuminia. The latter two patients also reported vomiting and nausea. Two patients suffered a related hypersensitivity (allergic reaction) during study drug infusion, one of which was classified as moderate and one as severe. Both patients recovered after infusion was stopped.

In all reported treatment-emergent events study drug action was necessary for 12/34 patients due to an AE. In 7 (21%) cases an AE led to permanent study discontinuation. The underlying adverse event was drug related in 3 (hypersensitivity (allergic reaction) (n=2), vomiting and abdominal pain) and not drug related in the other four patients (general physical health deterioration (n=3), pneumonia). In one patient dose was reduced and in another patient dose administration was delayed by 4 days due to serious vomiting with nausea. In three patients the infusion was interrupted/prolonged. Twenty-seven patients (79%) received concomitant therapy due to an AE. Eleven patients were hospitalized.

There were 13 patients with 31 SAEs documented. One patient died during the second screening phase of the study. Twelve patients had other serious adverse events, which were study drug related in four patients. Vomiting, nausea and related adverse events like GI hemorrhage and exsiccosis were judged by the investigators as related to study medication. There were 4 SARs, and 2 SUSARs (vomiting and vomiting with GI hemorrhage) in the present study. The final outcome was death in seven cases. None of the deaths were classified by the investigators as related to study medication.

One patient was a 45 old Caucasian male in good general condition (ECOG performance status grade 1, Karnofsky index 80%) with slim dietary status (BMI 19.3).

The patient received infusions with 300 mg/m$^2$ IMAB362 every two weeks on 4 November, on 22 November and the third on 6 Dec. 2011. Before the study the patient had already suffered from nausea and vomiting grade 1. On 7 Nov. 2010 vomiting grade 3 was diagnosed. As it was assessed as serious, the patient had to be hospitalized. When vomiting changed into grade 1 on 17 Nov. 2010 and finally stopped completely, the patient could be discharged from the hospital on the same day. Before the second and third IMAB362 infusion the patient was treated with a potent premedication (alizapride, aprepitant, metoclopramide, dimehydrinate) as prophylaxis for nausea and vomiting, so that he did not suffer from nausea or vomiting again. The investigator assessed the vomiting as related to study drug. The report was received by the sponsor on 19 Jan. 2011 and the SAE judged as not expected but related to study drug and therefore reported as a SUSAR.

One patient was a 77 year-old Caucasian male. He was in a very good general condition (ECOG Performance Status: grade 0, Karnofsky Index: 100%) with normal dietary status (BMI 24) at screening. Before the study, the patient already suffered from nausea and he was therefore treated as needed with metoclopramide. The patient received only one application of 600 mg/m$^2$ IMAB362 on 9 Nov. 2011, as the study had to be prematurely discontinued due to death. A pleural effusion in the left lung was diagnosed by X-ray before the infusion and reported as SAE. The next morning, haematemesis set on. After administration of pantoprazole and 8 mg ondansetron i.v., vomiting decreased and haematemesis recovered the same day. Vomiting decreased from grade 3 to grade 2 and finally stopped on 12 Nov. 2011, so that the patient could be discharged from hospital on 13 Nov. 2011. The investigator assessed the event as related to study drug. The report was received by the sponsor on 10 Nov. 2011 and the event judged as not expected but related to study drug and therefore reported as SUSAR. The general condition of the patient worsened, he developed renal failure and unfortunately died on 6 Dec. 2011.

One patient was a 42 year-old Caucasian male in very good general condition (ECOG performance status grade 0; Karnofsky index: 100%) with a well-nourished dietary status (BMI 26). The patient received two infusions of 600 mg/m$^2$ IMAB362. On 20 Mar. 2012 the patient received the first study drug application. As he suffered from nausea and serious vomiting, the infusion rate had to be reduced after 35 minutes of infusion. The symptoms were treated with 40 mg pantoprazole and 3 mg granisetron and 2 vials i.v. butylscopolamine and 80 mg i.v. aprepitant. This serious adverse event led to prolonged hospitalization. The investigator assessed this event as related to study drug. The SAE report was received by the sponsor on 21 Mar. 2012 and the event judged as expected and related to study drug. A few days later, on 24 Mar. 2012 the patient had to be hospitalized again due to serious dehydration, which was caused by nausea and vomiting. Furthermore the patient suffered from pain in the epigastrium. He received 1 g i.v. metamizol, a buprenorphine patch and infusions for rehydration. On 30 Mar. 2012 the symptoms were relieved and the patient rehydrated. The investigator assessed this event as not related to study drug. The SAE report was received by the sponsor on 26 Mar. 2012 and the event judged as not expected and not related to study drug. On 3 Apr. 2012 the patient received the second infusion, which led again to the AEs nausea and vomiting. He was treated with 30 drops p.o. metoclopraminde and 1 vial i.v. dimenhydrinat. As the symptoms worsened on 5 Apr. 2012, they were assessed as serious. In addition the patient was troubled with dysphagia and thus strongly reduced food-intake. On 15 Apr. 2012 the symptoms were gone. The investigator assessed this event as related to study drug. The SAE report was received by the sponsor on 19 Apr. 2012 and the event judged as expected and related to study drug.

One patient was a 73 year-old Caucasian male in good general condition (ECOG performance status grade 1; Karnofsky index: 90%) with a well-nourished dietary status (BMI 26). From 8 Nov. 2011 till 3 Jan. 2012 the patient received the five planned study drug applications of 600 mg/m$^2$ IMAB362 every two weeks. On 8 Nov. 2011 the patient received the first application of IMAB362. During and after this infusion, he suffered from nausea and vomiting. The symptoms became serious on 9 Nov. 2011. After treatment with metoclopramide the symptoms resolved one day later. The investigator assessed the event as related to study drug. The SAE report was received by the sponsor on 10 Nov. 2011 and the event judged expected and related to study drug. On 6 Dec. 2011 was the third infusion. The patient suffered from moderate vomiting and mild nausea treated with clemastine, ranitidine, and ondansetron. The vomiting lasted one day. The nausea continued for 7 days. The study was terminated on 16 Jan. 2012 due to disease progression. No follow up visit was performed.

In conclusion, IMAB362 was found to be safe and well tolerated in a heavy pretreated population of patients with advanced adenocarcinoma of the stomach, esophagus or gastroesophageal junction. In total, AEs from the SOCs 'gastrointestinal disorders' (27/34 patient 79.4%), 'general disorders and administration site conditions' (26/34 patients, 76.5%) were reported most frequently.

On a MedDRA PT basis, the most frequently documented AEs were 'nausea' (57 events in 18 patients), 'vomiting' (52 events in 16 patients) and 'fatigue' (20 events in 14 patients).

In total 192 of the recorded AEs were assessed by the investigators as related to study medication. These treatment-related AEs were observed in 28 of the 34 patients. Eighty-three (83) percent of these related AEs were gastrointestinal disorders (68%, 130 AEs) recorded in 25 patients and general disorders (15%, 29 AEs) recorded in 16 patients.

On a MedDRA PT basis most related adverse events were mild to moderate with nausea (50%), vomiting (47%), fatigue (27%), abdominal pain (15%), peripheral oedema (15%), decreased appetite (12%) and diarrhea (12%) occurring in more than 10% of the patients.

Two patients suffered a related hypersensitivity (allergic reaction) during study drug infusion, one of which was classified as moderate and one as severe. Both patients recovered after infusion was stopped.

No abnormal study drug related laboratory values of CTC grade 4 (life-threatening) or 5 (death) have been reported.

There were 12 (35.3%) patients with severe related treatment emergent events. Drug related AEs of severe intensity were reported for 2 patients in the 300 mg/m$^2$ dose group, vomiting and in one patient concomitant nausea. In the 600 mg/m$^2$ dose group 10 patients experienced severe drug related adverse events, 6 patients with vomiting of whom 3 patients experienced in addition nausea, one patient with hypersensitivity (allergic reaction), one patient with salivary hypersecretion, one patient with dehydration, and one patient with hypoalbuminia. The latter two patients also reported vomiting and nausea.

At the time of analysis 13 patients have recovered from all drug related adverse events, 2 patients were recovering, 11 patients did not recover from at least one AE and for 2 the status was unknown.

Of the 11 patients where at least one drug related adverse event was not recovered 9 had gastrointestinal disorders (4 nausea, 2 vomiting).

There were 13 patients with 31 SAEs documented, including 7 deaths. One patient died during the screening phase, i.e. prior to the start of study drug infusion, and was therefore classified as screening event. In four patients treatment emergent gastrointestinal SAEs like vomiting (n=4), nausea (n=2), exsiccosis (n=1) and GI haemorrhage (n=1) were judged as treatment related. One of these patients with vomiting was treated with 300 mg/m$^2$ the other three were treated with 600 mg/m$^2$ IMAB362. Three of these four patients recovered except one who died due to a not related renal failure.

The incidence of drug related adverse events was comparable between the 300 and 600 mg/m$^2$ dose group with 75% and 83% of the patients, respectively. The frequency and severity of nausea, vomiting and fatigue was also comparable between both dose groups. There was no clear relationship between the dose and frequency/severity of adverse events.

The adverse event profile with most AEs reported for the gastrointestinal tract matches with the underlying disease and also the CLDN18.2 expression profile. It is suggested that nausea and vomiting are an on-target effect since CLDN18.2 is also expressed on gastric epithelial cells (in tight junctions).

Generally speaking, IMAB362 given in multiple doses of 300 and 600 mg/m$^2$ was observed to be safe and well-tolerated with vomiting and nausea being the most common related adverse event.

B. Evaluation of Pharmacokinetics and Immunogenicity

Preliminary drug concentration data for repeated dose application of IMAB362 is available for the four patients of the first and 34 patients of the second and third cohort, who received 300 mg/m$^2$ and 600 mg/m$^2$ IMAB362, respectively.

TABLE 11

$C_{max}$ (maximum serum drug concentration) following first and fifth IMAB362 administration

| Cohort/dose | Patient | cmax after 1st infusion [µg/mL] | | cmax after 5th infusion [µg/mL] | |
| --- | --- | --- | --- | --- | --- |
| Cohort 1 [300 mg/m$^2$] | 1001-01 | 349.6 | ±179.2** | 293.9 | ±26.9 |
| | 1001-07 | 341.6 | ±22.1 | n.a. | n.a. |
| | 2002-02 | 253.3 | ±7.1 | 326.5 | ±3.6 |
| | 1001-10 | 208.9 | ±3.2 | 259.1 | ±8.2 |
| Cohort 2 [600 mg/m$^2$] | 1005-03 | 343.6 | ±10.8 | n.a. | n.a. |
| | 1005-04 | 256.9 | ±5.7 | n.a. | n.a. |
| | 1005-11 | n.a. | n.a. | n.a. | n.a. |
| | 1001-08 | 325.1 | ±12.6 | 485.4 | ±6.7 |
| | 2002-05 | 272.2 | ±3.6 | 642.6 | ±17.9 |
| | 2002-07 | 325.3 | ±10.0 | 516.7 | ±1.9 |
| Cohort 3 [600 mg/m2] | 1011-05 | 296.1 | ±13.7 | 385.8 | ±15.1 |
| | 1013-02 | 310.9 | ±4.7 | 428.0 | ±17.9 |
| | 4001-11 | 323.4 | ±8.9 | n.a. | n.a. |
| | 1005-10 | 389.8 | ±0.7 | 457.6 | ±8.0 |
| | 1001-24 | 390.8 | ±6.7 | 433.8 | ±6.6 |
| | 1001-27 | 309.3 | ±10.7 | n.a. | n.a. |

TABLE 11-continued $C_{max}$ (maximum serum drug concentration) following first and fifth IMAB362 administration

| Cohort/dose Patient | cmax after 1st infusion [µg/mL] | | cmax after 5th infusion [µg/mL] | |
|---|---|---|---|---|
| 1003-10 | 300.7 | ±2.1 | n.a. | n.a. |
| 1004-07 | n.a. | n.a. | n.a. | n.a. |
| 1004-10 | 448.3 | ±5.7 | n.a. | n.a. |
| 1004-11 | n.a. | n.a. | n.a. | n.a. |
| 1005-18 | 269.2 | ±6.7 | n.a. | n.a. |
| 1005-26 | n.a. | n.a. | n.a. | n.a. |
| 1005-27 | 473.6 | ±10.6 | n.a. | n.a. |
| 1005-29 | 280.2 | ±16.7 | n.a. | n.a. |
| 1005-34 | 385.5 | ±18.8 | n.a. | n.a. |
| 1006-03 | 317.0 | ±14.8 | 278.1 | ±8.9 |
| 1006-05 | 276.0 | ±18.2 | n.a. | n.a. |
| 1007-09 | 397.0 | ±12.5 | n.a. | n.a. |
| 1011-09 | 411.1 | ±12.1 | 535.9 | ±17.0 |
| 1011-16 | 322.5 | ±8.5 | 314.5 | ±15.6 |
| 1011-17 | 462.3 | ±10.6 | n.a. | n.a. |
| 1011-20 | 347.9 | ±14.4 | 570.3 | ±10.1 |
| 1012-01 | 433.7 | ±9.7 | n.a. | n.a. |
| 2003-08 | 575.1 | ±30.7 | n.a. | n.a. |
| 2003-10 | 421.8 | ±3.4 | 520.5 | ±6.5 |
| 2003-13 | 344.7 | ±21.6 | n.a. | n.a. |
| 2003-15 | 380.9 | ±3.1 | n.a. | n.a. |
| 2003-16 | 466.8 | ±6.8 | n.a. | n.a. |

**high CV results from one outlier in the triplicate measurement

Blood samples have been drawn prior to every infusion. After the first infusion additional samples were taken at the end of the infusion and 1, 1.5, 2, 3, 4, 6, 12, 24 hours, 3 and 6 days after the end of the infusion. After the last infusion samples were taken at the end of the infusion and 1, 1.5, 2 hours and 14 days as well as 4 to 8 weeks after the end of the last infusion. No analyte could be detected in the pre-dose samples from individual patients allocated to cohort 1-3.

After the first IMAB362 infusion, $c_{max}$ values ranged between 208.9 µg/mL and 349.6 µg/mL for the first cohort. For the second and third cohort, taken together, $c_{max}$ values ranged between 269.1 µg/mL and 575.1 µg/mL after the first application.

Figure 8:
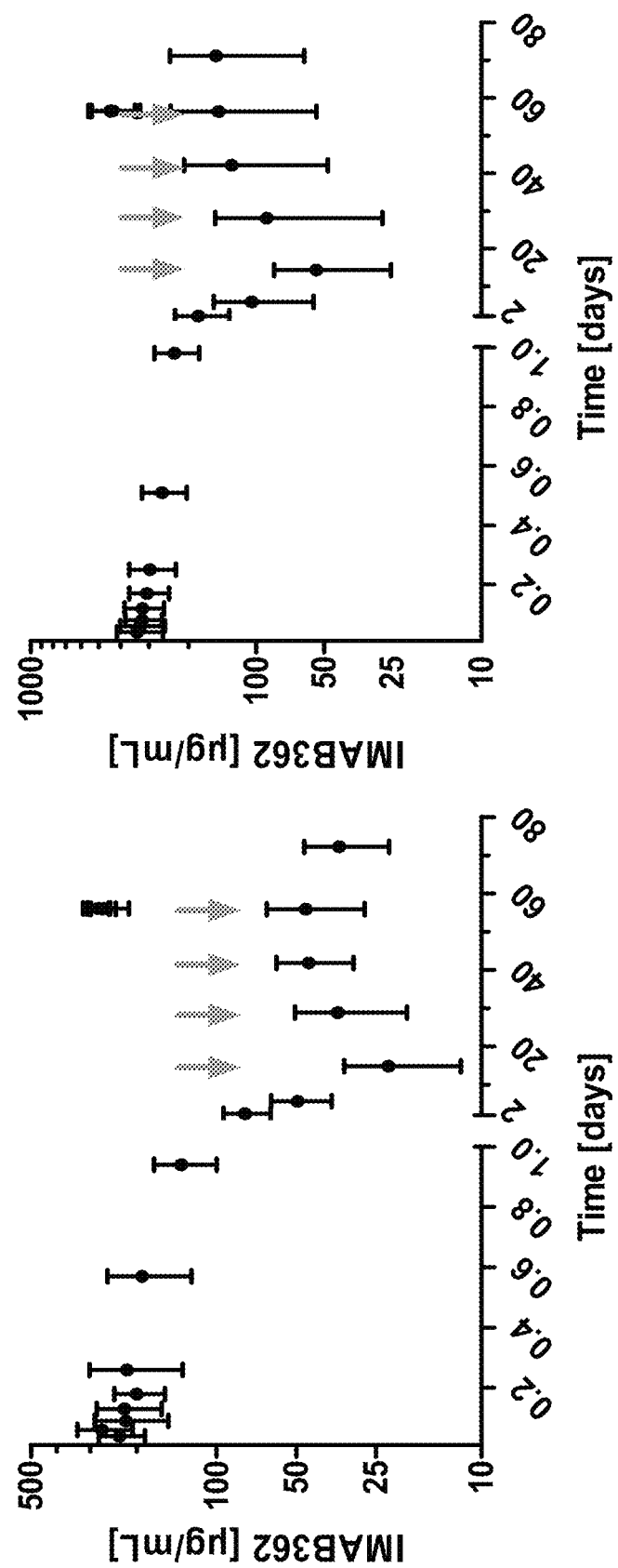
FIG. 8 shows pharmacokinetic results of repeated infusions of IMAB362 in patients. Mean±sd concentration (µg/ml) of IMAB362 in serum of 4 patients treated with repeated doses of 300 mg/m2 (cohort 1, left figure) and up to 30 patients (30 patients first infusion, 12 patients fifth infusion) treated with repeated doses of 600 mg/m² (cohort 2 and cohort 3 together, right figure). Arrows indicate the IMAB362 infusions. First infusion was given on day 0.

In serum samples taken at subsequent time points (V3 to V5), a time dependent reduction of the concentration of IMAB362 was observed (FIG. 8). At visit 5 before the second infusion, minimum serum levels between 11.3 µg/mL and 36.8 µg/mL (mean value 22.5±10.5 µg/mL) were determined for cohort 1 and 17.0 µg/mL and 100.2 µg/mL (mean value 54.5±29.0 µg/mL) for cohort 2 and 3 taken together.

At visit 8 (day 57) before fifth infusion minimum serum levels between 32.4 µg/mL and 67.1 µg/mL (mean value 46.1±18.5 µg/mL) were determined for cohort 1 and 28.3 µg/mL and 301.6 µg/mL (mean value 147.2±93.1 µg/mL) for cohort 2 and 3 (Table 12).

After infusion at visit 8, $c_{max}$ values ranged between 259.1 µg/mL and 326.5 µg/mL for the first cohort and 278.1 µg/mL and 642.6 µg/mL for cohort 2 and 3 (Table 11).

For cohort 1, mean $C_{max}$ values were determined 90 min after the first IMAB362 infusion (270.6±63.9 µg/mL) and 90 min after the fifth infusion (279.2±27.7). For cohort 2 and 3 together, mean $C_{max}$ values were determined at the end of the first IMAB362 infusion (340.8±80.2 µg/mL) and 60 min after the fifth infusion (443.3±97.7) (Table 12).

In summary, measured serum levels of IMAB362 showed, that in the patients treated with 300 mg/m² the serum concentration of IMAB362 drops below the desired level of 50-100 µg/ml in between 2-weekly cycles. At a dose of 600 mg/m², in contrast, in the vast majority of patients IMAB362 serum levels were above 50 µg/ml, even 2 weeks after the first application. Seven to 29 days (mean value 15 days) after the 5th administration, the dose level was above 50 µg/ml (mean value 151.3±90.1 µg/mL).

TABLE 12

Descriptive pharmacokinetic data of repeated administration of 300 and 600 mg/m² IMAB362
Mean ± sd concentration (µg/ml) of IMAB362 in serum of 4 patients treated with repeated doses of 300 mg/m² (cohort 1) and up to 30 patients (30 patients first infusion, 12 patients fifth infusion) treated with repeated doses of 600 mg/m² (cohort 2 and cohort 3 together).

| Dose IMAB362 | Concentration (mean ± sd) IMAB362 [µg/ml] | |
|---|---|---|
| | 300 mg/m² | 600 mg/m² |
| $c_{max}$ after 1st infusion | 270.6 ± 63.9 | 340.8 ± 80.2 |
| Pre-dose level before 2nd infusion | 22.5 ± 10.5 | 54.3 ± 29.0 |
| Pre-dose level before 3rd infusion | 34.9 ± 15.8 | 89.9 ± 62.3 |
| Pre-dose level before 4th infusion | 44.9 ± 14.5 | 128.7 ± 80.6 |
| Pre-dose level before 5th infusion | 46.1 ± 18.5 | 147.2 ± 93.1 |
| $c_{max}$ after 5th infusion | 279.2 ± 27.7 | 443.3 ± 97.7 |
| after 5th administration | 34.5 ± 12.2 | 151.3 ± 90.1 |

A mild accumulation of IMAB362 was observed from cycle to cycle. Accumulation factors ranged from 1.03 fold to 3.52 fold based on the first pre-dose value before second infusion (mean value 2.04).

TABLE 13

Accumulation of IMAB362 after repeated infusions
To determine accumulation factors, IMAB362 concentration ratios before visits 6, 7, 8 and 9.x (responder treatment) and before second infusion (visit 5) were calculated.

| Cohort 3 | | pre-infusion | | | | | | |
|---|---|---|---|---|---|---|---|---|
| Accumulation factor Patient | Production clone | V6/V5 | V7/V5 | V8/V5 | V9.1/V5 | V9.2/V5 | V9.3/V5 | V9.4/V5 |
| Patient 101105 | F02 | 1.73 | 2.10 | 2.16 | | | | |
| Patient 101302 | F02 | 1.78 | 2.36 | 2.08 | 1.70 | 1.82 | 2.03 | 2.28 |
| Patient 400111 | F02 | 2.04 | 2.44 | | | | | |
| Patient 100510 | #15 | 1.83 | 2.41 | 2.24 | | | | |
| Patient 100124 | #15 | 2.33 | 2.69 | 2.42 | 1.98 | 3.17 | 2.54 | 1.49 |
| Patient 100410 | #15 | 3.05 | | | | | | |
| Patient 100529 | F02 | 1.49 | 1.66 | | | | | |
| Patient 100603 | F02 | 1.21 | 1.39 | 1.66 | 1.92 | 3.52 | | |
| Patient 100605 | F02 | 1.12 | 1.83 | | | | | |

TABLE 13-continued

Accumulation of IMAB362 after repeated infusions
To determine accumulation factors, IMAB362 concentration ratios before visits 6, 7, 8
and 9.x (responder treatment) and before second infusion (visit 5) were calculated.

| Cohort 3 | | pre-infusion | | | | | | |
|---|---|---|---|---|---|---|---|---|
| Accumulation factor | Production clone | V6/V5 | V7/V5 | V8/V5 | V9.1/V5 | V9.2/V5 | V9.3/V5 | V9.4/V5 |
| Patient 101109 | #15 | 2.12 | 2.70 | 2.29 | | | | |
| Patient 101120 | #15 | 1.71 | 2.12 | 2.39 | | | | |
| Patient 200310 | #15 | 1.03 | 1.35 | 1.30 | | | | |

In conclusion, pharmacokinetics of IMAB362 was found to be dose-dependent.

After the first IMAB362 infusion, $c_{max}$ values ranged between 208.9 μg/mL and 349.6 μg/mL for the first cohort. For the second and third cohort, taken together, $c_{max}$ values ranged between 269.1 μg/mL and 575.1 μg/mL after the first application.

In serum samples taken at subsequent time points (V3 to V5), a time dependent reduction of the concentration of IMAB362 was observed. At visit 5 before the second infusion, minimum serum levels between 11.3 μg/mL and 36.8 μg/mL (mean value 22.5±10.5 μg/mL) were determined for cohort 1 and 17.0 μg/mL and 100.2 μg/mL (mean value 54.5±29.0 μg/mL) for cohort 2 and 3 taken together.

At visit 8 (day 57) before fifth infusion minimum serum levels between 32.4 μg/mL and 67.1 μg/mL (mean value 46.1±18.5 μg/mL) were determined for cohort 1 and 28.3 μg/mL and 301.6 μg/mL (mean value 147.2±93.1 μg/mL) for cohort 2 and 3.

After 5th infusion at visit 8, $c_{max}$ values ranged between 259.1 μg/mL and 326.5 μg/mL for the first cohort and 278.1 μg/mL and 642.6 μg/mL for cohort 2 and 3.

For cohort 1, mean $C_{max}$ values were determined 90 min after the first IMAB362 infusion (270.6±63.9 μg/mL) and 90 min after the fifth infusion (279.2±27.7). For cohort 2 and 3 together, mean $C_{max}$ values were determined at the end of the first IMAB362 infusion (340.8±80.2 μg/mL) and 60 min after the fifth infusion (443.3±97.7).

In summary, measured serum levels of IMAB362 showed, that in the patients treated with 300 mg/m² the serum concentration of IMAB362 drops below the desired level of 50-100 μg/ml in between 2-weekly cycles. At a dose of 600 mg/m², in contrast, in the vast majority of patients IMAB362 serum levels were above 50 μg/ml, even 2 weeks after the first application. Seven to 29 days (mean value 15 days) after the 5$^{th}$ administration, the dose level was above 50 μg/ml (mean value 151.3±90.1 μg/mL).

C. Evaluation of Antitumoral Activity

Full Analysis Set (FAS):

Included all subjects who have received study medication at least once and for whom efficacy data upon treatment were available.

At the time of analysis 50 patients have been enrolled at a dose of 600 mg/m². Nine of them have been included recently and no further data is available at the moment due to their recent enrolment. For ten patients no second tumor imaging has been performed and these patients are therefore not included in the FAS set. The FAS set comprises 31 patients.

The median age was 57 years with a range from 35 to 77. Patients of the FAS set had a median Karnofsky-Index of 90% (range from 70-100%). The vast majority (81%) of the patients has been pretreated with at least one chemotherapy regimen. Six (6) patients did not have a previous chemotherapy regimen.

TABLE 14

Details on previous chemotherapy regimens in the FAS set (n = 31).

| | 5-FU/ Capecitabine | Platinum Compound | Taxanes | Epirubicin | Irinotecan | mABs/other agents |
|---|---|---|---|---|---|---|
| No. of patients | 25 (81%) | 23 (74%) | 14 (45%) | 8 (26%) | 8 (26%) | 6 (19%) |

The median number of previous chemotherapy regimens was 2.0 (range 0 to 5). Chemotherapy regimens for gastroesophageal cancer mostly consist of various combinations of 5-FU derivative, platinum compound, taxanes, epirubicin, irinotecan, trastuzumab for HER2/neu positive patients and other investigational agents. In the FAS set 81% of patients had at least once 5-FU or capecitabine and 74% were treated with a platinum compound at least once prior to inclusion. Six (6, 19%) patients have been pretreated with trastuzumab or other investigational agents. Six (6, 19%) patients also had radiotherapy before study start.

Due to the late stage of the disease the patients had a median of 2.0 metastatic sites (range from 1.0 to 4.0). Most prominent were lymph nodes (19 pts, 61%); liver (13 pts, 42%); ascites (8 pts, 26%) and peritoneum (7 pts, 23%).

The overall disease control rate was 39% (Table 15). Four patients had confirmed partial response, and 8 patients had a stabilization of disease. The first re-assessment for these patients took place 8 to 11 weeks after first infusion, except for two patients, for whom it the first tumor re-assessment was done after 6 weeks, respectively.

TABLE 15

Best response evaluation according to RECIST, FAS set

| Best Response | n | % |
|---|---|---|
| PR | 4 | 13 |
| SD | 8 | 26 |
| PD | 19 | 62 |
| Total | 31 | 100 |

In 6 of the 12 patients with clinical disease control at least one tumor marker (CEA; CA19-9; CA125; CA15-3) which was elevated at baseline dropped by 35 to 76% throughout the study. In three patients all tumor markers were below the cut-off value and for one patient no tumor marker results were available.

Interestingly also 4 patients with progressive disease as best response had a tumor marker decrease between 29 and 54% during the study.

Partial responses were reached after 2.3 months treatment (two patients), 6.5 months (one patient) and 4.8 months (one patient) respectively. The PR was confirmed for one patient, lasted another 4.4 months, which leads to a PFS of 9.2 months for this patient. For the other three patients confirmations were done after 6 (one patient) and 12 weeks (two patients), respectively. More details can be found in Table 16.

TABLE 16

Detailed evaluation of the FAS set on a per patient basis

| Pat-No. | No. of Inf. | No. of prev Tx | No. of met. sites | Max. | IHC Mean no. of cells | Status at entry | Best Response RECIST (change) | Best Response Tumor marker | PFS [weeks] | OS [months] |
|---|---|---|---|---|---|---|---|---|---|---|
| 2002-05 | 17 | 0 | 2 | 3 | 87 | n.a. | SD (n.d.) | CA125 −59%# | 40 | |
| 1001-08 | 11 | 4 | 2 | 3 | 83 | PD | SD (±0%) | CA19-9 −35% | 23 | |
| 1007-02 | 16 | 1 | 2 | 2 | 70 | SD | PR (−51%) | CA15_3 −65%# | 40 | |
| 4001-12 | 2 | 2 | 2 | 2 | 63 | n.a. | SD (+18%) | n.a. | 6 | 6.4[1] |
| 1013-02 | 9 | 5 | 4 | 3 | 68 | n.a | SD (+5%) | increase | 18 | |
| 1011-09 | 5 | 0 | 3 | 3 | 67 | PD | SD (−25%) | CA125 −25% | 10* | |
| 1001-24 | 8 | 2 | 4 | 2 | 50 | PD | SD (0%) | increase | 16* | 5.6[1] |
| 1006-03 | 17 | 3 | 3 | 3 | 70 | SD | PR (−34%) | CA125 −37% | 34* | |
| 1007-09 | 11 | 1 | 2 | 3 | 73 | SD | SD (n.a.) | CA15_3 −42%# | 23* | |
| 2003-15 | 11 | 0 | 3 | 3 | 80 | PD | PR (−35%) | CA125 −35% | 22* | |
| 2003-16 | 11 | 1 | 4 | 2 | 90 | PD | PR (−39%) | CA19-9 −76% CA125 −75% | 22* | |
| 1005-34 | 5 | 4 | 3 | 2 | 50 | SD | SD (+17%) | CEA −35% | 11* | |
| 2002-07 | 5 | 0 | 1 | 2 | 50 | PD | PD (n.d.) | n.d. | 11 | |
| 4001-09 | 5 | 0 | 1 | 2 | 40 | PD | PD (+40%) | increase | 10 | |
| 1005-13 | 5 | 5 | 2 | 3 | 65 | n.a. | PD (+63%) | increase | 10 | |
| 4001-01 | 5 | 2 | 3 | 2 | 60 | PD | PD (+60%) | n.d. | 9 | |
| 1004-10 | 3 | 1 | 4 | 2 | 83 | SD | PD (+4%) | increase | 6 | |
| 1005-10 | 5 | 4 | 2 | 3 | 53 | PD | PD (−2%) | CA15_3 −40% CA125 −54% | 10 | |
| 1004-11 | 5 | 1 | 3 | 2 | 40 | n.a. | PD (+32%) | CA19_9 −32% | 10 | 4.3 |
| 4001-11 | 4 | 4 | 3 | 3 | 80 | n.a. | PD (+6%) | CA15_3 −49%; | 7 | |
| 1011-05 | 5 | 1 | 2 | 2 | 58 | n.a. | PD (+72%) | increase | 10 | |
| 1009-01 | 4 | 1 | 1 | 3 | 63 | SD | PD (+71%) | increase | 8 | |
| 1011-16 | 5 | 2 | 1 | 3 | 75 | PD | PD (−26%) | CEA −29% CA15_3 −28% | 9 | 3.8 |
| 1012-01 | 3 | 2 | 1 | 2 | 50 | n.a. | PD (+12%) | increase | 7 | |
| 1005-18 | 3 | 3 | 3 | 3 | 60 | PD | PD (+3%) | increase | 5 | |
| 2003-10 | 5 | 0 | 4 | 2 | 60 | n.a. | PD (+8%) | increase | 10 | |
| 1011-20 | 5 | 2 | 1 | 3 | 48 | n.a. | PD (+82%) | increase | 9 | |
| 1003-10 | 2 | 2 | 2 | 3 | 50 | n.a. | PD (n.a.) | n.a. | 4* | |
| 1001-27 | 3 | 4 | 4 | 3 | 73 | n.a. | PD (n.a.) | n.a. | 5* | 1.6 |
| 1006-05 | 5 | 3 | 3 | 3 | 60 | n.a. | PD (+73%) | increase | 10* | 4.3 |
| 1005-29 | 3 | 3 | 2 | 3 | 75 | SD | PD (+3%) | increase | 7 | | n.a.—data not available yet;
n.d.—not detectable.
*—censored since event did not take place until November 2012 or exact date is unknown at the moment. Last date of follow-up has been used in every case.
—tumor marker is below cut-off. Have not been counted in the text due to that.

Figure 9:
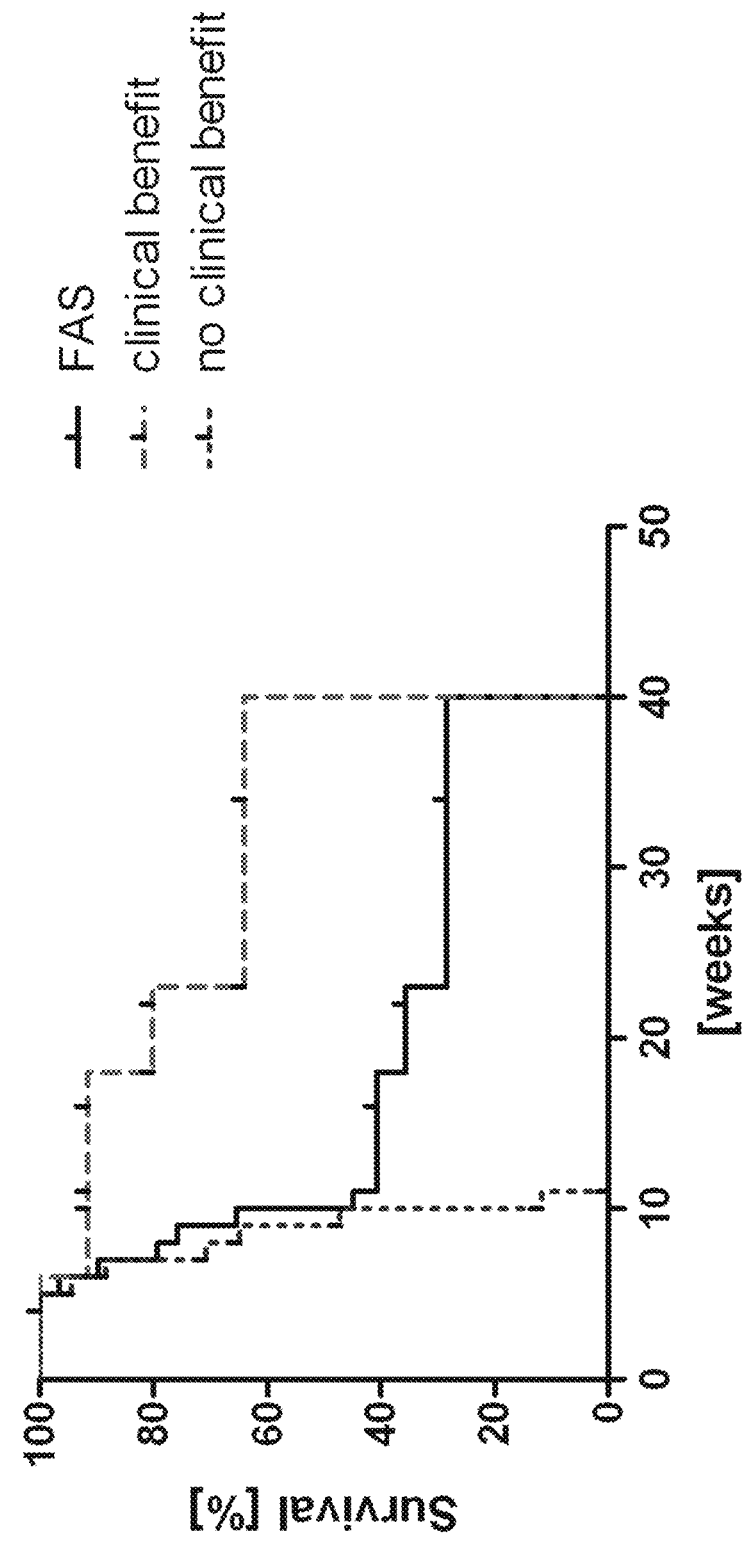
FIG. 9 shows progression free survival of patients in the full analysis set (FAS).

The median progression free survival for patients in the FAS set was 10 weeks (min. 4 weeks; max. 40 weeks). Due to restricted availability of events the median progression free survival for patients with clinical benefit (PR+SD) shown in FIG. 9 has limited value. Patients without clinical benefit (PD) had a median progression free survival of 9 weeks (min. 4 weeks; max. 11 weeks) (FIG. 9).

There was no differences between patients with clinical benefit (PR or SD as best response) or progressive disease (PD as best response) with regard to age (mean of 56 vs. 59 years), no of previous chemotherapy regimen (mean of 1.9 vs. 2.1), Karnofsky-Index (mean of 89 vs. 88%). Only the number of metastatic sites was lower in the responder group with a mean of 1.9 in comparison to 2.3 in the non-responder group. The difference is not statistically significant.

The intensity (mean and max) of IHC staining was similar between patients with clinical benefit and progressive disease. The number of cells stained was different between both groups. The maximum number of cells stained and the mean number of cells stained were higher in the patients with clinical benefit with a mean of 77% vs. 67% and 71% vs. 60%, respectively.

Differences were also observed regarding location of the metastases. In the patients with clinical benefit the frequency of pleural effusion (25% vs. 5%), peritoneal carcinomatosis (42% vs. 11%) and ascites (42% vs. 16%) was higher compared to patients with progressive disease as best response. The presence of liver metastases was much lower (17% vs. 58%) in patients with clinical benefit.

Per Protocol Set (PP):

The PP population included all patients who completed the treatment section (up to visit 9) without any major protocol deviation.

Of the 31 patients in the FAS set two had a major protocol violation (no target lesion) and nine patients did not complete the study protocol until visit 9, and therefore they had less than the 5 required infusions of IMAB362. The PP set comprises 20 patients.

The median age was 60 years with a range from 35 to 77. Patients of the PP set had a median Karnofsky-Index of 90% (range from 70-100%). The vast majority (80%) of the patients has been pretreated with at least one chemotherapy regimen. Four (4) patients did not have a previous chemotherapy regimen.

TABLE 17

Details on previous chemotherapy regimens in the PP set (n = 20).

|  | 5-FU/ Capecitabine | Platinum Compound | Taxanes | Epirubicin | Irinotecan | mABs/other agents |
|---|---|---|---|---|---|---|
| No. of patients | 16 (80%) | 15 (75%) | 11 (55%) | 4 (20%) | 5 (25%) | 5 (25%) |

The median number of previous chemotherapy regimens was 2.0 (range 0 to 5). Chemotherapy regimens for gastroesophageal cancer mostly consist of various combinations of 5-FU derivative, platinum compound, taxanes, epirubicin, irinotecan, trastuzumab for HER2/neu positive patients and other investigational agents. In the PP set 80% of patients had at least once 5-FU or capecitabine and 75% were treated with a platinum compound at least once prior to inclusion. Five (5, 25%) patients have been pretreated with trastuzumab or other investigational agents. More details can be found in Table 17. Five (5, 25%) patients also had radiotherapy before study start.

Due to the late stage of the disease the patients had a median of 3.0 metastatic sites (range from 1.0 to 4.0). Most prominent were lymph nodes (13 pts, 65%); liver (9 pts, 45%); ascites (6 pts, 30%) and lung (5 pts, 25%).

The overall disease control rate was 50%. Four patients had confirmed partial response and 6 stabilization of disease. The first re-assessment for these patients took place 8 to 11 weeks after first infusion, except for one patient, for whom the first tumor re-assessment was done after 6 weeks, respectively (Table 18).

TABLE 18

Best response evaluation according to RECIST, PP set.

| Best Response | N | % |
|---|---|---|
| PR | 4 | 20 |
| SD | 6 | 30 |
| PD | 10 | 50 |
| Total | 20 | 100 |

In 6 of the 10 patients with clinical disease control at least one tumor marker (CEA; CA19-9; CA125; CA15-3) which was elevated at baseline dropped by 35 to 76% throughout the study. In two patients all tumor markers were below the cut-off value and for one patient no tumor marker results were available.

Interestingly also 3 patients with progressive disease as best response had a tumor marker decrease between 29 and 54% during the study.

Partial responses were reached after 2.3 months treatment (two patients), 6.5 months (one patient) and 4.8 months (one patient) respectively. The PR was confirmed for one patient, lasted another 4.4 months, which leads to a PFS of 9.2 months for this patient. For the other three patients confirmations were done after 6 (one patient) and 12 weeks (two patients), respectively. More details can be found in Table 19.

TABLE 19

Detailed evaluation of the PP set on a per patient basis

| Pat-No. | No. of Inf. | No. of prev Tx | No. of met. sites | IHC Mean Max. | IHC no. of cells | Status at entry | Best Response RECIST (change) | Best Response Tumor marker | PFS [weeks] | OS [months] |
|---|---|---|---|---|---|---|---|---|---|---|
| 1001-08 | 11 | 4 | 2 | 3 | 83 | PD | SD (±0%) | CA19-9 −35% | 23 | |
| 1007-02 | 16 | 1 | 2 | 2 | 70 | SD | PR (−51%) | CA15_3 −65%# | 40 | |
| 1013-02 | 9 | 5 | 4 | 3 | 68 | n.a | SD (+5%) | increase | 18 | |
| 1011-09 | 5 | 0 | 3 | 3 | 67 | PD | SD (−25%) | CA125 −25% | 10* | |
| 1001-24 | 8 | 2 | 4 | 2 | 50 | PD | SD (±0%) | increase | 16* | 5.6[1] |
| 1006-03 | 17 | 3 | 3 | 3 | 70 | SD | PR (−34%) | CA125 −37% | 34* | |
| 1007-09 | 11 | 1 | 2 | 3 | 73 | SD | SD (n.a.) | CA15_3 −42%# CA125 −27%# | 23* | |
| 2003-15 | 11 | 0 | 3 | 3 | 80 | PD | PR (−35%) | CA125 −35% | 22* | |
| 2003-16 | 11 | 1 | 4 | 2 | 90 | PD | PR (−39%) | CA19-9 −76% CA125 −75% | 22* | |
| 1005-34 | 5 | 4 | 3 | 2 | 50 | SD | SD(+17%) | CEA −35% CA 125 −11% | 11* | |
| 4001-09 | 5 | 0 | 1 | 2 | 40 | PD | PD (+40%) | increase | 10 | |
| 1005-13 | 5 | 5 | 2 | 3 | 65 | n.a. | PD(+63%) | increase | 10 | |
| 4001-01 | 5 | 2 | 3 | 2 | 60 | PD | PD(+60%) | n.d. | 9 | |
| 1005-10 | 5 | 4 | 2 | 3 | 53 | PD | PD (−2%) | CA15_3 −40% CA125 −54% | 10 | |
| 1004-11 | 5 | 1 | 3 | 2 | 40 | n.a. | PD(+32%) | CA19_9 −32% | 10 | 4.3 |
| 1011-05 | 5 | 1 | 2 | 2 | 58 | n.a. | PD(+72%) | increase | 10 | |
| 1011-16 | 5 | 2 | 1 | 3 | 75 | PD | PD(−26%) | CEA −29% CA15_3 −28% | 9 | 3.8 |
| 2003-10 | 5 | 0 | 4 | 2 | 60 | n.a. | PD (+8%) | increase | 10 | |
| 1011-20 | 5 | 2 | 1 | 3 | 48 | n.a. | PD(+82%) | increase | 9 | |
| 1006-05 | 5 | 3 | 3 | 3 | 60 | n.a. | PD(+73%) | increase | 10* | 4.3 | n.a.—data not available yet;
n.d.—not detectable.
*—censored since event did not take place until November 2012 or exact date is unknown at the moment. Last date of follow-up has been used in every case.
—tumor marker is below cut-off. Have not been counted in the text due to that.
[1] Measurements were done earliest after 4 weeks and every 3-12 weeks thereafter throughout the study.

Figure 10:
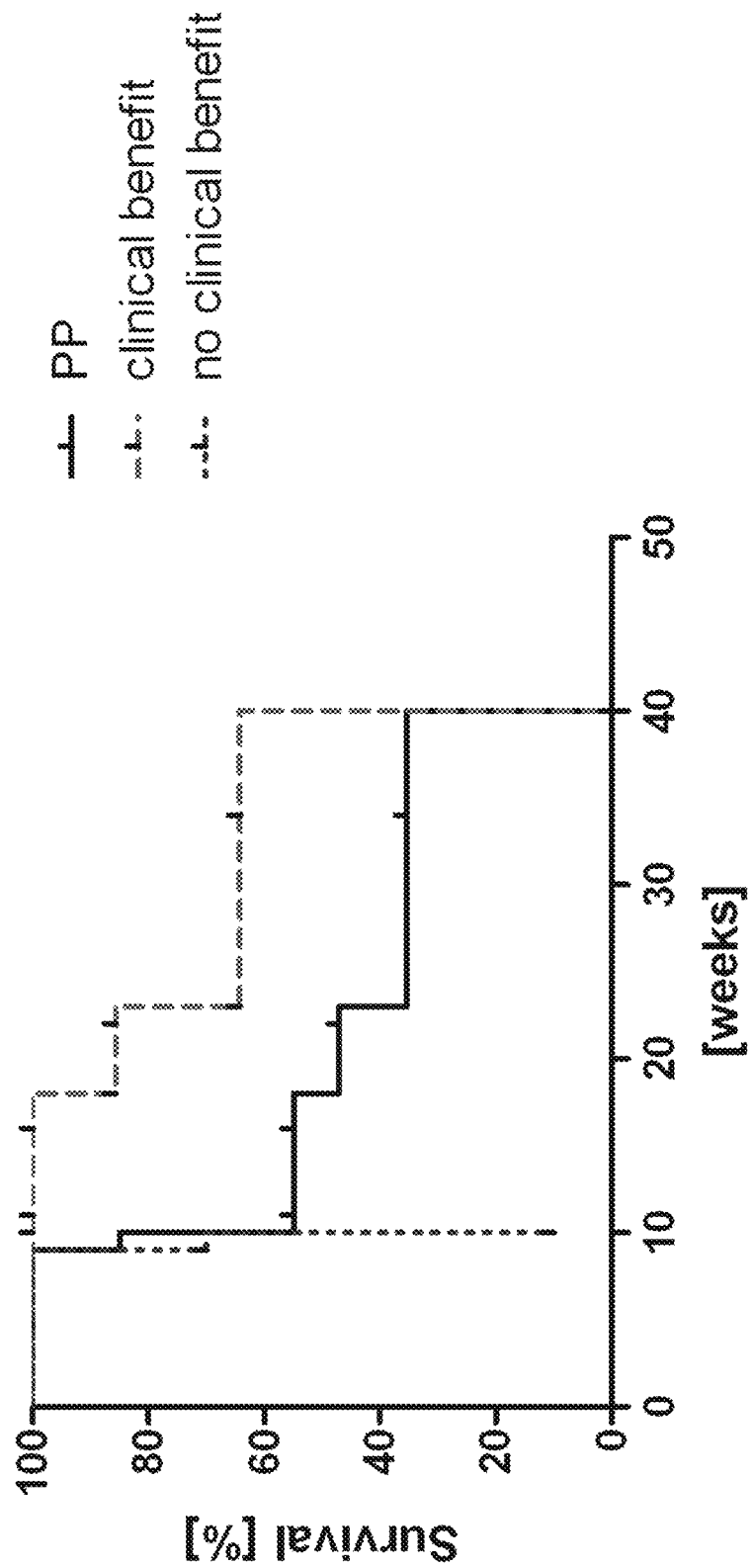
FIG. 10 shows progression free survival of patients in the per protocol (PP) set (n=20).

The median progression free survival for patients in the PP set was 18 weeks (min. 9 weeks; max. 40 weeks). Due to restricted availability of events the median progression free survival for patients with clinical benefit (PR+SD) shown in FIG. 10 has limited value. Patients without clinical benefit (PD) had a median progression free survival of 10 weeks (min. 9 weeks; max. 10 weeks) (FIG. 10).

There was no differences between patients with clinical benefit (PR or SD as best response) or progressive disease (PD as best response) with regard to age (mean of 57 vs. 62 years), no of previous chemotherapy regimen (mean of 2.1 vs. 2.0), Karnofsky-Index (mean of 88 vs. 88%). Only the number of metastatic sites was higher in patient with clinical benefit with a mean of 3.0 in comparison to 2.2 in patient without benefit. The difference is not statistically significant.

The intensity (mean and max) of IHC staining was similar between patients with clinical benefit and progressive disease. The number of cells stained was different between both groups. The maximum number of cells stained and the mean number of cells stained were higher in the patients with clinical benefit with a maximum of 76% vs. 66% and a mean of 70% vs. 66%, respectively.

Differences were also observed regarding location of the metastases. In the patients with clinical benefit the frequency of pleural effusion (30% vs. 10%), peritoneal carcinomatosis (40% vs. 0%) and ascites (40% vs. 20%) was higher compared to patients with progressive disease as best response. The presence of liver metastases was much lower (20% vs. 70%) in patients with clinical benefit.

In conclusion, the tumor status (according to RECIST) at 2 weeks after the 5th IMAB362 infusion (V9) was compared to baseline. For 31 patients (FAS) at least one staging after baseline was available. Patients were enrolled at a terminal stage of disease with a median of 2.0 previous chemotherapies and 2.0 metastatic sites.

A confirmed partial response was assessed in four patients leading to a overall response rate of 13%. Three of them are currently ongoing and duration could not be calculated. Additionally, eight patients had a stabilization of disease leading to a disease control rate of 39%. At the time of analysis the progression free survival of these 12 patients with clinical benefit ranged from 6 and 40 weeks. Median could not calculated since event was not recorded for 7 of these patients so far. In 9 of the patients with clinical benefit at least one tumor marker was elevated at baseline and dropped by −35 to −76% in 6 of them concomitantly. Interestingly also 4 patients with progressive disease as best response had a decrease between −29 and −54% of at least one of the elevated tumor markers during course of the study. The overall median progression free survival was 10 weeks with a range of 4 to ~40 weeks.

In patients with clinical benefit (4 PR+8 SD=39%) the incidence of peritoneal carcinomatosis, pleural effusion and ascites was higher, and the incidence of liver metastases was lower than in patients without benefit. On the other hand one patient with a confirmed partial response had frequent liver metastases.

With the current data set it seems that patients with a clinical benefit had a higher number of cells with positive IHC staining.

Moreover, ancillary data was collected in selected patients, showing that the patients serum components and the patients PBMCs are fully functional and potent in mediating the major IMAB362 modes of action CDC and ADCC, respectively.

In conclusion, anti-tumor activity (partial response, stable disease, tumor marker decrease) has been observed and IMAB362 warrants further investigation.

D. Overall Conclusions

This trial was designed as a phase IIa, multi-center, non-randomized, inter-patient multiple-dose escalation, open-label clinical study with 3 cohorts. Patients eligible for this clinical trial were requested being refractory to standard treatment or being without accepted therapy.

For this interim report 34 patients were evaluable for safety analysis (APT set) thereof 4 were enrolled in cohort 1 (300 mg/m$^2$), 6 in cohort 2 (600 mg/m$^2$) and 20 in cohort 3 (600 mg/m$^2$). IMAB362 given in a multiple dose schedule was safe and well-tolerated in heavy pretreated patients with gastro-esophageal cancer, with nausea and vomiting being the most common related adverse event. Most adverse events were mild to moderate. There were only two patients with allergic reactions, one of moderate degree, one severe. There were no grade 4 and grade 5 adverse events (including laboratory parameters) in this phase IIa study and the previous phase I study. That IMAB352 did so far not cause grade 4 related AEs is remarkable, since the majority of registered monoclonal antibodies are associated with life threatening grade 4 and 5 side effects. The indication metastatic breast cancer for bevacizumab has been revoked by the FDA in November 2011, after initial preliminary approval in 2008. Bevacizumab did not prolong life and caused severe high blood pressure and hemorrhaging, with bowel perforation and nasal septum perforation. Cetuximab causes acne-like rashes and grade 3-4 infusion reactions, anaphylaxis and cardiac arrest, necessitating anti-histamine diphenhydramine prophylaxis before treatment. Trastuzumab is still widely used, while it causes symptomatic cardiac dysfunction in 2 to 7% of patients, which is known for more than 10 years.

The primary measure for the assessment of potential antitumoral activity was the tumor status according to RECIST. There were 31 patients who had at least this one evaluation after baseline, and they were therefore included in the FAS. Four PR and 8 SD in 31 (RR 13%, DCR of 39%) heavily pretreated patients compares very well with response results in other phase II studies with approved targeted monotherapy as secondary or late stage treatment.

Cetuximab an EGFR antagonist achieved a RR of 3% (with additional 7% SD) in late stage (majority had 2 or more metastatic sites and previous therapies) GEC measured after 8 weeks in a phase II trial with thirty patients. In a second study with 55 late stage patients cetuximab led to 5% RR and additional 11% of SDs measured after 8 weeks. Similar response rates were achieved in EGFR positive refractory mCRC patients where cetuximab was approved later in this indication. Sunitinib and erlotinib were tested in late stage GEC patients in different phase II studies with in total some 150 patients. The DCR after 6-8 weeks varied between 16 and 39% and the response rate was reported between 3 and 7%, respectively.

The phase II objective response rate for trastuzumab as secondary therapy in breast cancer was 11% with in addition 9% SD of ≥6 months. For erlotinib in pretreated lung cancer a response rate of 9% was reported. Sorafenib achieved a RR between 2% to 18% in two phase II trials in renal cancer and for temsirolimus a RR of 7% was reported in a renal cancer trial. Later these targeted therapy compounds were further developed in combination with chemotherapy and became registered in these indications.

IMAB362 is a safe and effective antibody. As expected from the exquisite tissue-specificity of the targeted surface molecule and the high precision binding of the antibody, the investigational drug is well tolerated in comparison with other marketed targeted therapy. Moreover, in several patients evidence for clinical activity has been observed, comparable or better to phase II results of other already marketed targeted therapies.

Example 5: IMAB362 Induced Nausea/Vomiting

It was observed that IMAB362 induces nausea/vomiting up to NCI-CTC grade 3. The symptomatology can be described as follows: (i) not dose-dependent, (ii) acute onset, mostly within the first minutes of infusion, may continue after finalization of infusion, (iii) starts with epigastric cramps, hypersalivation, (iv) vomiting may start without prodromi, (v) rare in patients with total gastrectomy, (vi) reaction at first infusion indicative versus symptoms increase from cycle to cycle.

The fact that these adverse reactions do rarely occur in patients, who have undergone total gastrectomy, suggests that the underlying mechanism is an on-target effect. With IMAB362 vomiting is more frequent than nausea and is often reported to occur without prodromal nausea. Onset may be both acute as well as delayed. We hypothesize that small amounts of IMAB362 bind to restrictively accessible tight junction epitope. This results in a localized disruption of tight junctions and leakage of gastric acid leaks into submucosa. Resulting tissue reactions and cramps initiate a nausea/vomiting cascade.

Thus, recommended countermeasures are efficient antiemetic prophylaxis and gastric mucosa protection.

For example, patients shall receive antiemetic prophylaxis prior to starting medication. For both prophylaxis and curative intervention, a combination of a NK-1 receptor (e.g. Aprepitant/Emend) and a 5-HT3 receptor blocker (e.g. Ondansetron/Zofran) are recommended and may be extended with additional compounds. Antiemetic medication preferably is given for at least the first three days of each cycle. Prophylactic administration of butylscopolamin/buscopan shortly before each IMAB362 infusion may be considered.

Any measure for mucosal protection may reduce gastric symptoms. In this respect, proton pump inhibitors and/or misoprostol may be used and may, for example, be administered on days 1-2 or 3 of each cycle. Nonsteroidal anti-inflammatory drugs (NSAIDs) should not be used, but acetaminophen is allowed. If acetaminophen is not efficient for pain management NSAIDs can be used if required for pain management to avoid opioid treatment. Patients receiving NSAIDs are preferably treated with proton pump inhibitors and/or Misoprostol.

Thus, antiemetic prophylaxis and gastric mucosa protection may be started shortly before IMAB362 infusion. For example, the following combination may be administered, intravenous application being preferred:

NK-1 RA: e.g. Aprepitant/Emend (150 mg IV)
5-HT3 RA: e.g. Palonosetron (0.25 mg IV), Ondansetron/Zofran (8 mg IV), Granisetron (3 mg IV)
butylscopolamin/buscopan
Proton pump inhibitor: Pantoprazol/Pantozol
Optionally, Metoclopramid/MCP, Lorazepam, and/or Atropin may also be administered.

IMAB362 is an antibody, which relies dominantly on immunological modes of action, which may be compromised by immunosuppressive compounds. For this reason, steroids should be avoided in antiemetic prophylaxis and only used, if other compounds have failed.

Furthermore, exposure to IMAB362 should be attentive. For example, close monitoring in first 15-30 min is recommended. If necessary, infusion rate should be slowed (e.g. up to 4 h instead 2 h) and infusion breaks should be included.

Antiemetic medication as well as gastric mucosa protection could be continued for e.g. up to day 3 of each cycle.

The invention claimed is:

1. A method of treating a cancer disease in a human patient, wherein the cancer disease is selected from the group consisting of cancer of the stomach, cancer of the esophagus, cancer of the eso-gastric junction, and gastroesophageal cancer, wherein the method comprises administering to the patient an antibody, said antibody having the ability of binding to CLDN18.2, wherein said antibody is a chimeric antibody comprising a heavy chain variable region (VH) having an amino acid sequence of SEQ ID NO: 32, and a light chain variable region (VL) having an amino acid sequence of SEQ ID NO: 39, and wherein the antibody mediates killing of cells expressing CLDN18.2, wherein the antibody is administered to the patient at a dose of at least 600 mg/m$^2$ to 1200 mg/m$^2$, and wherein the antibody is administered in a combination therapy comprising at least one agent selected from the group consisting of anthracyclines, platinum compounds, nucleoside analogs, taxanes, camptothecin analogs, and prodrugs thereof.

2. The method of claim 1, wherein the antibody mediates cell killing by one or more of complement dependent cytotoxicity (CDC) mediated lysis, antibody dependent cellular cytotoxicity (ADCC) mediated lysis, induction of apoptosis and inhibition of proliferation.

3. The method of claim 1, wherein the cancer is gastroesophageal cancer.

4. The method of claim 1, wherein the antibody comprises a heavy chain having an amino acid sequence of SEQ ID NO: 17 and a light chain having an amino acid sequence of SEQ ID NO: 24.

5. The method of claim 1, wherein the antibody comprises a human kappa light chain constant region and a human IgG1 heavy chain constant region.

6. The method of claim 5, wherein the human kappa light chain constant region is allotype Km(3) and/or the human IgG1 heavy chain constant region is allotype G1m(3).

7. The method of claim 5, wherein the human kappa light chain constant region comprises an amino acid sequence of SEQ ID NO: 12 and/or the human IgG1 heavy chain constant region comprises an amino acid sequence of SEQ ID NO: 13.

8. The method of claim 5, wherein the human kappa light chain constant region is allotype Km(3) and the human IgG1 heavy chain constant region is allotype G1m(3).

9. The method of claim 5, wherein the human kappa light chain constant region comprises an amino acid sequence of SEQ ID NO: 12 and the human IgG1 heavy chain constant region comprises an amino acid sequence of SEQ ID NO: 13.

10. The method of claim 5, wherein the cancer is gastroesophageal cancer.

11. The method of claim 5, wherein the dose is 600 mg/m$^2$.

12. The method of claim 5, wherein the 600 mg/m$^2$ dose is administered two or more times, wherein each administration is separated by a time interval of at least 14 days.

13. The method of claim 5, wherein the dose is 1000 mg/m$^2$.

14. The method of claim 13, wherein the 1000 mg/m$^2$ dose is administered two or more times, wherein each administration is separated by a time interval of at least 14 days.

15. The method of claim 1, wherein the dose is 600 mg/m$^2$.

16. The method of claim 15, wherein the 600 mg/m$^2$ dose is administered two or more times, wherein each administration is separated by a time interval of at least 14 days.

17. The method of claim 1, wherein the dose is 1000 mg/m$^2$.

18. The method of claim 17, wherein the 1000 mg/m$^2$ dose is administered two or more times, wherein each administration is separated by a time interval of at least 14 days.

19. The method of claim 1, wherein the combination therapy comprises (i) capecitabine and oxaliplatin, (ii) folinic acid, 5-fluorouracil or a prodrug thereof, and oxaliplatin, or (iii) epirubicin, oxaliplatin and 5-fluorouracil or a prodrug thereof.

* * * * *

SEQUENCE LISTING

```
<160> NUMBER OF SEQ ID NOS: 50

<210> SEQ ID NO 1
<211> LENGTH: 261
<212> TYPE: PRT
<213> ORGANISM: Homo sapiens

<400> SEQUENCE: 1

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 2
<211> LENGTH: 261
<212> TYPE: PRT
<213> ORGANISM: Homo sapiens

<400> SEQUENCE: 2

Met Ser Thr Thr Thr Cys Gln Val Val Ala Phe Leu Leu Ser Ile Leu
1               5                   10                  15
```

```
Gly Leu Ala Gly Cys Ile Ala Ala Thr Gly Met Asp Met Trp Ser Thr
            20                  25                  30
Gln Asp Leu Tyr Asp Asn Pro Val Thr Ser Val Phe Gln Tyr Glu Gly
        35                  40                  45
Leu Trp Arg Ser Cys Val Arg Gln Ser Ser Gly Phe Thr Glu Cys Arg
 50                  55                  60
Pro Tyr Phe Thr Ile Leu Gly Leu Pro Ala Met Leu Gln Ala Val Arg
 65                  70                  75                  80
Ala Leu Met Ile Val Gly Ile Val Leu Gly Ala Ile Gly Leu Leu Val
                85                  90                  95
Ser Ile Phe Ala Leu Lys Cys Ile Arg Ile Gly Ser Met Glu Asp Ser
            100                 105                 110
Ala Lys Ala Asn Met Thr Leu Thr Ser Gly Ile Met Phe Ile Val Ser
        115                 120                 125
Gly Leu Cys Ala Ile Ala Gly Val Ser Val Phe Ala Asn Met Leu Val
130                 135                 140
Thr Asn Phe Trp Met Ser Thr Ala Asn Met Tyr Thr Gly Met Gly Gly
145                 150                 155                 160
Met Val Gln Thr Val Gln Thr Arg Tyr Thr Phe Gly Ala Ala Leu Phe
                165                 170                 175
Val Gly Trp Val Ala Gly Gly Leu Thr Leu Ile Gly Gly Val Met Met
            180                 185                 190
Cys Ile Ala Cys Arg Gly Leu Ala Pro Glu Glu Thr Asn Tyr Lys Ala
        195                 200                 205
Val Ser Tyr His Ala Ser Gly His Ser Val Ala Tyr Lys Pro Gly Gly
210                 215                 220
Phe Lys Ala Ser Thr Gly Phe Gly Ser Asn Thr Lys Asn Lys Lys Ile
225                 230                 235                 240
Tyr Asp Gly Gly Ala Arg Thr Glu Asp Glu Val Gln Ser Tyr Pro Ser
                245                 250                 255
Lys His Asp Tyr Val
            260

<210> SEQ ID NO 3
<211> LENGTH: 10
<212> TYPE: PRT
<213> ORGANISM: Homo sapiens

<400> SEQUENCE: 3

Asp Gln Trp Ser Thr Gln Asp Leu Tyr Asn
1               5                   10

<210> SEQ ID NO 4
<211> LENGTH: 11
<212> TYPE: PRT
<213> ORGANISM: Homo sapiens

<400> SEQUENCE: 4

Asn Asn Pro Val Thr Ala Val Phe Asn Tyr Gln
1               5                   10

<210> SEQ ID NO 5
<211> LENGTH: 14
<212> TYPE: PRT
<213> ORGANISM: Homo sapiens

<400> SEQUENCE: 5
```

-continued

```
Ser Thr Gln Asp Leu Tyr Asn Asn Pro Val Thr Ala Val Phe
1               5                   10

<210> SEQ ID NO 6
<211> LENGTH: 13
<212> TYPE: PRT
<213> ORGANISM: Homo sapiens

<400> SEQUENCE: 6

Thr Asn Phe Trp Met Ser Thr Ala Asn Met Tyr Thr Gly
1               5                   10

<210> SEQ ID NO 7
<211> LENGTH: 13
<212> TYPE: PRT
<213> ORGANISM: Homo sapiens

<400> SEQUENCE: 7

Asp Ser Ala Lys Ala Asn Met Thr Leu Thr Ser Gly Ile
1               5                   10

<210> SEQ ID NO 8
<211> LENGTH: 55
<212> TYPE: PRT
<213> ORGANISM: Homo sapiens

<400> SEQUENCE: 8

Met Asp Gln Trp Ser Thr Gln Asp Leu Tyr Asn Asn Pro Val Thr Ala
1               5                   10                  15

Val Phe Asn Tyr Gln Gly Leu Trp Arg Ser Cys Val Arg Glu Ser Ser
            20                  25                  30

Gly Phe Thr Glu Cys Arg Gly Tyr Phe Thr Leu Leu Gly Leu Pro Ala
        35                  40                  45

Met Leu Gln Ala Val Arg Ala
    50                  55

<210> SEQ ID NO 9
<211> LENGTH: 24
<212> TYPE: PRT
<213> ORGANISM: Homo sapiens

<400> SEQUENCE: 9

Phe Ala Leu Lys Cys Ile Arg Ile Gly Ser Met Glu Asp Ser Ala Lys
1               5                   10                  15

Ala Asn Met Thr Leu Thr Ser Gly
            20

<210> SEQ ID NO 10
<211> LENGTH: 40
<212> TYPE: PRT
<213> ORGANISM: Homo sapiens

<400> SEQUENCE: 10

Ala Asn Met Leu Val Thr Asn Phe Trp Met Ser Thr Ala Asn Met Tyr
1               5                   10                  15

Thr Gly Met Gly Gly Met Val Gln Thr Val Gln Thr Arg Tyr Thr Phe
            20                  25                  30

Gly Ala Ala Leu Phe Val Gly Trp
        35                  40

<210> SEQ ID NO 11
<211> LENGTH: 153
```

<212> TYPE: PRT
<213> ORGANISM: Homo sapiens

<400> SEQUENCE: 11

```
Met Asp Gln Trp Ser Thr Gln Asp Leu Tyr Asn Asn Pro Val Thr Ala
1               5                   10                  15

Val Phe Asn Tyr Gln Gly Leu Trp Arg Ser Cys Val Arg Glu Ser Ser
                20                  25                  30

Gly Phe Thr Glu Cys Arg Gly Tyr Phe Thr Leu Leu Gly Leu Pro Ala
            35                  40                  45

Met Leu Gln Ala Val Arg Ala Leu Met Ile Val Gly Ile Val Leu Gly
    50                  55                  60

Ala Ile Gly Leu Leu Val Ser Ile Phe Ala Leu Lys Cys Ile Arg Ile
65                  70                  75                  80

Gly Ser Met Glu Asp Ser Ala Lys Ala Asn Met Thr Leu Thr Ser Gly
                85                  90                  95

Ile Met Phe Ile Val Ser Gly Leu Cys Ala Ile Ala Gly Val Ser Val
            100                 105                 110

Phe Ala Asn Met Leu Val Thr Asn Phe Trp Met Ser Thr Ala Asn Met
        115                 120                 125

Tyr Thr Gly Met Gly Gly Met Val Gln Thr Val Gln Thr Arg Tyr Thr
    130                 135                 140

Phe Gly Ala Ala Leu Phe Val Gly Trp
145                 150
```

<210> SEQ ID NO 12
<211> LENGTH: 107
<212> TYPE: PRT
<213> ORGANISM: Artificial
<220> FEATURE:
<223> OTHER INFORMATION: Description of artificial sequence: Translation of PCR product

<400> SEQUENCE: 12

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 13
<211> LENGTH: 326
<212> TYPE: PRT
<213> ORGANISM: Artificial
<220> FEATURE:
<223> OTHER INFORMATION: Description of artificial sequence: Translation of PCR product

<400> SEQUENCE: 13

Gly Pro Ser Val Phe Pro Leu Ala Pro Ser Ser Lys Ser Thr Ser Gly

```
                1               5                  10                  15
        Gly Thr Ala Ala Leu Gly Cys Leu Val Lys Asp Tyr Phe Pro Glu Pro
                       20                  25                  30

Val Thr Val Ser Trp Asn Ser Gly Ala Leu Thr Ser Gly Val His Thr
                       35                  40                  45

Phe Pro Ala Val Leu Gln Ser Ser Gly Leu Tyr Ser Leu Ser Ser Val
                       50                  55                  60

Val Thr Val Pro Ser Ser Leu Gly Thr Gln Thr Tyr Ile Cys Asn
        65                  70                  75                  80

Val Asn His Lys Pro Ser Asn Thr Lys Val Asp Lys Val Glu Pro
                            85                  90                  95

Lys Ser Cys Asp Lys Thr His Thr Cys Pro Pro Cys Pro Ala Pro Glu
                           100                 105                 110

Leu Leu Gly Gly Pro Ser Val Phe Leu Phe Pro Pro Lys Pro Lys Asp
                           115                 120                 125

Thr Leu Met Ile Ser Arg Thr Pro Glu Val Thr Cys Val Val Val Asp
                130                 135                 140

Val Ser His Glu Asp Pro Glu Val Lys Phe Asn Trp Tyr Val Asp Gly
        145                 150                 155                 160

Val Glu Val His Asn Ala Lys Thr Lys Pro Arg Glu Glu Gln Tyr Asn
                            165                 170                 175

Ser Thr Tyr Arg Val Val Ser Val Leu Thr Val Leu His Gln Asp Trp
                        180                 185                 190

Leu Asn Gly Lys Glu Tyr Lys Cys Lys Val Ser Asn Lys Ala Leu Pro
                        195                 200                 205

Ala Pro Ile Glu Lys Thr Ile Ser Lys Ala Lys Gly Gln Pro Arg Glu
                210                 215                 220

Pro Gln Val Tyr Thr Leu Pro Pro Ser Arg Asp Glu Leu Thr Lys Asn
        225                 230                 235                 240

Gln Val Ser Leu Thr Cys Leu Val Lys Gly Phe Tyr Pro Ser Asp Ile
                            245                 250                 255

Ala Val Glu Trp Glu Ser Asn Gly Gln Pro Glu Asn Asn Tyr Lys Thr
                        260                 265                 270

Thr Pro Pro Val Leu Asp Ser Asp Gly Ser Phe Phe Leu Tyr Ser Lys
                        275                 280                 285

Leu Thr Val Asp Lys Ser Arg Trp Gln Gln Gly Asn Val Phe Ser Cys
                    290                 295                 300

Ser Val Met His Glu Ala Leu His Asn His Tyr Thr Gln Lys Ser Leu
        305                 310                 315                 320

Ser Leu Ser Pro Gly Lys
                            325

<210> SEQ ID NO 14
<211> LENGTH: 466
<212> TYPE: PRT
<213> ORGANISM: Artificial
<220> FEATURE:
<223> OTHER INFORMATION: Description of artificial sequence: chimeric
      monoclonal antibody

<400> SEQUENCE: 14

Met Glu Trp Thr Trp Val Phe Leu Phe Leu Leu Ser Val Thr Ala Gly
1               5                  10                  15

Val His Ser Gln Val Gln Leu Gln Gln Ser Gly Ala Glu Leu Met Lys
                20                  25                  30
```

```
Pro Gly Ala Ser Val Lys Ile Ser Cys Lys Ala Thr Gly Tyr Thr Phe
             35                  40                  45

Ser Ser Tyr Trp Ile Glu Trp Val Lys Gln Arg Pro Gly His Gly Leu
 50                  55                  60

Glu Trp Ile Gly Glu Ile Leu Pro Gly Ser Gly Ser Thr Asn Tyr Asn
 65                  70                  75                  80

Glu Lys Phe Lys Gly Lys Ala Thr Phe Thr Ala Asp Thr Ser Ser Asn
             85                  90                  95

Thr Ala Tyr Met Gln Leu Ser Ser Leu Thr Ser Glu Asp Ser Ala Val
                100                 105                 110

Tyr Tyr Cys Ala Arg Tyr Asp Tyr Pro Trp Phe Ala Tyr Trp Gly Gln
            115                 120                 125

Gly Thr Leu Val Thr Val Ser Ala Ala Ser Thr Lys Gly Pro Ser Val
        130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
        210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
```

```
                450                 455                 460

Gly Lys
465

<210> SEQ ID NO 15
<211> LENGTH: 467
<212> TYPE: PRT
<213> ORGANISM: Artificial
<220> FEATURE:
<223> OTHER INFORMATION: Description of artificial sequence: chimeric
      monoclonal antibody

<400> SEQUENCE: 15

Met Asp Trp Leu Trp Asn Leu Leu Phe Leu Met Ala Ala Gln Ser
1               5                   10                  15

Ile Gln Ala Gln Ile Gln Leu Val Gln Ser Gly Pro Glu Leu Lys Lys
                20                  25                  30

Pro Gly Glu Thr Val Lys Ile Ser Cys Lys Ala Ser Gly Tyr Thr Phe
            35                  40                  45

Thr Asn Tyr Gly Met Asn Trp Val Lys Gln Ala Pro Gly Lys Gly Leu
        50                  55                  60

Lys Trp Met Gly Trp Ile Asn Thr Asn Thr Gly Glu Pro Thr Tyr Ala
65                  70                  75                  80

Glu Glu Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Leu Gly Phe Gly Asn Ala Met Asp Tyr Trp Gly
        115                 120                 125

Gln Gly Thr Ser Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335
```

```
Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
                450                 455                 460

Pro Gly Lys
465

<210> SEQ ID NO 16
<211> LENGTH: 465
<212> TYPE: PRT
<213> ORGANISM: Artificial
<220> FEATURE:
<223> OTHER INFORMATION: Description of artificial sequence: chimeric
      monoclonal antibody

<400> SEQUENCE: 16

Met Glu Trp Ile Trp Ile Phe Leu Phe Ile Leu Ser Gly Thr Ala Gly
1               5                   10                  15

Val His Ser Gln Val Gln Leu Gln Gln Ser Gly Ala Glu Leu Ala Arg
                20                  25                  30

Pro Gly Ala Ser Val Lys Leu Ser Cys Lys Ala Ser Gly Tyr Thr Phe
            35                  40                  45

Thr Asp Tyr Tyr Ile Asn Trp Val Lys Gln Arg Thr Gly Gln Gly Leu
    50                  55                  60

Glu Trp Ile Gly Glu Ile Tyr Pro Gly Ser Gly Asn Thr Tyr Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
                100                 105                 110

Tyr Phe Cys Ala Arg Ser Tyr Gly Ala Phe Asp Tyr Trp Gly Gln Gly
            115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
            195                 200                 205

Ser Ser Leu Gly Thr Gln Thr Tyr Ile Cys Asn Val Asn His Lys Pro
    210                 215                 220
```

```
Ser Asn Thr Lys Val Asp Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Asp Val Ser His Glu Asp
            275                 280                 285

Pro Glu Val Lys Phe Asn Trp Tyr Val Asp Gly Val Glu Val His Asn
            290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Arg Asp Glu Leu Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
    450                 455                 460

Lys
465

<210> SEQ ID NO 17
<211> LENGTH: 467
<212> TYPE: PRT
<213> ORGANISM: Artificial
<220> FEATURE:
<223> OTHER INFORMATION: Description of artificial sequence: chimeric
      monoclonal antibody

<400> SEQUENCE: 17

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Ile Asn Trp Val Lys Gln Arg Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
```

```
                100             105             110
Tyr Tyr Cys Thr Arg Ser Trp Arg Gly Asn Ser Phe Asp Tyr Trp Gly
            115             120             125

Gln Gly Thr Thr Leu Thr Val Ser Ser Ala Ser Thr Lys Gly Pro Ser
            130             135             140

Val Phe Pro Leu Ala Pro Ser Ser Lys Ser Thr Ser Gly Gly Thr Ala
145             150             155             160

Ala Leu Gly Cys Leu Val Lys Asp Tyr Phe Pro Glu Pro Val Thr Val
            165             170             175

Ser Trp Asn Ser Gly Ala Leu Thr Ser Gly Val His Thr Phe Pro Ala
            180             185             190

Val Leu Gln Ser Ser Gly Leu Tyr Ser Leu Ser Ser Val Val Thr Val
            195             200             205

Pro Ser Ser Ser Leu Gly Thr Gln Thr Tyr Ile Cys Asn Val Asn His
            210             215             220

Lys Pro Ser Asn Thr Lys Val Asp Lys Lys Val Glu Pro Lys Ser Cys
225             230             235             240

Asp Lys Thr His Thr Cys Pro Pro Cys Pro Ala Pro Glu Leu Leu Gly
            245             250             255

Gly Pro Ser Val Phe Leu Phe Pro Pro Lys Pro Lys Asp Thr Leu Met
            260             265             270

Ile Ser Arg Thr Pro Glu Val Thr Cys Val Val Val Asp Val Ser His
            275             280             285

Glu Asp Pro Glu Val Lys Phe Asn Trp Tyr Val Asp Gly Val Glu Val
            290             295             300

His Asn Ala Lys Thr Lys Pro Arg Glu Glu Gln Tyr Asn Ser Thr Tyr
305             310             315             320

Arg Val Val Ser Val Leu Thr Val Leu His Gln Asp Trp Leu Asn Gly
            325             330             335

Lys Glu Tyr Lys Cys Lys Val Ser Asn Lys Ala Leu Pro Ala Pro Ile
            340             345             350

Glu Lys Thr Ile Ser Lys Ala Lys Gly Gln Pro Arg Glu Pro Gln Val
            355             360             365

Tyr Thr Leu Pro Pro Ser Arg Asp Glu Leu Thr Lys Asn Gln Val Ser
            370             375             380

Leu Thr Cys Leu Val Lys Gly Phe Tyr Pro Ser Asp Ile Ala Val Glu
385             390             395             400

Trp Glu Ser Asn Gly Gln Pro Glu Asn Asn Tyr Lys Thr Thr Pro Pro
            405             410             415

Val Leu Asp Ser Asp Gly Ser Phe Phe Leu Tyr Ser Lys Leu Thr Val
            420             425             430

Asp Lys Ser Arg Trp Gln Gln Gly Asn Val Phe Ser Cys Ser Val Met
            435             440             445

His Glu Ala Leu His Asn His Tyr Thr Gln Lys Ser Leu Ser Leu Ser
            450             455             460

Pro Gly Lys
465

<210> SEQ ID NO 18
<211> LENGTH: 466
<212> TYPE: PRT
<213> ORGANISM: Artificial
<220> FEATURE:
<223> OTHER INFORMATION: Description of artificial sequence: chimeric
      monoclonal antibody
```

-continued

```
<400> SEQUENCE: 18

Met Glu Trp Arg Ile Phe Leu Phe Ile Leu Ser Gly Thr Ala Gly Val
1               5                   10                  15

His Ser Gln Val Gln Leu Gln Gln Ser Gly Pro Glu Leu Val Lys Pro
            20                  25                  30

Gly Ala Ser Val Lys Met Ser Cys Lys Ala Ser Gly Tyr Thr Phe Thr
        35                  40                  45

Asp Tyr Val Ile Ser Trp Val Lys Gln Arg Thr Gly Gln Gly Leu Glu
    50                  55                  60

Trp Ile Gly Glu Ile Tyr Pro Gly Ser Gly Ser Thr Tyr Tyr Asn Glu
65                  70                  75                  80

Lys Phe Lys Gly Lys Ala Thr Leu Thr Ala Asp Lys Ser Ser Asn Thr
                85                  90                  95

Ala Tyr Met Gln Leu Ser Ser Leu Thr Ser Glu Asp Ser Ala Val Tyr
            100                 105                 110

Phe Cys Ala Arg Gly Val Leu Leu Arg Ala Met Asp Tyr Trp Gly Gln
        115                 120                 125

Gly Thr Ser Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
```

```
                     405                 410                 415
Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 19
<211> LENGTH: 469
<212> TYPE: PRT
<213> ORGANISM: Artificial
<220> FEATURE:
<223> OTHER INFORMATION: Description of artificial sequence: chimeric
      monoclonal antibody

<400> SEQUENCE: 19

Met Asp Trp Ile Trp Ile Met Leu His Leu Leu Ala Ala Ala Thr Gly
 1               5                  10                  15

Ile Gln Ser Gln Val His Leu Gln Gln Ser Gly Ser Glu Leu Arg Ser
            20                  25                  30

Pro Gly Ser Ser Val Lys Leu Ser Cys Lys Asp Phe Asp Ser Glu Val
        35                  40                  45

Phe Pro Phe Ala Tyr Met Ser Trp Ile Arg Gln Lys Pro Gly His Gly
    50                  55                  60

Phe Glu Trp Ile Gly Asp Ile Leu Pro Ser Ile Gly Arg Thr Ile Tyr
65                  70                  75                  80

Gly Glu Lys Phe Glu Asp Lys Ala Thr Leu Asp Ala Asp Thr Val Ser
                85                  90                  95

Asn Thr Ala Tyr Leu Glu Leu Asn Ser Leu Thr Ser Glu Asp Ser Ala
            100                 105                 110

Ile Tyr Tyr Cys Ala Arg Gly Glu Gly Tyr Gly Ala Trp Phe Ala Tyr
        115                 120                 125

Trp Gly Gln Gly Thr Leu Val Thr Val Ser Ala Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285
```

```
Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Lys
465

<210> SEQ ID NO 20
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 20

Met Glu Ser Gln Thr Gln Val Leu Met Ser Leu Leu Phe Trp Val Ser
1               5                   10                  15

Gly Thr Cys Gly Asp Ile Val Met Thr Gln Ser Pro Ser Ser Leu Thr
                20                  25                  30

Val Thr Ala Gly Glu Lys Val Thr Met Ser Cys Lys Ser Ser Gln Ser
            35                  40                  45

Leu Leu Asn Ser Gly Asn Gln Lys Asn Tyr Leu Thr Trp Tyr Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
                100                 105                 110

Tyr Cys Gln Asn Asp Tyr Ser Tyr Pro Leu Thr Phe Gly Ala Gly Thr
            115                 120                 125

Lys Leu Glu Leu Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175
```

```
Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 21
<211> LENGTH: 235
<212> TYPE: PRT
<213> ORGANISM: Artificial
<220> FEATURE:
<223> OTHER INFORMATION: Description of artificial sequence: chimeric
      monoclonal antibody

<400> SEQUENCE: 21

Met His Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Thr Cys Ser Ala Ser
        35                  40                  45

Ser Ser Val Ser Tyr Met His Trp Phe Gln Gln Lys Pro Gly Thr Ser
    50                  55                  60

Pro Lys Leu Trp Ile Tyr Ser Thr Ser Asn Leu Ala Ser Gly Val Pro
65                  70                  75                  80

Ala Arg Phe Ser Gly Ser Gly Ser Gly Thr Ser Tyr Ser Leu Thr Ile
            85                  90                  95

Ser Arg Met Glu Ala Glu Asp Ala Ala Thr Tyr Tyr Cys Gln Gln Arg
        100                 105                 110

Ser Ser Tyr Pro Pro Thr Phe Gly Gly Gly Thr Lys Leu Glu Ile Lys
    115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
            165                 170                 175

Ser Gly Asn Ser Gln Glu Ser Val Thr Glu Gln Asp Ser Lys Asp Ser
        180                 185                 190

Thr Tyr Ser Leu Ser Ser Thr Leu Thr Leu Ser Lys Ala Asp Tyr Glu
    195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235

<210> SEQ ID NO 22
<211> LENGTH: 234
<212> TYPE: PRT
<213> ORGANISM: Artificial
<220> FEATURE:
<223> OTHER INFORMATION: Description of artificial sequence: chimeric
      monoclonal antibody

<400> SEQUENCE: 22
```

```
Met Glu Phe Gln Thr Gln Val Phe Val Leu Leu Trp Leu Ser
1               5                   10                  15

Gly Val Asp Gly Asp Ile Val Met Thr Gln Ser Gln Lys Phe Met Ser
                20                  25                  30

Thr Ser Val Gly Asp Arg Val Ser Ile Thr Cys Lys Ala Ser Gln Asn
            35                  40                  45

Val Arg Thr Ala Val Ala Trp Tyr Gln Gln Lys Pro Gly Gln Ser Pro
50                      55                  60

Lys Ala Leu Ile Tyr Leu Ala Ser Asn Arg His Thr Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Asp Tyr Phe Cys Leu Gln His Trp
            100                 105                 110

Asn Tyr Pro Leu Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 23
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 23

Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Leu Ala
                20                  25                  30

Val Ser Val Gly Glu Lys Val Thr Met Ser Cys Lys Ser Ser Gln Ser
            35                  40                  45

Leu Leu Tyr Ser Ser Asn Gln Lys Asn Tyr Leu Ala Trp Tyr Gln Gln
        50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Ser Tyr Pro Leu Thr Phe Gly Ala Gly Thr
```

```
            115                 120                 125
Lys Leu Glu Leu Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
            210                 215                 220

Gln Gly Leu Ser Ser Pro Val Thr Lys Ser Phe Asn Arg Gly Glu Cys
225                 230                 235                 240

<210> SEQ ID NO 24
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 24

Met Glu Ser Gln Thr Gln Val Leu Met Ser Leu Leu Phe Trp Val Ser
1               5                   10                  15

Gly Thr Cys Gly Asp Ile Val Met Thr Gln Ser Pro Ser Ser Leu Thr
                20                  25                  30

Val Thr Ala Gly Glu Lys Val Thr Met Ser Cys Lys Ser Ser Gln Ser
            35                  40                  45

Leu Leu Asn Ser Gly Asn Gln Lys Asn Tyr Leu Thr Trp Tyr Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Asp Tyr Ser Tyr Pro Phe Thr Phe Gly Ser Gly Thr
        115                 120                 125

Lys Leu Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
            210                 215                 220

Gln Gly Leu Ser Ser Pro Val Thr Lys Ser Phe Asn Arg Gly Glu Cys
225                 230                 235                 240
```

<210> SEQ ID NO 25
<211> LENGTH: 239
<212> TYPE: PRT
<213> ORGANISM: Artificial
<220> FEATURE:
<223> OTHER INFORMATION: Description of artificial sequence: chimeric monoclonal antibody

<400> SEQUENCE: 25

Met Asp Ser Gln Ala Gln Val Leu Ile Leu Leu Leu Trp Val Ser
1               5                   10                  15

Gly Thr Cys Gly Asp Ile Val Met Ser Gln Ser Pro Ser Ser Leu Ala
                20                  25                  30

Val Ser Ala Gly Glu Lys Val Thr Met Ser Cys Lys Ser Ser Gln Ser
            35                  40                  45

Leu Leu Asn Ser Arg Thr Arg Lys Asn Tyr Leu Ala Trp Tyr Gln Gln
        50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
                100                 105                 110

Tyr Cys Lys Gln Ser Tyr Asn Leu Tyr Thr Phe Gly Gly Gly Thr Lys
            115                 120                 125

Leu Glu Ile Lys Arg Thr Val Ala Ala Pro Ser Val Phe Ile Phe Pro
        130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 26
<211> LENGTH: 240
<212> TYPE: PRT
<213> ORGANISM: Artificial
<220> FEATURE:
<223> OTHER INFORMATION: Description of artificial sequence: chimeric monoclonal antibody

<400> SEQUENCE: 26

Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Leu Ala
                20                  25                  30

Val Ser Val Gly Glu Lys Val Thr Met Ser Cys Lys Ser Ser Gln Ser
            35                  40                  45

Leu Leu Tyr Ser Ser Asn Gln Lys Asn Tyr Leu Ala Trp Tyr Gln Gln
        50                  55                  60

```
Lys Pro Gly Gln Ser Pro Lys Leu Leu Ile Tyr Trp Ala Ser Thr Arg
 65                  70                  75                  80

Glu Ser Gly Val Pro Asp Arg Phe Thr Gly Ser Gly Ser Ala Thr Asp
                 85                  90                  95

Phe Thr Leu Thr Ile Ser Ser Val Gln Ala Glu Asp Leu Ala Asp Tyr
                100                 105                 110

His Cys Gly Gln Gly Tyr Ser Tyr Pro Tyr Thr Phe Gly Gly Gly Thr
                115                 120                 125

Lys Leu Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
                195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

<210> SEQ ID NO 27
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 27

Met Asp Ser Gln Ala Gln Val Leu Met Leu Leu Leu Leu Trp Val Ser
 1               5                  10                  15

Gly Thr Cys Gly Asp Ile Val Met Ser Gln Ser Pro Ser Ser Leu Ala
                20                  25                  30

Val Ser Val Gly Glu Lys Val Thr Met Ser Cys Lys Ser Ser Gln Ser
                35                  40                  45

Leu Leu Tyr Ser Ser Asn Gln Lys Asn Tyr Leu Ala Trp Tyr Gln Gln
 50                  55                  60

Lys Pro Gly Gln Ser Pro Lys Leu Leu Ile Tyr Trp Ala Ser Thr Arg
 65                  70                  75                  80

Glu Ser Gly Val Pro Asp Arg Phe Thr Gly Ser Gly Ser Gly Thr Asp
                 85                  90                  95

Phe Thr Leu Thr Ile Ser Ser Val Lys Ala Glu Asp Leu Ala Val Tyr
                100                 105                 110

Tyr Cys Gln Gln Tyr Tyr Ser Tyr Pro Leu Thr Phe Gly Ala Gly Thr
                115                 120                 125

Lys Leu Glu Leu Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190
```

```
Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 28
<211> LENGTH: 234
<212> TYPE: PRT
<213> ORGANISM: Artificial
<220> FEATURE:
<223> OTHER INFORMATION: Description of artificial sequence: chimeric
      monoclonal antibody

<400> SEQUENCE: 28

Met Glu Ser Gln Thr Leu Val Phe Ile Ser Ile Leu Leu Trp Leu Tyr
1               5                   10                  15

Gly Ala Asp Gly Asn Ile Val Met Thr Gln Ser Pro Lys Ser Met Ser
            20                  25                  30

Met Ser Val Gly Glu Arg Val Thr Leu Thr Cys Lys Ala Ser Glu Asn
        35                  40                  45

Val Val Thr Tyr Val Ser Trp Tyr Gln Gln Lys Pro Glu Gln Ser Pro
    50                  55                  60

Lys Leu Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Lys Ala Glu Asp Leu Ala Val Tyr Tyr Cys Gln Gln Tyr Tyr
            100                 105                 110

Ser Tyr Pro Leu Thr Phe Gly Ala Gly Thr Lys Leu Glu Leu Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 29
<211> LENGTH: 117
<212> TYPE: PRT
<213> ORGANISM: Artificial
<220> FEATURE:
<223> OTHER INFORMATION: Description of artificial sequence: Translation
      of PCR product

<400> SEQUENCE: 29

Gln Val Gln Leu Gln Gln Ser Gly Ala Glu Leu Met Lys Pro Gly Ala
1               5                   10                  15
```

```
Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Asp Tyr Pro Trp Phe Ala Tyr Trp Gly Gln Gly Thr Leu
            100                 105                 110

Val Thr Val Ser Ala
        115

<210> SEQ ID NO 30
<211> LENGTH: 118
<212> TYPE: PRT
<213> ORGANISM: Artificial
<220> FEATURE:
<223> OTHER INFORMATION: Description of artificial sequence: Translation
      of PCR product

<400> SEQUENCE: 30

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Leu Gly Phe Gly Asn Ala Met Asp Tyr Trp Gly Gln Gly Thr
            100                 105                 110

Ser Val Thr Val Ser Ser
        115

<210> SEQ ID NO 31
<211> LENGTH: 116
<212> TYPE: PRT
<213> ORGANISM: Artificial
<220> FEATURE:
<223> OTHER INFORMATION: Description of artificial sequence: Translation
      of PCR product

<400> SEQUENCE: 31

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg Thr Gly Gln Gly Leu Glu Trp Ile
        35                  40                  45

Gly Glu Ile Tyr Pro Gly Ser Gly Asn Thr Tyr Tyr Asn Glu Lys Phe
    50                  55                  60
```

```
Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Ser Tyr Gly Ala Phe Asp Tyr Trp Gly Gln Gly Thr Thr Leu
            100                 105                 110

Thr Val Ser Ser
        115

<210> SEQ ID NO 32
<211> LENGTH: 118
<212> TYPE: PRT
<213> ORGANISM: Artificial
<220> FEATURE:
<223> OTHER INFORMATION: Description of artificial sequence: Translation
      of PCR product

<400> SEQUENCE: 32

Gln Val Gln Leu Gln Gln Pro Gly Ala Glu Leu Val Arg Pro Gly Ala
1               5                  10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
 65                  70                  75                  80

Met Gln Leu Ser Ser Pro Thr Ser Glu Asp Ser Ala Val Tyr Tyr Cys
                 85                  90                  95

Thr Arg Ser Trp Arg Gly Asn Ser Phe Asp Tyr Trp Gly Gln Gly Thr
            100                 105                 110

Thr Leu Thr Val Ser Ser
        115

<210> SEQ ID NO 33
<211> LENGTH: 118
<212> TYPE: PRT
<213> ORGANISM: Artificial
<220> FEATURE:
<223> OTHER INFORMATION: Description of artificial sequence: Translation
      of PCR product

<400> SEQUENCE: 33

Gln Val Gln Leu Gln Gln Ser Gly Pro Glu Leu Val Lys Pro Gly Ala
1               5                  10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Glu Ile Tyr Pro Gly Ser Gly Ser Thr Tyr Tyr Asn Glu Lys Phe
    50                  55                  60

Lys Gly Lys Ala Thr Leu Thr Ala Asp Lys Ser Ser Asn Thr Ala Tyr
 65                  70                  75                  80

Met Gln Leu Ser Ser Leu Thr Ser Glu Asp Ser Ala Val Tyr Phe Cys
                 85                  90                  95

Ala Arg Gly Val Leu Leu Arg Ala Met Asp Tyr Trp Gly Gln Gly Thr
            100                 105                 110
```

Ser Val Thr Val Ser Ser
        115

<210> SEQ ID NO 34
<211> LENGTH: 120
<212> TYPE: PRT
<213> ORGANISM: Artificial
<220> FEATURE:
<223> OTHER INFORMATION: Description of artificial sequence: Translation
      of PCR product

<400> SEQUENCE: 34

Gln Val His Leu Gln Gln Ser Gly Ser Glu Leu Arg Ser Pro Gly Ser
1               5                   10                  15

Ser Val Lys Leu Ser Cys Lys Asp Phe Asp Ser Glu Val Phe Pro Phe
            20                  25                  30

Ala Tyr Met Ser Trp Ile Arg Gln Lys Pro Gly His Gly Phe Glu Trp
        35                  40                  45

Ile Gly Asp Ile Leu Pro Ser Ile Gly Arg Thr Ile Tyr Gly Glu Lys
    50                  55                  60

Phe Glu Asp Lys Ala Thr Leu Asp Ala Asp Thr Val Ser Asn Thr Ala
65                  70                  75                  80

Tyr Leu Glu Leu Asn Ser Leu Thr Ser Glu Asp Ser Ala Ile Tyr Tyr
                85                  90                  95

Cys Ala Arg Gly Glu Gly Tyr Gly Ala Trp Phe Ala Tyr Trp Gly Gln
            100                 105                 110

Gly Thr Leu Val Thr Val Ser Ala
        115                 120

<210> SEQ ID NO 35
<211> LENGTH: 113
<212> TYPE: PRT
<213> ORGANISM: Artificial
<220> FEATURE:
<223> OTHER INFORMATION: Description of artificial sequence: Translation
      of PCR product

<400> SEQUENCE: 35

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

<210> SEQ ID NO 36
<211> LENGTH: 106
<212> TYPE: PRT
<213> ORGANISM: Artificial
<220> FEATURE:

<223> OTHER INFORMATION: Description of artificial sequence: Translation of PCR product

<400> SEQUENCE: 36

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
                85                  90                  95

Phe Gly Gly Gly Thr Lys Leu Glu Ile Lys
            100                 105

<210> SEQ ID NO 37
<211> LENGTH: 107
<212> TYPE: PRT
<213> ORGANISM: Artificial
<220> FEATURE:
<223> OTHER INFORMATION: Description of artificial sequence: Translation of PCR product

<400> SEQUENCE: 37

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Ala Trp Tyr Gln Gln Lys Pro Gly Gln Ser Pro Lys Ala Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Leu
                85                  90                  95

Thr Phe Gly Gly Gly Thr Lys Leu Glu Ile Lys
            100                 105

<210> SEQ ID NO 38
<211> LENGTH: 113
<212> TYPE: PRT
<213> ORGANISM: Artificial
<220> FEATURE:
<223> OTHER INFORMATION: Description of artificial sequence: Translation of PCR product

<400> SEQUENCE: 38

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val

```
                    50                  55                  60
Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                     85                  90                  95

Tyr Tyr Ser Tyr Pro Leu Thr Phe Gly Ala Gly Thr Lys Leu Glu Leu
                100                 105                 110

Lys

<210> SEQ ID NO 39
<211> LENGTH: 113
<212> TYPE: PRT
<213> ORGANISM: Artificial
<220> FEATURE:
<223> OTHER INFORMATION: Description of artificial sequence: Translation
      of PCR product

<400> SEQUENCE: 39

Asp Ile Val Met Thr Gln Ser Pro Ser Ser Leu Thr Val Thr Ala Gly
  1               5                  10                  15

Glu Lys Val Thr Met Ser Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
             35                  40                  45

Pro Pro Lys Leu Leu Ile Tyr Trp Ala Ser Thr Arg Glu Ser Gly Val
         50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                     85                  90                  95

Asp Tyr Ser Tyr Pro Phe Thr Phe Gly Ser Gly Thr Lys Leu Glu Ile
                100                 105                 110

Lys

<210> SEQ ID NO 40
<211> LENGTH: 112
<212> TYPE: PRT
<213> ORGANISM: Artificial
<220> FEATURE:
<223> OTHER INFORMATION: Description of artificial sequence: Translation
      of PCR product

<400> SEQUENCE: 40

Asp Ile Val Met Ser Gln Ser Pro Ser Ser Leu Ala Val Ser Ala Gly
  1               5                  10                  15

Glu Lys Val Thr Met Ser Cys Lys Ser Ser Gln Ser Leu Leu Asn Ser
                 20                  25                  30

Arg Thr Arg Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
         50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                     85                  90                  95

Ser Tyr Asn Leu Tyr Thr Phe Gly Gly Gly Thr Lys Leu Glu Ile Lys
                100                 105                 110
```

<210> SEQ ID NO 41
<211> LENGTH: 113
<212> TYPE: PRT
<213> ORGANISM: Artificial
<220> FEATURE:
<223> OTHER INFORMATION: Description of artificial sequence: Translation of PCR product

<400> SEQUENCE: 41

Asp Ile Val Met Ser Gln Ser Pro Ser Ser Leu Ala Val Ser Val Gly
1               5                   10                  15

Glu Lys Val Thr Met Ser Cys Lys Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Ala Thr Asp Phe Thr Leu Thr
65                  70                  75                  80

Ile Ser Ser Val Gln Ala Glu Asp Leu Ala Asp Tyr His Cys Gly Gln
                85                  90                  95

Gly Tyr Ser Tyr Pro Tyr Thr Phe Gly Gly Gly Thr Lys Leu Glu Ile
            100                 105                 110

Lys

<210> SEQ ID NO 42
<211> LENGTH: 113
<212> TYPE: PRT
<213> ORGANISM: Artificial
<220> FEATURE:
<223> OTHER INFORMATION: Description of artificial sequence: Translation of PCR product

<400> SEQUENCE: 42

Asp Ile Val Met Ser Gln Ser Pro Ser Ser Leu Ala Val Ser Val Gly
1               5                   10                  15

Glu Lys Val Thr Met Ser Cys Lys Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys

<210> SEQ ID NO 43
<211> LENGTH: 107
<212> TYPE: PRT
<213> ORGANISM: Artificial
<220> FEATURE:
<223> OTHER INFORMATION: Description of artificial sequence: Translation of PCR product

<400> SEQUENCE: 43

```
Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Thr Tyr
            20                  25                  30

Val Ser Trp Tyr Gln Gln Lys Pro Glu Gln Ser Pro Lys Leu Leu Ile
            35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Lys Ala
65              70                  75                  80

Glu Asp Leu Ala Val Tyr Tyr Cys Gln Gln Tyr Tyr Ser Tyr Pro Leu
                85                  90                  95

Thr Phe Gly Ala Gly Thr Lys Leu Glu Leu Lys
            100                 105
```

<210> SEQ ID NO 44
<211> LENGTH: 15
<212> TYPE: PRT
<213> ORGANISM: Artificial
<220> FEATURE:
<223> OTHER INFORMATION: Epitope

<400> SEQUENCE: 44

```
Met Asp Gln Trp Ser Thr Gln Asp Leu Tyr Asn Asn Pro Val Thr
1               5                   10                  15
```

<210> SEQ ID NO 45
<211> LENGTH: 15
<212> TYPE: PRT
<213> ORGANISM: Artificial
<220> FEATURE:
<223> OTHER INFORMATION: Epitope

<400> SEQUENCE: 45

```
Ser Thr Gln Asp Leu Tyr Asn Asn Pro Val Thr Ala Val Phe Asn
1               5                   10                  15
```

<210> SEQ ID NO 46
<211> LENGTH: 15
<212> TYPE: PRT
<213> ORGANISM: Artificial
<220> FEATURE:
<223> OTHER INFORMATION: Epitope

<400> SEQUENCE: 46

```
Leu Tyr Asn Asn Pro Val Thr Ala Val Phe Asn Tyr Gln Gly Leu
1               5                   10                  15
```

<210> SEQ ID NO 47
<211> LENGTH: 15
<212> TYPE: PRT
<213> ORGANISM: Artificial
<220> FEATURE:
<223> OTHER INFORMATION: Epitope

<400> SEQUENCE: 47

```
Pro Val Thr Ala Val Phe Asn Tyr Gln Gly Leu Trp Arg Ser Cys
1               5                   10                  15
```

<210> SEQ ID NO 48
<211> LENGTH: 15
<212> TYPE: PRT
<213> ORGANISM: Artificial
<220> FEATURE:

```
<223> OTHER INFORMATION: Epitope

<400> SEQUENCE: 48

Val Phe Asn Tyr Gln Gly Leu Trp Arg Ser Cys Val Arg Glu Ser
1               5                   10                  15

<210> SEQ ID NO 49
<211> LENGTH: 15
<212> TYPE: PRT
<213> ORGANISM: Artificial
<220> FEATURE:
<223> OTHER INFORMATION: Epitope

<400> SEQUENCE: 49

Gln Gly Leu Trp Arg Ser Cys Val Arg Glu Ser Ser Gly Phe Thr
1               5                   10                  15

<210> SEQ ID NO 50
<211> LENGTH: 15
<212> TYPE: PRT
<213> ORGANISM: Artificial
<220> FEATURE:
<223> OTHER INFORMATION: Epitope

<400> SEQUENCE: 50

Arg Ser Cys Val Arg Glu Ser Ser Gly Phe Thr Glu Cys Arg Gly
1               5                   10                  15
```